United States Patent
Hang et al.

(10) Patent No.: US 10,723,771 B2
(45) Date of Patent: Jul. 28, 2020

(54) MODIFIED MICROORGANISMS EXPRESSING SAGA AS ANTI-INFECTIVE AGENTS, PROBIOTICS AND FOOD COMPONENTS

(71) Applicant: The Rockefeller University, New York, NY (US)

(72) Inventors: Howard Hang, New York, NY (US); Kavita Rangan, New York, NY (US); Daniel Mucida, New York, NY (US); Virginia Pedicord, New York, NY (US)

(73) Assignee: THE ROCKEFELLER UNIVERSITY, New York, NY (US)

( * ) Notice: Subject to any disclaimer, the term of this patent is extended or adjusted under 35 U.S.C. 154(b) by 97 days.

(21) Appl. No.: 15/568,726

(22) PCT Filed: Apr. 22, 2016

(86) PCT No.: PCT/US2016/028836
§ 371 (c)(1),
(2) Date: Oct. 23, 2017

(87) PCT Pub. No.: WO2016/172476
PCT Pub. Date: Oct. 27, 2016

(65) Prior Publication Data
US 2019/0211067 A1    Jul. 11, 2019

Related U.S. Application Data

(60) Provisional application No. 62/152,478, filed on Apr. 24, 2015.

(51) Int. Cl.
| | | |
|---|---|---|
| *C12N 15/31* | (2006.01) | |
| *C07K 14/315* | (2006.01) | |
| *A23K 10/18* | (2016.01) | |
| *A23L 33/135* | (2016.01) | |
| *A61P 31/04* | (2006.01) | |
| *A23C 9/12* | (2006.01) | |
| *A23C 9/123* | (2006.01) | |
| *A61K 35/744* | (2015.01) | |
| *A61K 35/00* | (2006.01) | |

(52) U.S. Cl.
CPC .......... *C07K 14/315* (2013.01); *A23C 9/1203* (2013.01); *A23C 9/1234* (2013.01); *A23K 10/18* (2016.05); *A23L 33/135* (2016.08); *A61K 35/744* (2013.01); *A61P 31/04* (2018.01); *A23V 2002/00* (2013.01); *A23Y 2220/67* (2013.01); *A61K 2035/11* (2013.01)

(58) Field of Classification Search
None
See application file for complete search history.

(56) References Cited

U.S. PATENT DOCUMENTS

2002/0146429 A1    10/2002    Ching-Hsaing et al.

FOREIGN PATENT DOCUMENTS

| WO | 99/49049 A1 | 9/1999 |
| WO | 2009/042956 A1 | 4/2009 |
| WO | 2010127784 A1 | 11/2010 |

OTHER PUBLICATIONS

Masood et al (Critical Reviews in Microbiology, 2011; 37(1): 91-98).*
Blanot et al., Synthesis and Biological Evaluation of Biological Evaluation of Biotinyl Hydrazone Derivatives of Muramyl Peptides: Biotinylated Muramyl Peptides, Chemical Biology and Drug Design, vol. 79, No. 1, pp. 2-8, Jan. 1, 2012.
Traub et al., Structural Requirements of Synthetic Muropeptides to Synergize with Lipopolysaccharide in Cytokine Induction, Journal of Biological Chemistry, vol. 279, No. 10, pp. 8694-8700, Mar. 5, 2004.
Takada et al., Structural Characteristics of Peptidoglycan Fragments Required to Prime Mice for Induction of Anaphylactoid Reactions by Lipopolysaccharides, Infection and Immunity, vol. 64, No. 2, pp. 657-659, Feb. 1, 1996.
Rangan et al., A secreted bacterial peptidoglycan hydrolase enhances tolerance to enteric pathogens, Science, vol. 353, No. 6306, pp. 1434-1437, Sep. 22, 2016.
Pedicord et al., Exploiting a host-commensal interaction to promote intestinal barrier function and enteric pathogen tolerance, Science Immunology, vol. 1, No. 3, pp. 1-29, Sep. 22, 2016.
Ayers et al., Microbes Dress for Success: Tolerance or Resistance?, Trends in Microbiology, vol. 25, No. 1, pp. 1-3, Jan. 1, 2017.
Teng, F., et al., An Enterococcus faecium Secreted Antigen, Saga, Exhibits Broad-Spectrum Binding to Extracellular Matrix Proteins and Appears Essential for E. faecium Growth, Infection and Immunity, Sep. 2003, vol. 71, No. 9, pp. 5033-5041.

* cited by examiner

*Primary Examiner* — Jennifer E Graser
(74) *Attorney, Agent, or Firm* — Saliwanchik, Lloyd & Eisenschenk

(57) ABSTRACT

Provided are compositions and methods based in part on the discovery that *Enterococcus faecium* heterologous secreted antigen A (SagA)-produced peptidoglycan fragments are protective against enteric bacterial infections. Modified bacteria that are engineered to express heterologous SagA are provided, and are included a nutraceutical, pharmaceutical, and probiotic formulations, and as components of food products, including dairy products. The modified bacteria include modified *Lactobacillus* bacteria that express heterologous SagA. The disclosure includes a method that involves introducing into an individual modified bacteria of that express and secrete heterologous SagA. The disclosure provides isolated peptidoglycan fragment preparations made by a exposing a composition that contains peptidoglycan to an isolated or recombinant SagA, or to modified bacteria expressing a heterologous SagA, allowing SagA to generate the peptidoglycan fragments, and separating the peptidoglycan fragments from the composition to obtain the isolated peptidoglycan fragments or a preparation that contains them.

14 Claims, 25 Drawing Sheets
Specification includes a Sequence Listing.

Efl = Enterococcus faecalis
Efm - Enterococcus faecium

SEQUENCE LISTING

```
<160> NUMBER OF SEQ ID NOS: 44

<210> SEQ ID NO 1
<211> LENGTH: 530
<212> TYPE: PRT
<213> ORGANISM: Enterococcus faecium

<400> SEQUENCE: 1

Met Lys Lys Ser Leu Ile Ser Ala Val Met Cys Ser Met Thr Leu
1               5                   10                  15

Thr Ala Val Ala Ser Pro Ile Ala Ala Ala Asp Asp Phe Asp Ser
                20                  25                  30

Gln Ile Gln Gln Asp Gln Lys Ile Ala Asp Leu Lys Asn Gln Gln
            35                  40                  45

Ala Asp Ala Gln Ser Gln Ile Asp Ala Leu Glu Ser Gln Val Ser Glu
        50                  55                  60

Ile Asn Thr Gln Ala Gln Asp Leu Leu Ala Lys Gln Asp Thr Leu Arg
65                  70                  75                  80

Gln Glu Ser Ala Gln Leu Val Lys Asp Ile Ala Asp Leu Gln Glu Arg
                85                  90                  95

Ile Glu Lys Arg Glu Asp Thr Ile Gln Lys Gln Ala Arg Glu Ala Gln
                100                 105                 110

Val Ser Asn Thr Ser Ser Asn Tyr Ile Asp Ala Val Leu Asn Ala Asp
            115                 120                 125

Ser Leu Ala Asp Ala Ile Gly Arg Val Gln Ala Met Thr Thr Met Val
        130                 135                 140

Lys Ala Asn Asn Asp Leu Met Glu Gln Gln Lys Gln Asp Lys Lys Ala
145                 150                 155                 160

Val Glu Asp Lys Lys Ala Glu Asn Asp Ala Lys Leu Lys Glu Leu Ala
                165                 170                 175

Glu Asn Gln Ala Ala Leu Glu Ser Gln Lys Gly Asp Leu Leu Ser Lys
                180                 185                 190

Gln Ala Asp Leu Asn Val Leu Lys Thr Ser Leu Ala Ala Glu Gln Ala
            195                 200                 205

Thr Ala Glu Asp Lys Lys Ala Asp Leu Asn Arg Gln Lys Ala Glu Ala
        210                 215                 220

Glu Ala Glu Gln Ala Arg Ile Arg Glu Gln Gln Arg Leu Ala Glu Gln
225                 230                 235                 240

Ala Arg Gln Gln Ala Ala Gln Glu Lys Ala Glu Lys Glu Ala Arg Glu
                245                 250                 255

Gln Ala Glu Ala Glu Ala Gln Ala Thr Gln Ala Ser Ser Thr Ala Gln
```

```
            260                 265                 270
Ser Ser Ala Ser Glu Glu Ser Ala Ala Gln Ser Ser Thr Thr Glu
        275                 280                 285

Glu Ser Ser Ala Ala Gln Ser Ser Thr Thr Glu Glu Ser Thr Thr
        290                 295                 300

Ala Pro Glu Ser Ser Thr Thr Glu Glu Ser Thr Thr Ala Pro Glu Ser
305                 310                 315                 320

Ser Thr Thr Glu Glu Ser Thr Thr Val Pro Glu Ser Ser Thr Thr Glu
                325                 330                 335

Glu Ser Thr Thr Val Pro Glu Ser Ser Thr Glu Glu Ser Thr Thr
                340                 345                 350

Val Pro Glu Ser Ser Thr Thr Glu Glu Ser Thr Thr Val Pro Glu Thr
        355                 360                 365

Ser Thr Glu Glu Ser Thr Thr Pro Ala Pro Thr Thr Pro Ser Thr Asp
        370                 375                 380

Gln Ser Val Asp Pro Gly Asn Ser Thr Gly Ser Asn Ala Thr Asn Asn
385                 390                 395                 400

Thr Thr Asn Thr Thr Pro Thr Pro Thr Pro Ser Gly Ser Val Asn Gly
                405                 410                 415

Ala Ala Ile Val Ala Glu Ala Tyr Lys Tyr Ile Gly Thr Pro Tyr Val
                420                 425                 430

Trp Gly Gly Lys Asp Pro Ser Gly Phe Asp Cys Ser Gly Phe Thr Arg
        435                 440                 445

Tyr Val Tyr Leu Gln Val Thr Gly Arg Asp Ile Gly Gly Trp Thr Val
        450                 455                 460

Pro Gln Glu Ser Ala Gly Thr Lys Ile Ser Val Ser Gln Ala Lys Ala
465                 470                 475                 480

Gly Asp Leu Leu Phe Trp Gly Ser Pro Gly Gly Thr Tyr His Val Ala
                485                 490                 495

Ile Ala Leu Gly Gly Gly Gln Tyr Ile His Ala Pro Gln Pro Gly Glu
                500                 505                 510

Ser Val Lys Val Gly Ser Val Gln Trp Phe Ala Pro Asp Phe Ala Val
        515                 520                 525

Ser Met
    530

<210> SEQ ID NO 2
<211> LENGTH: 37
<212> TYPE: DNA
<213> ORGANISM: artificial sequence
<220> FEATURE:
<223> OTHER INFORMATION: Primer

<400> SEQUENCE: 2
ggacatatga aaaagagttt aatatcagca gtaatgg                              37

<210> SEQ ID NO 3
<211> LENGTH: 37
<212> TYPE: DNA
<213> ORGANISM: artificial sequence
<220> FEATURE:
<223> OTHER INFORMATION: Primer

<400> SEQUENCE: 3
ggactcgagc atgctgacag caaagtcagg tgcaaac                              37

<210> SEQ ID NO 4
```

```
<211> LENGTH: 32
<212> TYPE: DNA
<213> ORGANISM: artificial sequence
<220> FEATURE:
<223> OTHER INFORMATION: Primer

<400> SEQUENCE: 4
aaatatatcg gtactcctta tgtttggggc gg                                32

<210> SEQ ID NO 5
<211> LENGTH: 32
<212> TYPE: DNA
<213> ORGANISM: artificial sequence
<220> FEATURE:
<223> OTHER INFORMATION: Primer

<400> SEQUENCE: 5
ccaagtggat ttgacgcctc aggattcaca cg                                32

<210> SEQ ID NO 6
<211> LENGTH: 32
<212> TYPE: DNA
<213> ORGANISM: artificial sequence
<220> FEATURE:
<223> OTHER INFORMATION: Primer

<400> SEQUENCE: 6
tcaccaggcg gaacttacgc cgtagcgatt gc                                32

<210> SEQ ID NO 7
<211> LENGTH: 32
<212> TYPE: DNA
<213> ORGANISM: artificial sequence
<220> FEATURE:
<223> OTHER INFORMATION: Primer

<400> SEQUENCE: 7
ggaggacaat atatcgctgc tcctcaacca gg                                32

<210> SEQ ID NO 8
<211> LENGTH: 36
<212> TYPE: DNA
<213> ORGANISM: artificial sequence
<220> FEATURE:
<223> OTHER INFORMATION: Primer

<400> SEQUENCE: 8
aacagatcaa agtgtggatc ctgggaacag tactgg                            36

<210> SEQ ID NO 9
<211> LENGTH: 37
<212> TYPE: DNA
<213> ORGANISM: artificial sequence
<220> FEATURE:
<223> OTHER INFORMATION: Primer

<400> SEQUENCE: 9
tgcacctgac tttgcggatc ccatgctcga gcaccac                           37

<210> SEQ ID NO 10
<211> LENGTH: 33
<212> TYPE: DNA
<213> ORGANISM: artificial sequence
<220> FEATURE:
<223> OTHER INFORMATION: Primer

<400> SEQUENCE: 10
```

| catcaccata tggacgattt tgattctcag ata | 33 |

<210> SEQ ID NO 11
<211> LENGTH: 27
<212> TYPE: DNA
<213> ORGANISM: artificial sequence
<220> FEATURE:
<223> OTHER INFORMATION: Primer

<400> SEQUENCE: 11

| catcacggat cctttcgggc tttgtta | 27 |

<210> SEQ ID NO 12
<211> LENGTH: 29
<212> TYPE: DNA
<213> ORGANISM: artificial sequence
<220> FEATURE:
<223> OTHER INFORMATION: Primer

<400> SEQUENCE: 12

| aaagtcgaca cgatggtggt ccaattgat | 29 |

<210> SEQ ID NO 13
<211> LENGTH: 29
<212> TYPE: DNA
<213> ORGANISM: artificial sequence
<220> FEATURE:
<223> OTHER INFORMATION: Primer

<400> SEQUENCE: 13

| tttcatatgt cattcctccg actggctta | 29 |

<210> SEQ ID NO 14
<211> LENGTH: 36
<212> TYPE: DNA
<213> ORGANISM: artificial sequence
<220> FEATURE:
<223> OTHER INFORMATION: Primer

<400> SEQUENCE: 14

| taacaaagcc cgaaaggatc ctgagttggc tgctgc | 36 |

<210> SEQ ID NO 15
<211> LENGTH: 29
<212> TYPE: DNA
<213> ORGANISM: artificial sequence
<220> FEATURE:
<223> OTHER INFORMATION: Primer

<400> SEQUENCE: 15

| aaacggccga gtggggcgtg ttattgaag | 29 |

<210> SEQ ID NO 16
<211> LENGTH: 31
<212> TYPE: DNA
<213> ORGANISM: artificial sequence
<220> FEATURE:
<223> OTHER INFORMATION: Primer

<400> SEQUENCE: 16

| tttgtcgacg ggtaagcttc tcatcgtttt g | 31 |

<210> SEQ ID NO 17
<211> LENGTH: 29
<212> TYPE: DNA

```
<213> ORGANISM: artificial sequence
<220> FEATURE:
<223> OTHER INFORMATION: Primer

<400> SEQUENCE: 17
aaactgcagt ggagccttga agaaagttg                                29

<210> SEQ ID NO 18
<211> LENGTH: 29
<212> TYPE: DNA
<213> ORGANISM: artificial sequence
<220> FEATURE:
<223> OTHER INFORMATION: Primer

<400> SEQUENCE: 18
tttggtacca ttggctgctt ttgttgctt                                29

<210> SEQ ID NO 19
<211> LENGTH: 20
<212> TYPE: DNA
<213> ORGANISM: artificial sequence
<220> FEATURE:
<223> OTHER INFORMATION: Primer

<400> SEQUENCE: 19
ctagtcctac tctttgccct                                          20

<210> SEQ ID NO 20
<211> LENGTH: 20
<212> TYPE: DNA
<213> ORGANISM: artificial sequence
<220> FEATURE:
<223> OTHER INFORMATION: Primer

<400> SEQUENCE: 20
ttgcagcctc ttgatctaca                                          20

<210> SEQ ID NO 21
<211> LENGTH: 20
<212> TYPE: DNA
<213> ORGANISM: artificial sequence
<220> FEATURE:
<223> OTHER INFORMATION: Primer

<400> SEQUENCE: 21
ctattgtaga acaagaggct                                          20

<210> SEQ ID NO 22
<211> LENGTH: 20
<212> TYPE: DNA
<213> ORGANISM: artificial sequence
<220> FEATURE:
<223> OTHER INFORMATION: Primer

<400> SEQUENCE: 22
tctccatgtt cagcgacagc                                          20

<210> SEQ ID NO 23
<211> LENGTH: 20
<212> TYPE: DNA
<213> ORGANISM: artificial sequence
<220> FEATURE:
<223> OTHER INFORMATION: Primer

<400> SEQUENCE: 23
gcgttctctt cttttgcagc                                          20
```

<210> SEQ ID NO 24
<211> LENGTH: 19
<212> TYPE: DNA
<213> ORGANISM: artificial sequence
<220> FEATURE:
<223> OTHER INFORMATION: Primer

<400> SEQUENCE: 24
aaactgagga gcagccagg                                                   19

<210> SEQ ID NO 25
<211> LENGTH: 20
<212> TYPE: DNA
<213> ORGANISM: artificial sequence
<220> FEATURE:
<223> OTHER INFORMATION: Primer

<400> SEQUENCE: 25
gtccaggctg atcctatcca                                                  20

<210> SEQ ID NO 26
<211> LENGTH: 20
<212> TYPE: DNA
<213> ORGANISM: artificial sequence
<220> FEATURE:
<223> OTHER INFORMATION: Primer

<400> SEQUENCE: 26
ggggcagcag tacaaaaatc                                                  20

<210> SEQ ID NO 27
<211> LENGTH: 20
<212> TYPE: DNA
<213> ORGANISM: artificial sequence
<220> FEATURE:
<223> OTHER INFORMATION: Primer

<400> SEQUENCE: 27
gtccaggctg atcctatcca                                                  20

<210> SEQ ID NO 28
<211> LENGTH: 20
<212> TYPE: DNA
<213> ORGANISM: artificial sequence
<220> FEATURE:
<223> OTHER INFORMATION: Primer

<400> SEQUENCE: 28
gatttctgca ggtcccaaaa                                                  20

<210> SEQ ID NO 29
<211> LENGTH: 20
<212> TYPE: DNA
<213> ORGANISM: artificial sequence
<220> FEATURE:
<223> OTHER INFORMATION: Primer

<400> SEQUENCE: 29
gtcccattca tgcgttctct                                                  20

<210> SEQ ID NO 30
<211> LENGTH: 20
<212> TYPE: DNA
<213> ORGANISM: artificial sequence
<220> FEATURE:

```
<223> OTHER INFORMATION: Primer

<400> SEQUENCE: 30
aggaccaggc tgtgtctgtc                                                  20

<210> SEQ ID NO 31
<211> LENGTH: 20
<212> TYPE: DNA
<213> ORGANISM: artificial sequence
<220> FEATURE:
<223> OTHER INFORMATION: Primer

<400> SEQUENCE: 31
tgctcctaca agttggcaga                                                  20

<210> SEQ ID NO 32
<211> LENGTH: 20
<212> TYPE: DNA
<213> ORGANISM: artificial sequence
<220> FEATURE:
<223> OTHER INFORMATION: Primer

<400> SEQUENCE: 32
taccaagcgt agcccctatg                                                  20

<210> SEQ ID NO 33
<211> LENGTH: 20
<212> TYPE: DNA
<213> ORGANISM: artificial sequence
<220> FEATURE:
<223> OTHER INFORMATION: Primer

<400> SEQUENCE: 33
acaaaaaccc cagcaacaag                                                  20

<210> SEQ ID NO 34
<211> LENGTH: 20
<212> TYPE: DNA
<213> ORGANISM: artificial sequence
<220> FEATURE:
<223> OTHER INFORMATION: Primer

<400> SEQUENCE: 34
gagcaaggga ctctggtctg                                                  20

<210> SEQ ID NO 35
<211> LENGTH: 20
<212> TYPE: DNA
<213> ORGANISM: artificial sequence
<220> FEATURE:
<223> OTHER INFORMATION: Primer

<400> SEQUENCE: 35
ggacatgggt gtctgtgttg                                                  20

<210> SEQ ID NO 36
<211> LENGTH: 20
<212> TYPE: DNA
<213> ORGANISM: artificial sequence
<220> FEATURE:
<223> OTHER INFORMATION: Primer

<400> SEQUENCE: 36
ctcactggag agttccctgg                                                  20
```

```
<210> SEQ ID NO 37
<211> LENGTH: 21
<212> TYPE: DNA
<213> ORGANISM: artificial sequence
<220> FEATURE:
<223> OTHER INFORMATION: Primer

<400> SEQUENCE: 37
ctttgtactg tggtgggagg a                                              21

<210> SEQ ID NO 38
<211> LENGTH: 20
<212> TYPE: DNA
<213> ORGANISM: artificial sequence
<220> FEATURE:
<223> OTHER INFORMATION: Primer

<400> SEQUENCE: 38
tcaagcaaga gcagctacca                                                20

<210> SEQ ID NO 39
<211> LENGTH: 20
<212> TYPE: DNA
<213> ORGANISM: artificial sequence
<220> FEATURE:
<223> OTHER INFORMATION: Primer

<400> SEQUENCE: 39
attcagaggc cccaggtagt                                                20

<210> SEQ ID NO 40
<211> LENGTH: 20
<212> TYPE: DNA
<213> ORGANISM: artificial sequence
<220> FEATURE:
<223> OTHER INFORMATION: Primer

<400> SEQUENCE: 40
tggctaaaca cgcttctcct                                                20

<210> SEQ ID NO 41
<211> LENGTH: 20
<212> TYPE: DNA
<213> ORGANISM: artificial sequence
<220> FEATURE:
<223> OTHER INFORMATION: Primer

<400> SEQUENCE: 41
caggaaggac atgtggacaa                                                20

<210> SEQ ID NO 42
<211> LENGTH: 20
<212> TYPE: DNA
<213> ORGANISM: artificial sequence
<220> FEATURE:
<223> OTHER INFORMATION: Primer

<400> SEQUENCE: 42
ttcctccttg tacggctgac                                                20

<210> SEQ ID NO 43
<211> LENGTH: 20
<212> TYPE: DNA
<213> ORGANISM: artificial sequence
<220> FEATURE:
<223> OTHER INFORMATION: Primer
```

-continued

```
<400> SEQUENCE: 43
tccacctctg ttgggttcat                                                    20

<210> SEQ ID NO 44
<211> LENGTH: 20
<212> TYPE: DNA
<213> ORGANISM: artificial sequence
<220> FEATURE:
<223> OTHER INFORMATION: Primer

<400> SEQUENCE: 44
aagcttcctt cctgtcctcc                                                    20
```

MODIFIED MICROORGANISMS EXPRESSING SAGA AS ANTI-INFECTIVE AGENTS, PROBIOTICS AND FOOD COMPONENTS

CROSS REFERENCE TO RELATED APPLICATIONS

This application claims priority to U.S. provisional patent application No. 62/152,478, filed Apr. 24, 2015, the disclosure of which is incorporated herein by reference.

STATEMENT REGARDING FEDERALLY SPONSORED RESEARCH

This invention was made with government support under contract no. R01 GM103593 awarded by the National Institutes of Health. The government has certain rights in the invention.

FIELD

The present disclosure relates generally to anti-infective agents, and more specifically to use of secreted antigen A (SagA) as an anti-infective agent, as well as recombinant microorganisms and food products expressing heterologous SagA and/or SagA-generated metabolites.

BACKGROUND

The intestinal microbiome mediates host resistance to enteric pathogens, but the underlying protection mechanisms of individual bacterial species have remained elusive (Buffie, C. G. & Pamer, E. G. Nat Rev Immunol 13, 790-801 (2013). For example, commensal strains of *Enterococcus faecium* can inhibit the virulence of several bacterial pathogens, but whether *E. faecium* directly targets pathogens or modulates host immunity is unknown (Tannock, G. W. & Cook, G. The *Enterococci*: Pathogenesis, Molecular Biology, and Antibiotic Resistance. 101-132 (ASM Press, 2002). Because enteric pathogens are responsible for gastroenteritis, but can also cause life threatening infections, there is an ongoing and unmet need for improved compositions and methods that can be used to inhibit their growth. The present disclosure meets these needs.

SUMMARY

The present disclosure is based in part on the discovery that *Enterococcus faecium* heterologous secreted antigen A (SagA)-produced peptidoglycan fragments are protective against enteric bacterial infections. Further, *E. faecium*-SagA protection is conserved and is transferable to other bacteria. As a consequence, bacteria that are engineered to heterologously express SagA can confer the same protective function against pathogenic bacteria as *E. faecium*. Furthermore, the protective effect can be elicited using *E. faecium* culture supernatant that contains peptidoglycan fragments produced by SagA activity. Aspects of the disclosure are demonstrated in both *C. elegans* and in mice and it is therefore expected that the present compositions and methods are applicable for use with a variety of animals, and against multiple types of pathogenic bacteria. Accordingly, in one aspect the disclosure provides modified bacteria that are engineered to express heterologous SagA, wherein the modified bacteria are for use in prophylaxis and/or therapy of enteric bacterial infections. The disclosure includes a proviso that the modified bacteria are not *E. coli*. In certain embodiments the modified bacteria may be selected from different types of bacteria that are suitable for use in nutraceutical, pharmaceutical, probiotic, and food based products and delivery methods, and such products and methods are also aspects of the disclosure. In non-limiting examples the modified bacteria are gram positive bacteria, such as *Lactobacillus* bacteria, and in particular may be *L. plantarum, L. casei* or *L. acidophilus*. Combinations of such bacteria, with or without other types of bacteria whether modified or unmodified, are included. In certain implementations the modified bacteria which express heterologous SagA are present in a gastrointestinal system of an animal, including but not limited to those in humans and non-human mammals.

The disclosure includes a variety of products for human or non-human animal consumption that comprise live modified bacteria. Such products include but are not limited to dairy products, such as yogurt, and drinkable dairy products. In a related aspect the modified bacteria are provided as a probiotic formulation.

In one approach the disclosure includes a method comprising introducing into an individual modified bacteria of that express and secrete heterologous SagA. The modified bacteria can be introduced into the individual as a component of a food product, a probiotic formulation, or a pharmaceutical formulation. In certain approaches the modified bacteria are introduced into an individual who is at risk for contracting an enteric bacterial infection, or the modified bacteria are given to an individual who has an enteric bacterial infection, and subsequently the pathogenicity of the bacteria is reduced. Generally the modified bacteria are introduced into the gastrointestinal system of the individual.

The disclosure provides isolated peptidoglycan fragment preparations made by a process comprising the steps of exposing a composition comprising peptidoglycan to an isolated or recombinant SagA, or to modified bacteria expressing a heterologous SagA, allowing SagA to generate the peptidoglycan fragments, and separating the peptidoglycan fragments from the composition to obtain the isolated peptidoglycan fragments or a preparation comprising them.

DETAILED DESCRIPTION OF THE INVENTION

Figure 1:
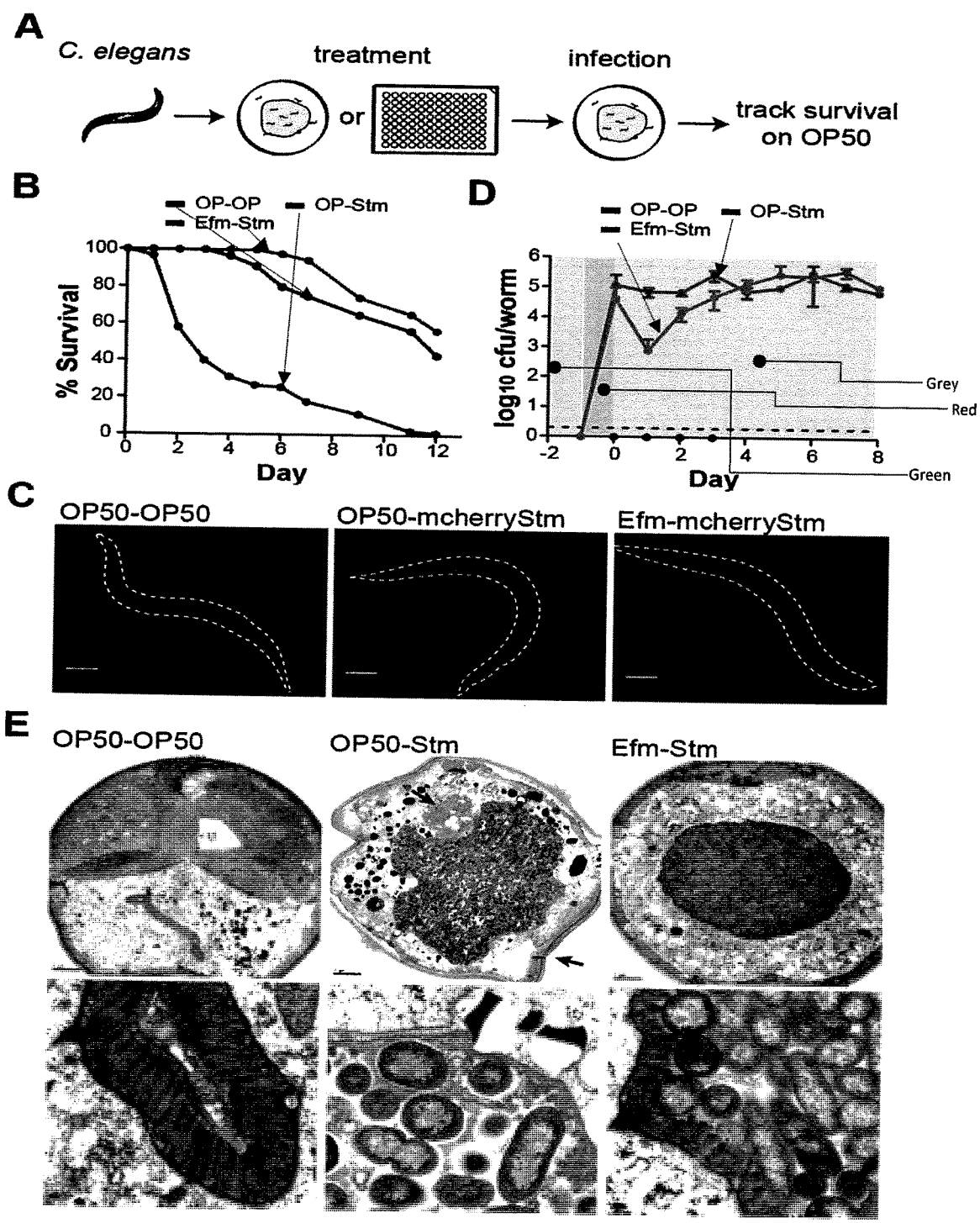
FIG. 1. *Enterococcus faecium* induces host resistance to *S. Typhimurium*. (A) Schematic of pulsed infection assay. Animals were treated on bacterial lawns for 1 day or in liquid wells for 2 hours before infection with *S. Typhimurium* for 1 day. Animals were then transferred onto *E. coli* OP50 plates for the remainder of the assay, and survival was scored. (B) Survival curve showing *E. faecium*-mediated inhibition of *S. Typhimurium* pathogenesis (p<10−10). The legend indicates treatment-infection. Control worms were fed *E. coli* OP50 for both the treatment and infection stages of the assay. For all *C. elegans* survival curves, significance was calculated by log-rank test with Bonferroni correction for multiple comparisons. Data points represent mean survival from 90 worms. (C) Fluorescence images of *C. elegans* infected with *S. Typhimurium* expressing plasmid-encoded mcherry (mcherryStm) at day 3 post-infection. The dotted lines indicate an outline of the worm body. Scale bar=100 μm. (D) *S. Typhimurium* CFUs measured in *C. elegans* throughout the infection assay. Data points represent average CFUs from 5 worms±standard deviation of two independent experiments. The dotted line indicates detection limit. The background shading represents stage of the treatment-infection assay. Green indicates treatment, red indicates infection, and grey indicates *E. coli* OP50 feeding. (E) Electron microscopy of transverse sections of *C. elegans* (top), and magnification of intestinal region (bottom) at day 4 post-infection. The intestinal microvilli are highlighted blue; the intestinal lumen is highlighted red. In the top middle panel, the top arrow indicates bacteria that have breached the epithelial barrier, and the bottom arrow indicates loss of overall turgidity. Scale bar (top row)=5 µm. Scale bar (bottom row)=200 nm. Abbreviations: *E. coli* OP50 (OP); *S. Typhimurium* (Stm); *E. faecium* (Efm).

The present disclosure is based in part on our discovery that Enterococcus faecium can inhibit pathogenesis by various strains of bacteria, including Salmonella enterica serovar Typhimurium and Clostridium difficile. Inhibition of pathogenesis is shown in Caenorhabditis elegans, which has historically been used as a model organism to study evolutionarily conserved aspects of innate immunity and microbial pathogenesis, but the inhibition of pathogenesis is also demonstrated in mice. In particular, it is demonstrated that C. elegans survival can be dramatically increased by feeding the worms E. faecium prior to infection with S. Typhimurium, as compared to worms fed control bacterial strains, and that this protective effect is unexpectedly mediated by E. faecium secreted antigen A (SagA). We determined that SagA exhibits peptidoglycan hydrolase activity and generates cell wall fragments which, without intending to be constrained by any particular theory, are believed to activate host immunity to inhibit pathogenesis. We further show that recombinant expression of SagA in non-protective commensal bacteria is sufficient for mediating host protection against pathogenic bacteria, not only in C. elegans, but also in a mouse model, wherein engineered microbes that express heterologous SagA recombinantly can extend survival of the mice after challenge with S. Typhimurium. Thus, SagA itself, and modified microorganisms which have been engineered to express SagA heterologously, are provided for use in prophylaxis and/or therapy of infections caused by a variety of enteric microbial pathogens. Microorganisms engineered to express SagA are also provided as probiotic microbes. Such microbes include but are not necessarily limited to members of the Lactobacillus genus. The probiotic microbes can be provided as pharmaceutical or nutraceutical formulations, as components of human or non-human animal food items. Moreover, we demonstrate that introducing SagA producing E. faecium into mice limits Clostridium difficile pathogenesis. The disclosure also includes preparations of cell wall fragments produced by the enzymatic activity of SagA. Thus, the disclosure encompasses or SagA-generated metabolites as further described below.

In one aspect the present disclosure provides a modified microorganism, wherein the organism expresses a heterologous SagA. A "modified" microorganism means that the microorganism has been changed relative to its naturally occurring form, such as having been engineered to express a heterologous protein. A "heterologous" SagA protein is a SagA protein that is not normally encoded by the genome of the microorganism. Accordingly, heterologous SagA production involves introducing a SagA-encoding DNA sequence into the microorganism. The modified microorganism comprises a heterologous SagA coding sequence, the expression of which is driven by a promoter operative in the microorganism. The SagA protein can be expressed from any suitable expression vector or other construct introduced into the microorganism. In embodiments the heterologous SagA is encoded by a plasmid introduced into the modified microorganism, or is encoded by a segment of DNA introduced into a bacterial chromosome. Many reagents and methods for introducing and expressing any heterologous gene in a wide variety of microorganisms are known in the art and are suitable for use with the present invention. In general, the disclosure contemplates microorganisms that are modified to express and secrete heterologous SagA that retains the ability to generate peptidoglycan fragments from a suitable peptidoglycan-containing substrate. In one embodiment, the recombinantly produced SagA protein comprises the E. faecium amino acid sequence:
MKKSLISAVMVCSMTLTAVASPIAAAADDFDSQ-IQQQDQKIADLKNQQADAQS QIDALESQV-SEINTQAQDLLAKQDTLRQESAQLVKDI- ADLQERIEKREDTIQKQAREAQV SNTSSNYIDAVLNADSLADAIGRVQAMTTMV-KANNDLMEQQKQDKKAVEDKKAEND AKLKELAE-NQAALESQKGDLLSKQADLNVLKTSLAAEQATAED-KKADLNRQKAEAEA EQARIREQQRLAEQARQQAAQEKAEKEAREQAEAE-AQATQASSTAQSSASEESSAAQSS TTEESSSAAQSST-TEESTTAPESSTTEESTTAPESSTTEESTTVPESST-TEESTTVPESSTTEE STTVPESSTTEESTTVPETSTEESTTPAPTTPSTDQS-VDPGNSTGSNATNNTTNTTPTPTPS GSVNGAAIVAE-AYKYIGTPYVWGGKDPSGFDCSGFTRYVYLQVTGR-DIGGWTVPQESA GTKISVSQAKAGDLLFWGSPGGTYHVAIALGGGQYI-HAPQPGESVKVGSVQWFAPDFA VSM (SEQ ID NO:1), or a sequence that has at least 90% identity to this sequence, provided such non-identical sequences retain N1pC/p60-type hydrolase activity, which is described further below. As can be seen from FIG. 4A, the N1pC/p60 hydrolase domain is from amino acid 389 through amino acid 530. In embodiments, other *E. faecium* SagA sequences are known and would be expected to function in place of Com15 SagA, the sequence of which is given above. However, other homologues of SagA from non-*E. faecium* species would not be expected to function for use with the present disclosure.

In embodiments, the SagA protein is modified so that it has, for example, additional or fewer amino acids than in the sequence presented above. In non-limiting examples, the SagA protein is modified to include additional amino acids used for isolation, purification, or detection, including but not necessarily limited to a series of histidine residues at the C-terminus, or a polypeptide sequence that is capable of producing a detectable signal, such as a fluorescent signal.

In embodiments, the disclosure includes modified gram negative bacteria that expresses heterologous SagA protein, with the proviso that the gram negative bacteria do not include *Escherichia coli*. In embodiments, the disclosure includes modified bacteria that are facultative anaerobes. In embodiments the modified bacteria are gram positive bacteria that expresses heterologous SagA protein. In embodiments the gram positive bacteria are members the *Lactobacillus* genus, and in particular *Lactobacillus* species that are active in the production of food products intended for human and/or non-human animal consumption. In non-limiting embodiments the modified bacteria are *Lactobacillus* species that are active in the production of dairy products, such as yogurt, milk, milk-based creams, ice cream products, and cheese, or fermented drinks, such as wine, cider and beer, or fermented foods, or combinations of the foregoing. In certain embodiments the modified bacteria are *L. plantarum, L. casei, L. acidophilus, L. salivarius,* or *L. reuteri* as well as probiotic strains of *Bifidobacterium* (i.e. *B. longum*). Data demonstrating successful heterologous production of SagA in several distinct microorganisms are provided.

In embodiments the disclosure includes combinations of modified bacteria described herein, and further comprises combinations of the modified bacteria with other microorganisms, such as yeasts. Those skilled in the art will recognize that such combinations are useful for production of certain foods.

In another aspect the disclosure comprises a food product comprising a modified bacteria that expresses a heterologous SagA protein. Such products include all of the aforementioned types of food and modified bacteria, and may further include modified *E. coli* that expresses a heterologous SagA. In embodiments the food product is a dairy product, including but not necessarily limited to yogurt, milk, milk-based creams, and cheese. Use of microorganisms in making foods that intentionally contain live cultures, such as yogurts, are well known in the art and can be adapted for use with the presently provided modified microorganisms. In one aspect the food product is a non-human animal feed, such as food intended for consumption by a bovine, equine, canine, porcine, feline, avian or reptilian animal, or by aquatic animals such as fish. In certain aspects the food product comprises packaging, such as a paper or cardboard carton, plastic container, bottle, bag, etc., that are well known for containing foods. The packaging can provide printed material which includes information that identifies the modified bacteria present in the food product.

In another aspect the disclosure includes a supplement product, such as a nutraceutical product, a dietary supplement, a food ingredient, etc., including but not limited to a probiotic formulation or functional food that contains one or more live modified bacteria as described herein. The supplement product can be provided in the form of, for example, a liquid, capsules, tablets, softgels, powders, freeze-dried compositions, and the like.

In another aspect the disclosure provides a pharmaceutical composition comprising modified microorganisms and/or isolated or purified recombinant SagA as described herein. The pharmaceutical composition can include any suitable diluent, carrier, excipient, buffer, etc., intended for use with the microorganisms for prophylactic and/or therapeutic human or veterinary purposes. Some examples of compositions suitable for preparing pharmaceutical compositions can be found in: Remington: The Science and Practice of Pharmacy (2005) 21st Edition, Philadelphia, Pa. Lippincott Williams & Wilkins. Such compositions may also be included in supplement products.

In an embodiment the disclosure includes making modified bacteria that express heterologous SagA for use in inhibiting bacterial infections, or for maintaining or modifying the intestinal flora of an individual. The method comprises introducing into bacteria a heterologous SagA encoding DNA sequence, and culturing the bacteria for use as a probiotic, nutraceutical or pharmaceutical agent. In embodiments, the disclosure comprises such bacterial cultures themselves, and further includes such cultures scaled for use in producing nutraceutical, probiotic and/or pharmaceutical preparations. In embodiments, the cultures are propagated as, for example, a yogurt culture.

In another aspect the present disclosure comprises a composition comprising isolated or purified cell wall fragments generated by SagA. In certain embodiments the disclosure includes isolated and/or purified cell wall fragments (i.e., SagA-generated metabolites) made by a process that comprises exposing a peptidoglycan containing composition of matter, such as gram negative bacteria, or a composition comprising gram negative bacteria cell walls, or another peptidoglycan containing material, to SagA, allowing SagA to generate peptidoglycan fragments, and separating the peptidoglycan fragments from the composition and the SagA to obtain an isolated peptidoglycan fragment preparation. In embodiments the SagA-generated metabolites /peptidoglycan fragment preparation comprise muramyl peptides, i.e., muropeptides. Separating the peptidoglycan fragments can be achieved using any suitable approach, including but not necessarily limited to filtration, size exclusion and column-based separation, affinity separation, etc. As is demonstrated in the Examples of this disclosure, peptidoglycan fragments can protect worms and mice from distinct types of bacterial pathogenesis. Thus, the disclosure provides a process for producing peptidoglycan fragments, and a peptidoglycan fragment preparation comprising or consisting of peptidoglycan fragments produced by that process, wherein such peptidoglycan fragment preparations are useful for the prophylaxis and/or therapy of bacterial infections.

In another aspect the disclosure includes a method comprising introducing into an individual modified bacteria wherein the modified bacteria expresses a heterologous SagA. The modified bacteria can be introduced as a component of a food product, a probiotic formulation, or a pharmaceutical formulation. In an aspect the disclosure includes a method for prophylaxis and/or therapy of a bacterial infection in an individual. The method comprises administering to an individual in need a composition comprising isolated SagA, or a bacterial population wherein at least some members of the population have been modified to produce SagA. In another approach, the composition can comprise peptidoglycan fragments generated by SagA. Compositions and uses thereof comprising combinations of peptidoglycan fragments generated by SagA, modified bacteria that express SagA and isolated SagA are also encompassed by this disclosure. Compositions of the disclosure may be used prophylactically when they are given to an individual prior to exposure to pathologic bacteria, or within a short time, i.e., several hours, after exposure to pathologic bacteria. Therapeutic approaches comprise administering the engineered bacteria to an individual who has or is suspected of having a bacterial infection, wherein the severity of the infection is lessened subsequent to the administration.

In embodiments, administering a composition to an individual for, for instance, prophylaxis and/or therapy of a bacterial infection according to this disclosure can be performed using any suitable approach. In one embodiment, the composition is consumed by the individual as a probiotic formulation, or as a component of a food item and is thus introduced orally. In another embodiment the composition is administered as a pharmaceutical formulation. The pharmaceutical formulation can be administered using any suitable route, including but not necessarily limited to parenteral, intraperitoneal, intrapulmonary, oral, intra-abdominal, and others. Parenteral infusions include intramuscular, intravenous, intraarterial, intraperitoneal, and subcutaneous administration.

The amount of modified bacteria, SagA, peptidoglycan fragments, and any other active agent to be included in a composition and/or to be used in the method can be determined by those skilled in the art, given the benefit of the present disclosure. Thus, in one embodiment, an effective amount of a composition is administered. An effective amount can be an amount of the composition that inhibits growth of bacterial cells in the individual, or reduces a sign or symptom of bacterial infection. In embodiments, the individual to whom a composition of the invention is administered has, is suspected of having, or is at risk for development of a bacterial infection. In embodiments, the bacterial infection is an infection by enteric pathogens such as strains of *Salmonella, Escherichia coli, Shigella, Campylobacter, Helicobacter, Francisella, Vibrio, Yersinia, Enterococcus*, and pathogenic strains of microbiota. In embodiments, a composition of this disclosure is administered to an individual such that the growth of enteric pathogens in the individual is inhibited, and/or the amount of enteric pathogens is reduced, or the enteric pathogens are eradicated.

Suitable dosages for either therapeutic or prophylactic purposes can be determined by those skilled in the art and will be based, at least in part, on consideration of the individual's age, sex, size, and health, the type of bacterial infection, and other factors as will be apparent to the skilled artisan. In embodiments, a composition of the invention can be administered in combination with an antibiotic.

The following description and specific Example is provided to illustrate the invention, but are not intended to be limiting in any way.

Example 1

This Example uses *Caenorhabditis elegans* to reconstitute *Enterococcus faecium* probiotic activity and identify a specific factor that enhances host resistance against enteric pathogens. Through biochemical, proteomic, and genetic approaches, we show that secreted SagA from *E. faecium* is sufficient to protect animals against *Salmonella* pathogenesis. Secreted SagA is also protective against other pathogenic microorganisms. Without intending to be constrained by any particular theory, the data show that SagA does not affect pathogen growth or virulence, but instead engages tol-1-dependent signaling to enhance host resistance to enteric pathogens. Biochemical studies demonstrate that the N1pC/p60 peptidoglycan hydrolase activity of SagA is required, and peptidoglycan fragments, i.e., muramyl-peptide fragments, generated by SagA are sufficient to protect *C. elegans* against *Salmonella* pathogenesis in a tol-1-dependent manner. This Example thus describes discovery of probiotic factors that can be used to enhance host resistance to pathogens. Such probiotic factors include but are not necessarily limited to SagA, catalytically active fragments of it, and muramyl-peptide fragments generated by SagA.

Figure 5:
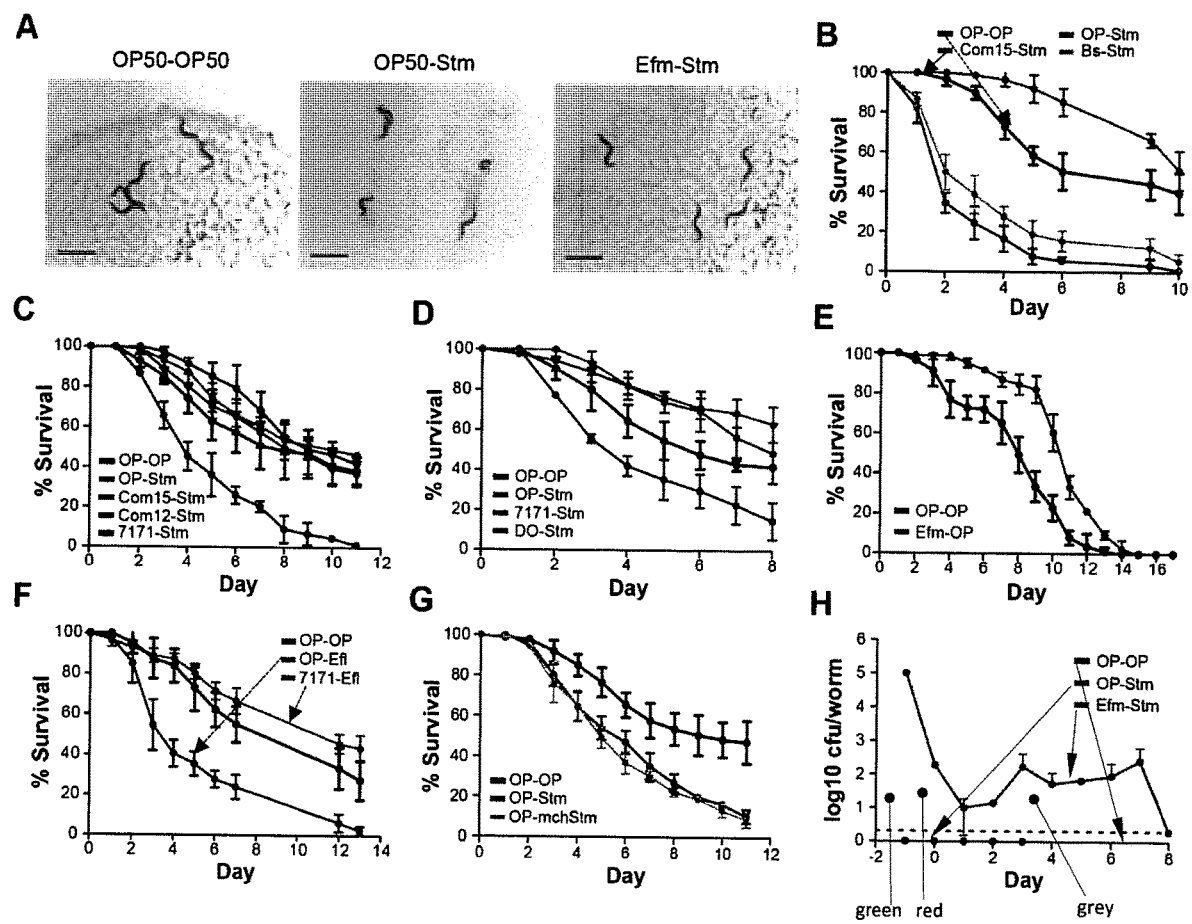
FIG. 5. Characterization of *E. faecium*-mediated protection. (A) Images of *C. elegans* 1 day post-infection. Scale bar=1 mm. (B) Survival curve showing comparable activity of Efm strains NCTC 7171 and DO. (C) Pulsed treatment-infection assay showing *E. faecium* treatment inhibits *E. coli* OP50 pathogenesis. (D) Survival curve showing that Efm NCTC 7171 can protect *C. elegans* from *E. faecalis* V583 (Efl) pathogenesis. (E) Survival curve showing comparable pathogenicity of mcherry-*S. Typhimurium* (mchStm) to wild-type *S. Typhimurium* (Stm). (F) *Enterococcus* CFUs measured in *C. elegans* throughout the pulsed treatment-infection assay. Background shading represents stage of the pulsed treatment-infection assay. Green indicated treatment, red indicates infection, and grey indicates *E. coli* OP50 feeding. The data points represent average CFUs from 5 worms±standard deviation from two independent experiments. The dotted line indicates detection limit. For (B) through (F), data points represent mean±s.d. for 3 plates of 30 worms each. Abbreviations: *E. coli* OP50 (OP); *S. typhimurium* (Stm); *E. faecium* (Efm), *E. faecalis* (Eft).

To facilitate our discovery and characterization of specific protective factors from intestinal bacteria and to develop compositions and methods of using them as described above, we employed *C. elegans* as a model organism, which has been widely used to study evolutionarily conserved aspects of innate immunity and microbial pathogenesis. We focused on *Enterococci* lactic acid bacteria that are commonly associated with the intestinal microbiome of diverse animal species ranging from humans to flies. Drug-resistant strains of *E. faecium* have emerged as nosocomial pathogens, but non-pathogenic strains of *E. faecium* can attenuate host susceptibility to enteric pathogens, including *Salmonella*, and have been employed as probiotics in humans and other animals (C. M. Franz, M. Huch, H. Abriouel, W. Holzapfel, A. Galvez, *Enterococci* as probiotics and their implications in food safety. Int J Food Microbiol 151, 125 (Dec. 2, 2011)). Nevertheless, the protection mechanisms of *E. faecium* are unclear, which limits their utility as probiotics. Interestingly, *E. faecium* can colonize the *C. elegans* intestine without causing apparent disease, which provided a unique opportunity to characterize the protective factors and conserved mechanisms underlying *E. faecium* probiotic activity. To investigate whether *E. faecium* can attenuate the pathogenesis of enteric bacteria in *C. elegans* we developed a treatment-infection assay with *Salmonella enterica* serovar *Typhimurium* (FIG. 1A). *S. Typhimurium* is a Gram-negative bacterial pathogen with a broad host range that causes persistent intestinal infection and death in *C. elegans*. In the current disclosure, *E. faecium*-treated animals appeared less fragile and more motile than control *E. coli* OP50-treated animals after *S. Typhimurium* infection (FIG. 5A). Notably, *C. elegans* survival was increased in animals fed *E. faecium* prior to infection with *S. Typhimurium* as compared to animals fed *E. coli* OP50 or *Bacillus subtilis* 168 (FIG. 1B and FIG. 5B). Multiple strains of *E. faecium* were able to inhibit *S. Typhimurium* pathogenesis, including a pig fecal isolate (NCTC 7171), two human fecal isolates (Com15 and Com12) (12) (FIG. 5C), and a pathogenic human blood isolate (DO) (X. Qin et al., Complete genome sequence of *Enterococcus faecium* strain TX16 and comparative genomic analysis of *Enterococcus faecium* genomes. BMC Microbiol 12, 135 (2012)) (FIG. 5D). *E. faecium*-treated animals were also more resistant to the intrinsic pathogenesis of *E. coli* OP50 (FIG. 5E) as well as pathogenesis caused by the Gram-positive pathogen *Enterococcus faecalis* strain V583 (A. Garsin et al., A simple model host for identifying Gram-positive virulence factors. Proc Natl Acad Sci USA 98, 10892 (Sep. 11, 2001)) (FIG. 5F). These results indicate that despite the genetic variation across the *E. faecium* strains tested, the mechanism of protection is conserved amongst *E. faecium* strains and may be active against diverse enteric pathogens.

To evaluate the mechanism of *E. faecium*-mediated protection, we first analyzed the effect of *E. faecium* treatment on *S. Typhimurium* colonization and persistence. Fluorescence imaging of mCherry-*S. Typhimurium* 3 days post-infection showed comparable *S. Typhimurium* colonization of animals with or without *E. faecium* treatment (FIG. 1C and FIG. 5G). Viable *S. Typhimurium* counts (CFUs) recovered from lysed worms revealed a ~2 log decrease in *S. Typhimurium* colonization 1 day post-infection in *E. faecium*-treated *S. Typhimurium*-infected animals (FIG. 1D). However, by 3 days post-infection, *S. Typhimurium* titer was similar in OP50- and *E. faecium*-treated *S. Typhimurium*-infected animals (FIG. 1D). To determine if this transient decrease in *S. Typhimurium* colonization represented direct niche competition early in the assay, we monitored *E. faecium* CFUs throughout the infection assay (FIG. 5H). While *E. faecium* initially colonized worms to ~$10^5$ CFUs/worm, *E. faecium* numbers decreased to ~$10$-$10^2$ per worm 1 day post-infection, demonstrating that the transient decrease in *S. Typhimurium* colonization was not concomitant with an increase in *E. faecium* load. Electron microscopy of worm transverse sections 4 days post-infection revealed substantial degradation of the intestinal microvilli in OP50-treated *S. Typhimurium*-infected animals as compared to uninfected or *E. faecium*-treated animals (FIG. 1E). In OP50-treated *S. Typhimurium*-infected animals, bacteria had escaped the intestinal lumen and caused extensive tissue damage (FIG. 1E, middle panel). In contrast, *E. faecium*-treated *S. Typhimurium*-infected animals contained a similar bacterial load to the intestinal lumen and showed no apparent tissue damage (FIG. 1E, right panel), indicating improved epithelial barrier integrity. These results demonstrate that *E. faecium* does not prevent *S. Typhimurium* colonization or replication in vivo, but may enhance host resistance to pathogens.

Figure 2:
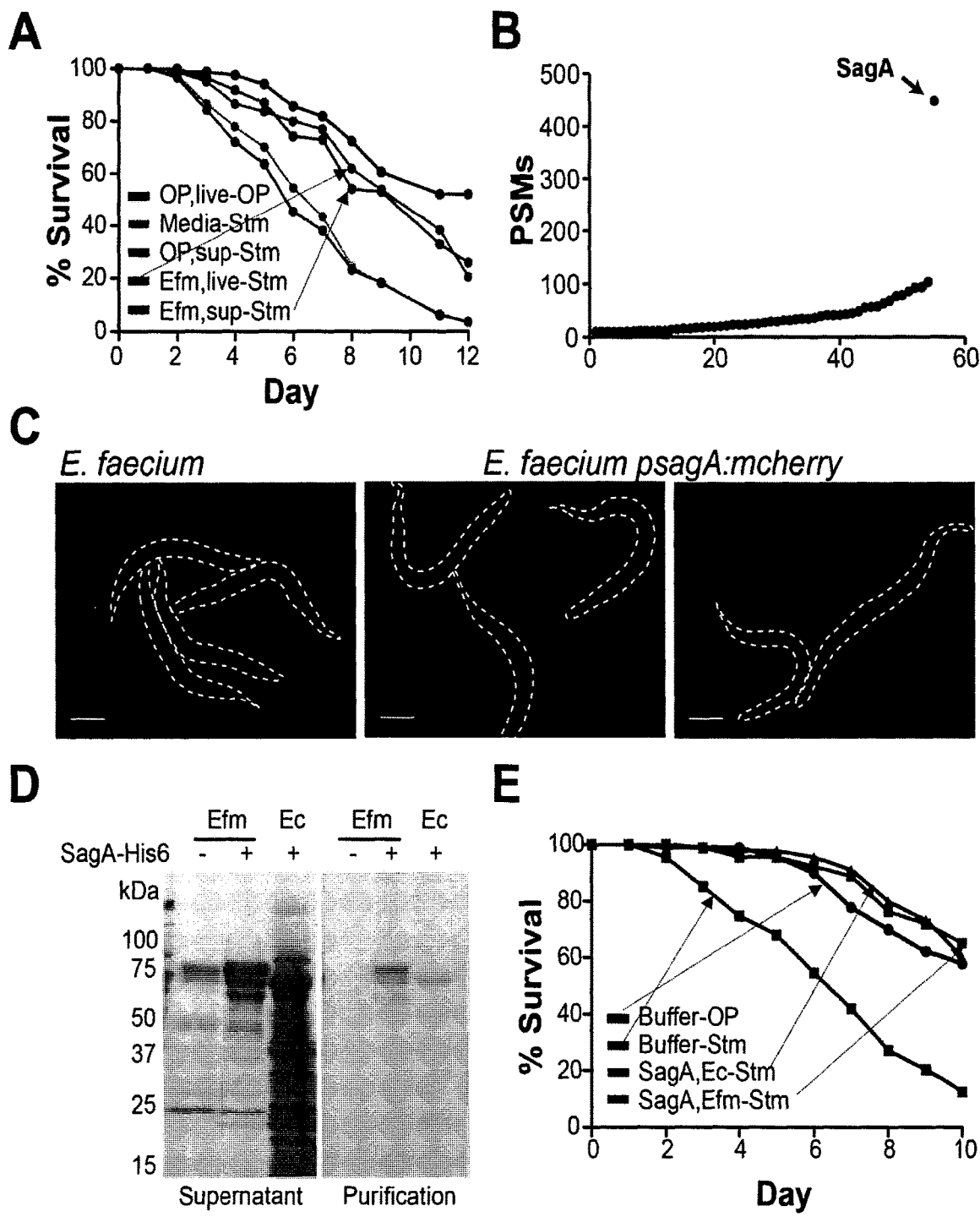
FIG. 2. *E. faecium* SagA is sufficient for inducing host resistance to *S. Typhimurium*. (A) Survival curve showing that both *E. faecium* culture supernatant (Efm, sup) ($p<10^{-6}$) and live *E. faecium* culture (Efm, live) ($p<10^{-7}$) can inhibit *S. Typhimurium*-induced death. OP50 culture supernatant (OP, sup) is not protective (p=1). (B) Summary of proteins identified in *E. faecium* culture supernatant by mass spectrometry with at least 10 peptide spectrum matches (PSMs). Proteins involved in peptidoglycan remodeling are in red. The x-axis represents arbitrary protein number. (C) Fluorescence images of *C. elegans* treated for 1 day with wild-type *E. faecium* or *E. faecium* expressing mcherry under the SagA promoter (psagA:mcherry). The dotted lines indicate an outline of the worm body. Scale bar=200 µm. (D) Coomassie stained SDS-PAGE of culture supernatants and SagA-His$_6$ purifications from *E. faecium* Com15 (Efm) and *E. coli* BL21-RIL(DE3) (Ec). (E) Survival curve showing that SagA-His$_6$ purified from either *E. coli* BL21-RIL(DE3) (SagA, Ec) ($p<10^{-10}$) or *E. faecium* Com15 (SagA, Efm) ($p<10^{-10}$) is sufficient to inhibit *S. Typhimurium* pathogenesis. Abbreviations: *E. coli* OP50 (OP); *S. Typhimurium* (Stm); *E. faecium* (Efm).
Figure 6:
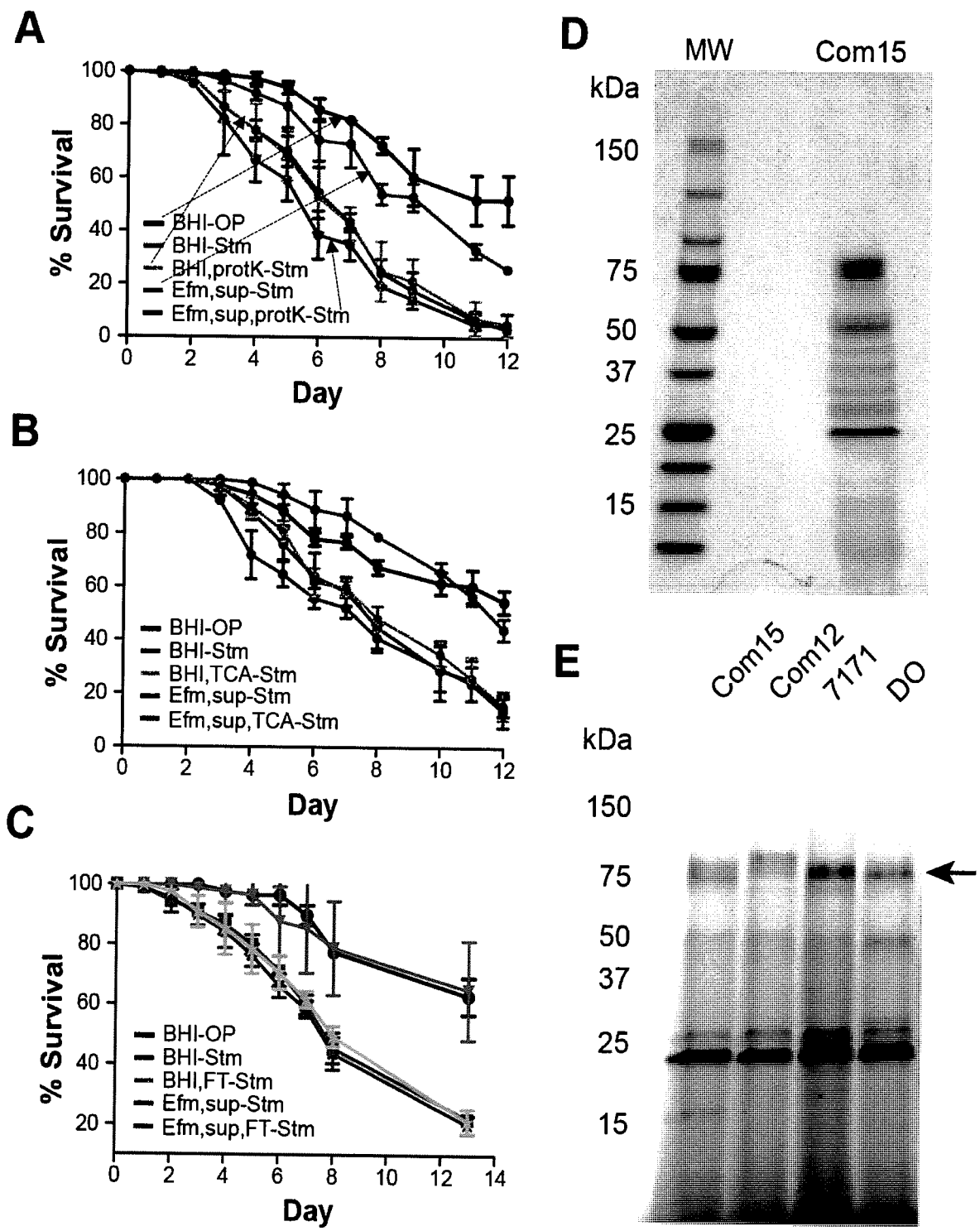
FIG. 6. Protein from *E. faecium* culture supernatant is protective. (A) Proteinase-K-treated *E. faecium* culture supernatant (Efm,sup,protK) loses activity compared to untreated *E. faecium* culture supernatant (Efm,sup). Untreated media (BHI) and proteinase-K-treated media (BHI,protK) are inactive. (B) Trichloroacetic acid (TCA) precipitated *E. faecium* culture supernatant (Efm,sup,TCA) loses activity. Untreated media (BHI) and TCA precipitated media (BHI,TCA) are inactive. (C) 10 kDa MWCO column filtered *E. faecium* culture supernatant (Efm,sup,FT) is inactive. Untreated media (BHI) and 10 kDa MWCO column filtered media (BHI,FT) are inactive. (D) Coomassie stained SDS-PAGE of *E. faecium* Com15 culture supernatant subsequently digested for mass spectrometry analysis presented in Table 1 and FIG. 2B. (E) Stain-free imaging of *E. faecium* culture supernatants from various *E. faecium* strains separated by SDS-PAGE. Arrow indicates protein band corresponding to typical SagA migration. For (A) through (C), data points represent mean±s.d. for 3 plates of 30 worms each. Abbreviations: E. coli OP50 (OP); S. typhimurium (Stm); E. faecium (Efm).
Figure 7:
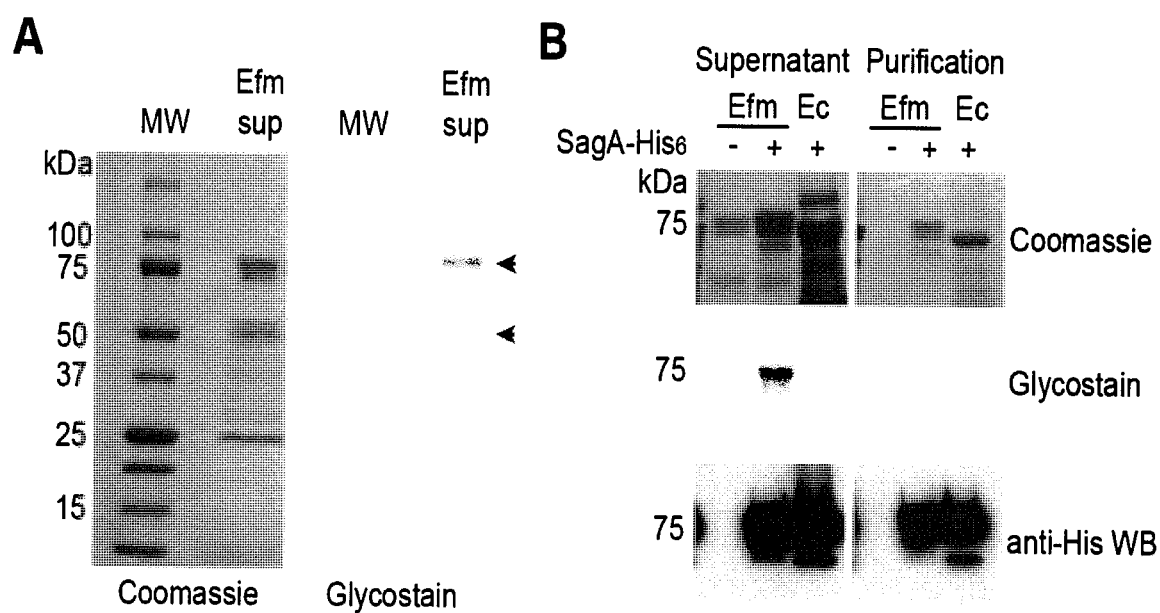
FIG. 7. Characterization of SagA from E. faecium and E. coli. (A) Coomassie staining and glycoprotein-staining of E. faecium Com15 culture supernatant. The arrows indicate protein bands excised for mass spectrometry analysis presented in Table 2. The blue arrow indicates a protein band corresponding to typical SagA migration. (B) SDS-PAGE of culture supernatants and SagA-His$_6$ purifications from E. faecium Com15 (Efm) and E. coli BL21-RIL(DE3) (Ec). Samples were visualized by Coomassie staining, glycoprotein-staining, and anti-His$_6$ Western blot (WB) as indicated. SagA is glycosylated in E. faecium but not E. coli.

We next explored whether specific factors produced by *E. faecium* were sufficient for protection against *S. Typhimurium* pathogenesis. Using a liquid-treatment infection assay (FIG. 1A), we found that *E. faecium* culture supernatant was as effective as live bacterial cultures in inhibiting *S. Typhimurium* pathogenesis (FIG. 2A). Activity of the *E. faecium* supernatant was sensitive to proteinase-K treatment, trichloro-acetic acid precipitation, and 10-kDa size exclusion (FIG. 6A-C), leading us to analyze the protein composition of *E. faecium* culture supernatant by mass spectrometry (FIG. 6D-E, Table 1). Proteomic analysis of *E. faecium* culture supernatant revealed a number of secreted proteins and an enrichment of peptidoglycan remodeling factors (FIG. 2B). We focused on secreted antigen A (SagA), the most abundant protein identified in the supernatant (FIG. 2B), which encodes a putative secreted N1pC/p60 peptidoglycan hydrolase that is believed to be essential for *E. faecium* viability. Fluorescence imaging of animals treated with *E. faecium*-expressing mCherry under the sagA promoter (psagA:mcherry) indicates that SagA is expressed by *E. faecium* during *C. elegans* colonization (FIG. 2C). To test the protective activity of SagA in *C. elegans* directly, we expressed and purified recombinant SagA-His$_6$ from both *E. coli* BL21-RIL(DE3) and *E. faecium* Com15 (FIG. 2D and FIG. 7A-B; Table 2). Remarkably, treatment of animals with SagA-His$_6$ purified from the culture supernatant of either source was sufficient to inhibit *S. Typhimurium* pathogenesis (FIG. 2E and FIG. 7C).

Figure 3:
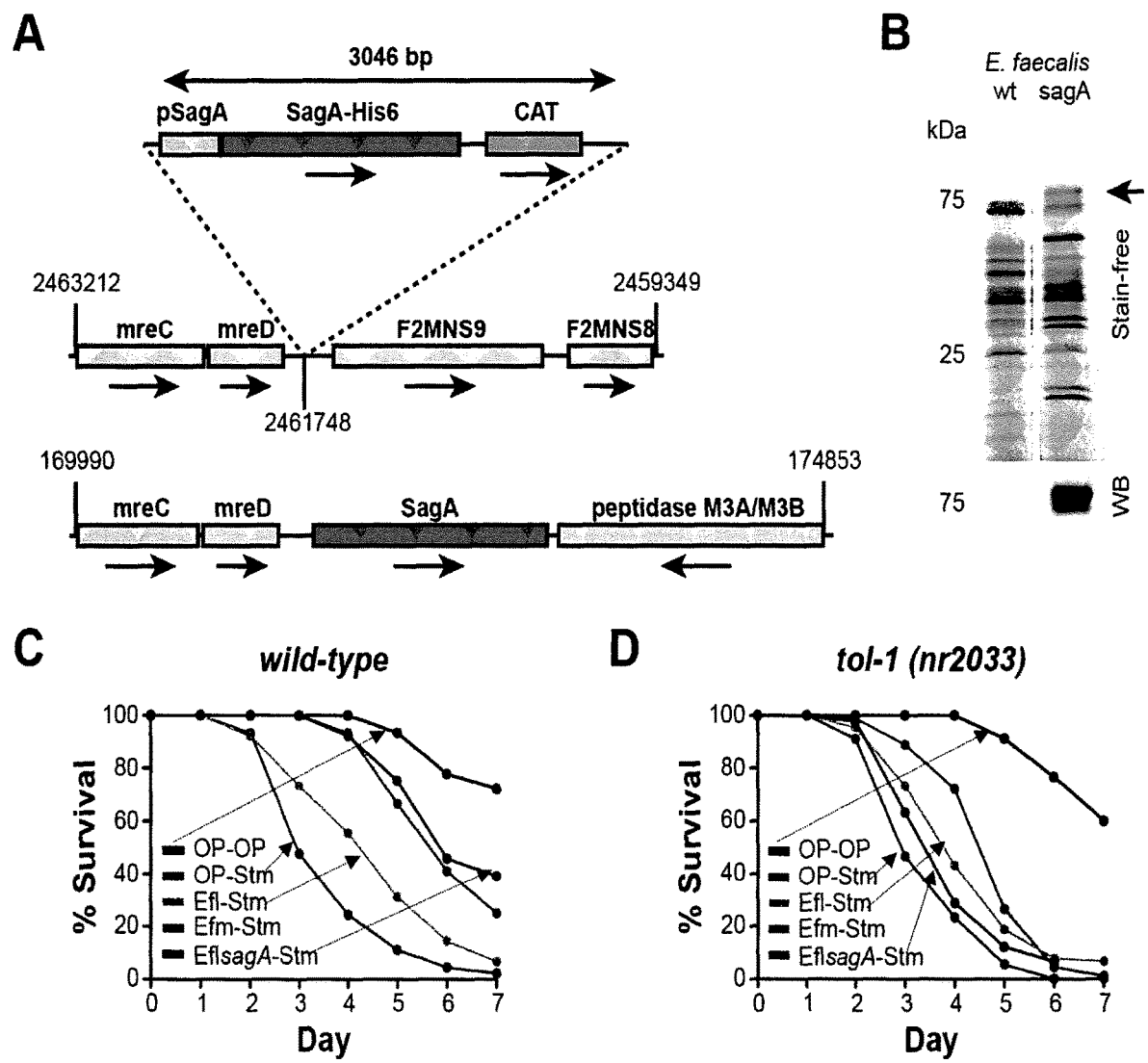
FIG. 3. *E. faecium*-SagA protection is conserved, transferable to other bacteria and requires to tol-4 signaling. (A) Schematic showing insertion of SagA-His$_6$ into the *E. faecalis* OG1RF chromosome to generate *E. faecalis*-sagA. CAT=chloramphenicol resistance gene. For comparison, a schematic of the SagA locus in *E. faecium* Com15 is shown underneath. (B) Stain-free imaging and anti-His$_6$ Western blot (WB) of *E. faecalis* and *E. faecalis*-sagA culture supernatants. Arrow indicates protein band corresponding to SagA mobility in SDS-PAGE. (C) Survival curve from a continuous infection assay showing that *E. faecalis*-sagA inhibits *Salmonella* pathogenesis ($p<10^{-10}$) similarly to *E. faecium* (p=1). (D) Survival curve from a continuous infection assay showing that *E. faecalis*-sagA (p=0.053) does not inhibit *S. Typhimurium* pathogenesis in tol-1(nr2033). Abbreviations: *E. coli* OP50 (OP); *B. subtilis* (Bs); *S. Typhimurium* (Stm); *E. faecium* (Efm), *E. faecalis* (Efl).
Figure 8:
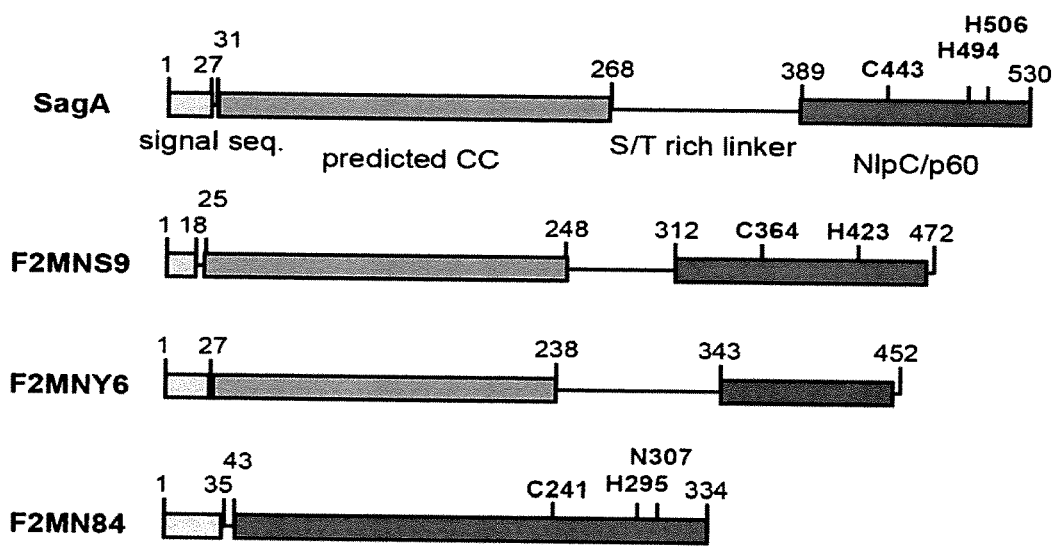
FIG. 8. Secretome profiling of E. faecium, E. faecalis, and E. faecalis-sagA. (A) Predicted domain architecture of three proteins in the E. faecalis OG1RF genome with significant alignment to SagA. By Needleman-Wunsch global alignment, F2MNS9 has 35.1% sequence identity and 50.6% sequence similarity to SagA; F2MNY6 has 35.6% identity and 54.5% similarity, and F2MN84 has 14.5% identity and 24.2% similarity. Amino acid number is as indicated, and putative catalytic residues are indicated in red bold type. F2MNY6 lacks any putative catalytic residues in its N1pC/p60 like domain, and F2MN84 lacks a predicted coiled-coil domain. As indicated in FIG. 9A, both SagA and F2MNS9 are located after the mreCD operon in the chromosome. (B) Stain-free imaging and anti-His$_6$ Western blot (WB) of culture supernatants from E. faecium Com15 (Efm), E. faecalis OG1RF (Efl), and E. faecalis-sagA (EflsagA). Parallel samples were trypsin digested in-solution for mass spectrometry analysis presented in (B) through (E), and Tables 3 and 4. (C) Summary of proteins identified by mass spectrometry from E. faecalis OG1RF culture supernatant. Proteins shown were identified with at least 2 unique peptides. Proteins involved in cell-wall remodeling are highlighted in red; on the y-axis is peptide spectrum matches (PSMs); on the x-axis is arbitrary protein number. For the list of proteins identified, see Table 3. (D) Summary of proteins identified by mass spectrometry from E. faecalis-sagA culture supernatant. Proteins shown were identified with at least 2 unique peptides. Proteins involved in cell-wall remodeling are highlighted in red. For the list of proteins identified, see Table 4. (E) Summary of proteins identified by mass spectrometry from E. faecium Com15 culture supernatant. Proteins shown were identified with at least 2 unique peptides. Proteins involved in cell-wall remodeling are highlighted in red. For the list of proteins identified, see Table 5. (F) Venn diagram comparing the proteins identified by mass spectrometry after in-gel trypsin digestion (blue) (See FIG. 2B, Table 1) versus in-solution trypsin digestion (red) (See FIG. 9E, Table 4). Proteins identified in both samples are indicated in the overlap (grey). Proteins included in this graph were identified with at least 2 unique peptides, and at least 10 PSMs.
Figure 8:
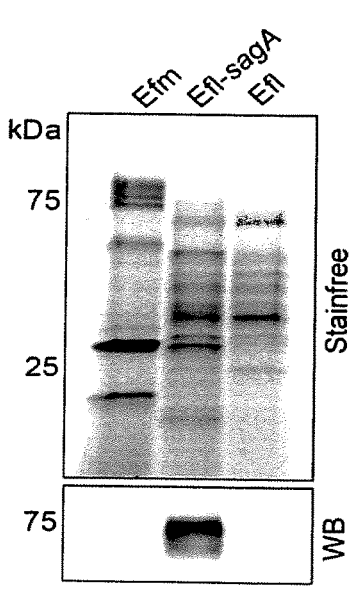
Figure 8:
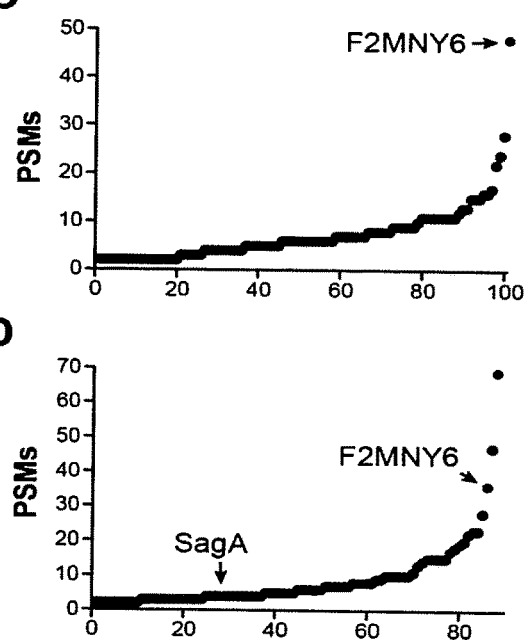
Figure 8:
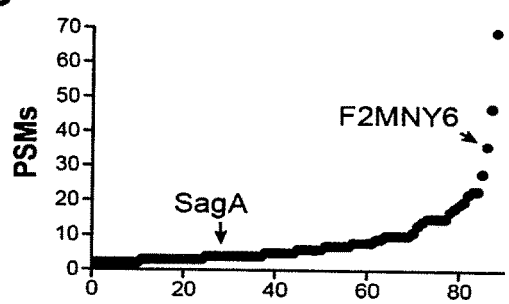
Figure 8:
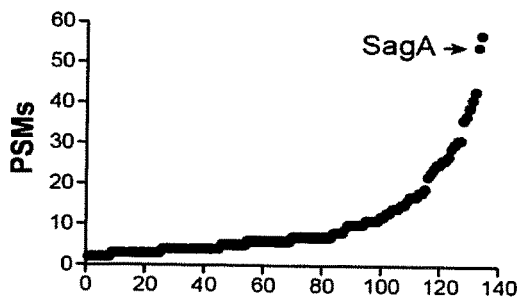
Figure 8:
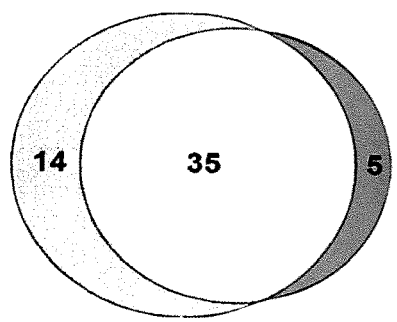
Figure 9:
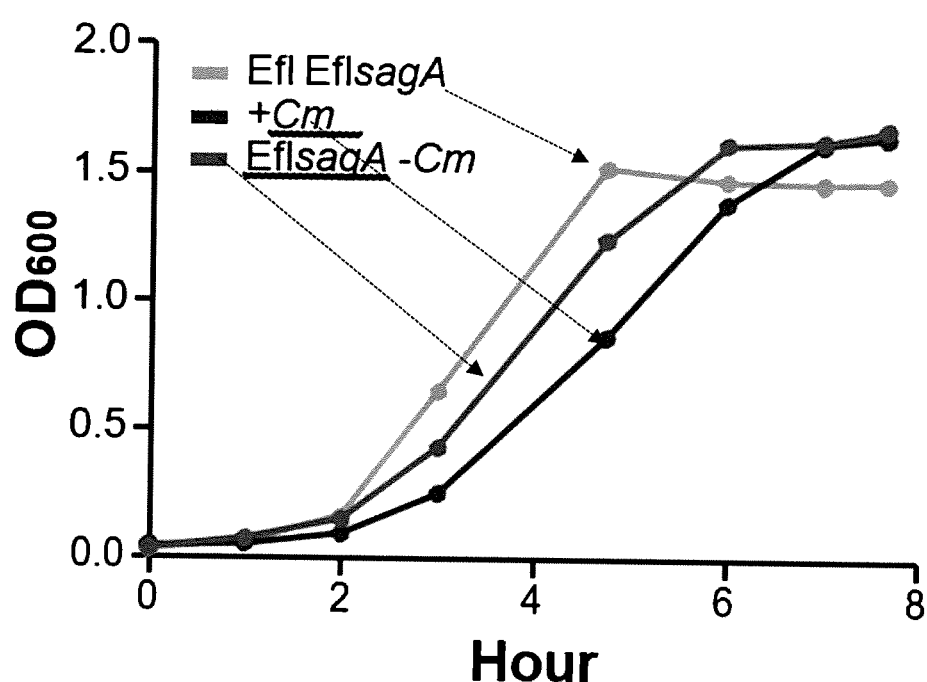
FIG. 9. Growth rate of E. faecalis-sagA. Growth curves of E. faecalis (Efl) and E. faecalis-sagA (EflsagA). Cm+ and Cm− indicate ±10 µg/mL chloramphenicol.
Figure 10:
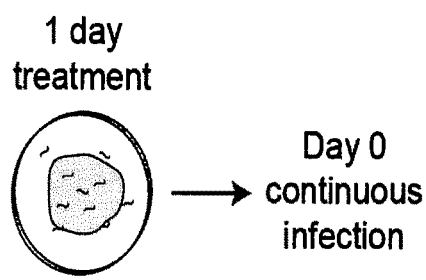
FIG. 10. Characterization of E. faecalis-sagA. (A) Schematic of a treatment-continuous Salmonella infection assay. Animals were treated for 1 day on BHI agar with E. faecium, E. faecalis, or E. faecalis-sagA, then transferred to NGM agar plates for infection with Salmonella for the remainder of the assay and survival was scored. Control animals were fed E. coli OP50 throughout the assay. (B) Salmonella and Enterococcus CFUs measured in C. elegans throughout the continuous infection assay. Data points represent average CFUs from 5 worms±standard deviation of two independent experiments. The dotted line indicates detection limit. The background shading indicates stages of the treatment-continuous infection. Green indicates treatment and red indicates infection. (C) Survival curve showing that E. faecalis-sagA is less pathogenic than E. faecalis in a continuous E. faecalis infection assay. Data points represent mean±standard deviation for 3 plates of 30 worms each. Abbreviations: E. coli OP50 (OP); S. typhimurium (Stm); E. faecium (Efm); E. faecalis (Efl); E. faecalis-sagA (EflsagA).
Figure 10:
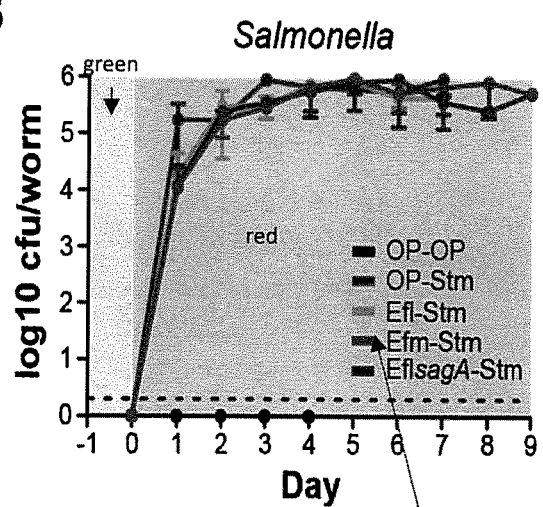
Figure 10:
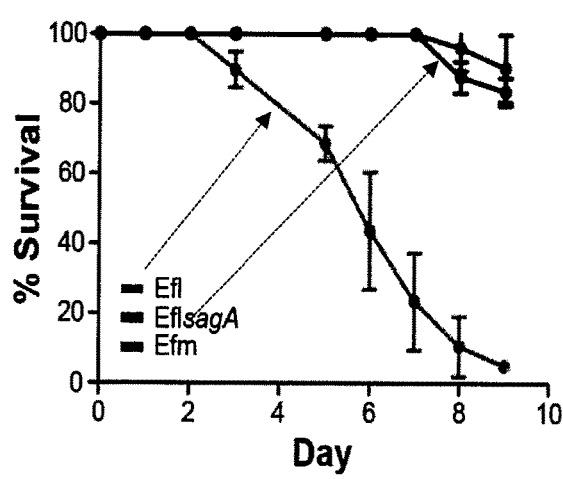
Figure 10:
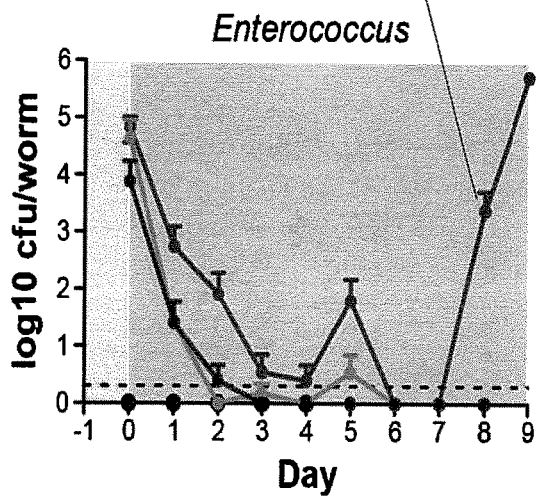

Analysis of sequenced *E. faecium* strains suggests they all encode a sagA ortholog in their genomes. In contrast, sequenced *E. faecalis* strains do not encode a clear sagA ortholog in their genomes and have not been reported to inhibit *S. Typhimurium* pathogenesis. For example, *E. faecalis* OG1RF encodes three putative N1pC/p60-type peptidoglycan hydrolases (Uniprot accession: F2MNS9, F2MN84, F2MNY6) with less than 40 percent protein sequence identity to SagA (FIG. 8A). F2MNS9 and F2MN84 are predicted N1pC/p60-type hydrolases, whereas F2MNY6 lacks the conserved amino acid residues predicted for catalytic activity (FIG. 8A). To determine if sagA expression is sufficient to confer protective activity, we inserted sagA-his$_6$ into the chromosome of *E. faecalis* OG1RF to generate *E. faecalis*-sagA (FIG. 3A). In culture, SagA-His$_6$ was expressed and secreted by *E. faecalis*-sagA (FIG. 3B), marginally affecting bacterial growth (FIG. 9). Proteomic analysis of *E. faecalis* OG1RF, *E. faecalis*-sagA, and *E. faecium* culture supernatants revealed less relative secreted SagA in *E. faecalis*-sagA culture supernatant as compared to *E. faecium* culture supernatant (FIG. 8B-F; Tables 3, 4). We detected only F2MNY6 in *E. faecalis* OG1RF culture supernatant (FIG. 9C), suggesting that, unlike *E. faecium*, *E. faecalis* does not secrete high levels of active N1pC/p60-type peptidoglycan hydrolases. In a continuous infection assay (FIG. 10A), treatment of *C. elegans* with *E. faecalis*-sagA attenuated *S. Typhimurium* pathogenesis comparably to *E. faecium*, while treatment with wild-type *E. faecalis* was not protective (FIG. 3C). *S. Typhimurium* load was similar in animals across all infected conditions, indicating that treatment with *E. faecalis*-sagA does not inhibit *S. Typhimurium* colonization or replication in vivo (FIG. 10B). In addition, SagA expression also counteracted the intrinsic pathogenesis of *E. faecalis* OG1RF (8) (FIG. 10C). These results demonstrate that the protective activity conferred by sagA expression is transferable to other bacterial species.

Figure 11:
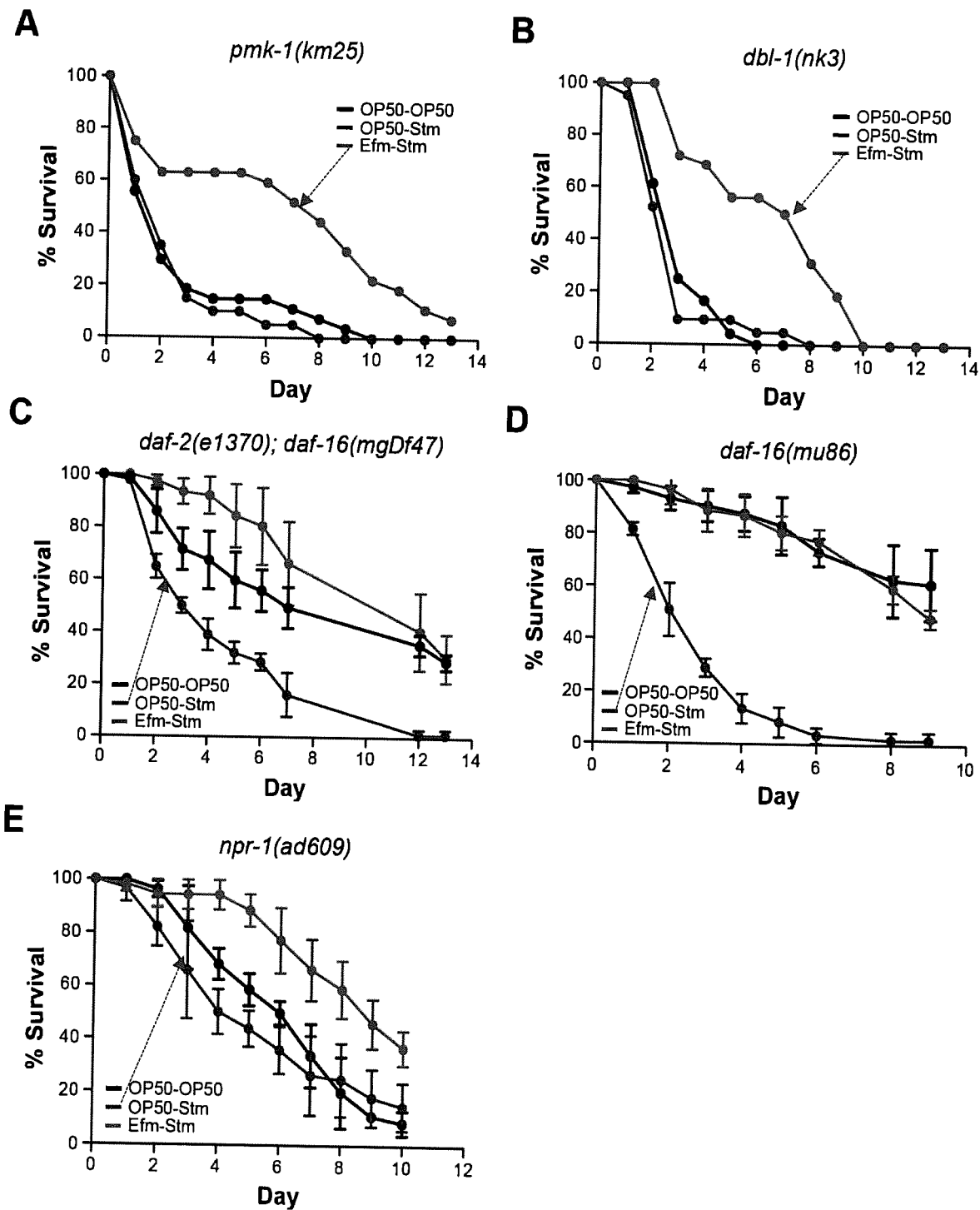
FIG. 11. E. faecium protection in C. elegans mutants. Survival curves assaying E. faecium-mediated protection in (A) pmk-1(km25) (B) dbl-1(nk3) (C) daf-2(e1370);daf-16 (mgDf47) (D) daf-16(mu86) and (E) npr-1(ad609). For survival curves with error bars, each condition was tested with 3 plates of 30 worms each, and data points represent mean±standard deviation. For curves without error bars, each condition was tested with one plate of 30 worms. Abbreviations: E. coli OP50 (OP); S. typhimurium (Stm); E. faecium (Efm).

The protective activity of *E. faecium* against multiple enteric pathogens indicated that SagA may engage host pathways to limit pathogenesis. In response to intestinal infection, *C. elegans* mounts both general and pathogen-specific immune responses, which can lead to behavioral changes as well as the expression of antimicrobial and stress response effectors. The *C. elegans* innate immune system comprises both constitutive and induced signaling pathways, many with homology to mammalian pathways. Literature regarding *C. elegans* immunity-associated mutants indicates no major roles for the p38 MAPK/Pmk-1 pathway, the TGF-β-like/Db1-1 pathway, the insulin-like receptor/Daf-2 pathway, or the Npr-1 mediated pathogen avoidance pathway in *E. faecium*-mediated protection against *S. Typhimurium* infection (FIG. 11). *C. elegans* encodes one predicted homologue of Toll-like receptor, to tol-1 (N. Pujol et al., A reverse genetic analysis of components of the Toll signaling pathway in *Caenorhabditis elegans*. Curr Biol 11, 809 (Jun. 5, 2001)). Although tol-1 is important for development, *C. elegans* lacking the tol-1 TIR signaling domain [tol-1 (nr2033)] are viable but exhibit defective pathogen avoidance to *S. marsescens* and an increased susceptibility to *S. Typhimurium* infection. We assessed SagA-mediated protection against *S. Typhimurium* pathogenesis in tol-1(nr2033) animals and found that both *E. faecium* and *E. faecalis*-sagA were not protective against continuous *S. Typhimurium* infection in this mutant background, suggesting that tol-1 signaling is required for SagA-mediated host protection (FIG. 3D). Without intending to be constrained by any particular theory, these results suggest SagA activates innate immune signaling pathways to enhance host resistance to enteric pathogens.

Figure 4:
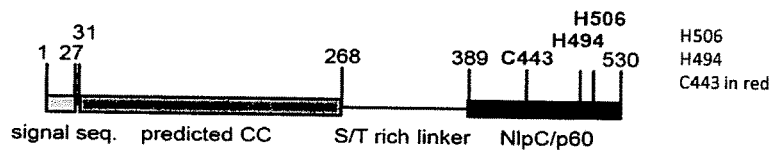
FIG. 4. Enzymatic activity of SagA is required for inducing host resistance through Tot-1 signaling. (A) Schematic of SagA domain organization. The signal sequence is yellow, the predicted coiled-coil (CC) domain is orange, and the N1pC/p60 type hydrolase domain is blue. Active site residues in the hydrolase domain are in red type. Amino acid number is as indicated. (B) Survival curve showing that SagA inhibits *S. Typhimurium* pathogenesis ($p<10^{-10}$) while an active site mutant (AS) and C-terminal truncation mutant (Ctrunc) do not (p=0.42 and 0.98 respectively). (C) OD600 of *E. coli* BL21-RIL(DE3) expressing SagA, the active site mutant, or SagA-SS under an IPTG-inducible promoter. Measurements were taken 1 hour post-induction and normalized to the OD600 of a mock-induced non-expressing BL21-RIL(DE3) culture. Bars represent mean±s.e.m. from three independent experiments. Significance was calculated by unpaired t test. For **, p<0.01. (D) Survival curve showing that 5-kDa MWCO column filtered *E. coli* culture supernatants expressing SagA-His$_6$ (Ec, sagA-FT) inhibit *S. Typhimurium* pathogenesis ($p<10^{-4}$), while filtered *E. coli* culture supernatants expressing the active site mutant (Ec, AS-FT) do not (p=1). (E) Survival curve showing that purified *E. coli* peptidoglycan treated with SagA (PG, SagA) can inhibit *S. Typhimurium* pathogenesis ($p<10^{-10}$), while *E. coli* peptidoglycan treated with the active site mutant (PG, AS) cannot (p=1). (F) ANTS visualization of *E. coli* culture supernatants expressing SagA-His$_6$ or the active site mutant. Samples were filtered through 10-kDa MWCO columns, dried, ANTS labeled, separated by native PAGE, then visualized by UV. ANTS-labeled synthetic fragments MDP, GlcNAc, MurNAc, and MurNAc-L-Ala were run for comparison. A sugar-less pentapeptide (Ala-D-Glu-Lys-Ala-Ala (PP)) was run to show specificity of the UV signal. (G) ANTS visualization of peptidoglycan fragments in *E. faecium* (Com15), *E. faecium*-sagA (Com15 transformed with SagA expression plasmid), *E. faecalis* (OG1RF), and *E. faecalis*-sagA culture supernatants. (H) Survival curves showing that treatment with MurNAc ($p<10^{-5}$) or MurNAc-L-Ala ($p<10^{-10}$) can inhibit *S. Typhimurium* pathogenesis, while MDP (p=1) and GlcNAc (p=1) are not protective. (I) Survival curve showing that MurNAc (p=1) and MurNAc-Ala (p=0.61) do not inhibit *S. Typhimurium* pathogenesis in tol-1(nr2033) animals. Abbreviations: *E. coli* OP50 (OP); *S. Typhimurium* (Stm).
Figure 4:
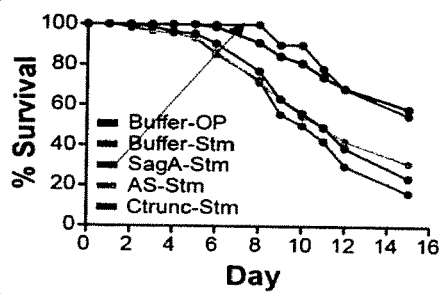
Figure 4:
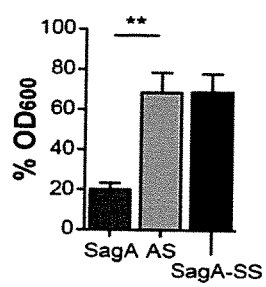
Figure 4:
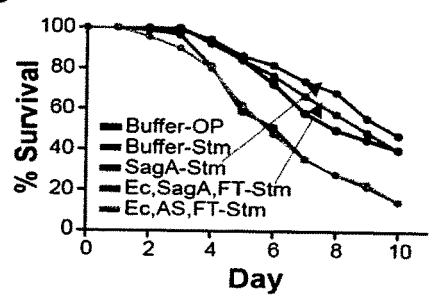
Figure 4:
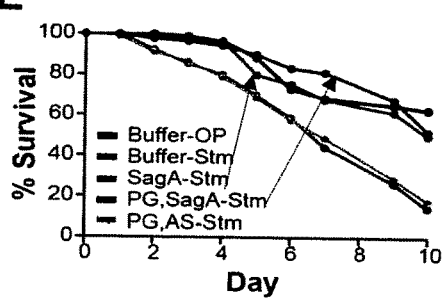
Figure 4:
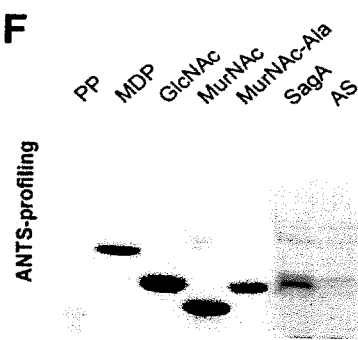
Figure 4:
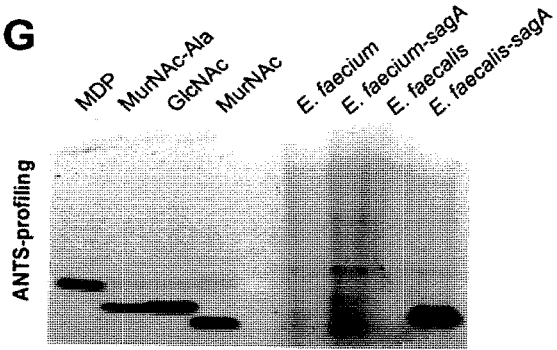
Figure 4:
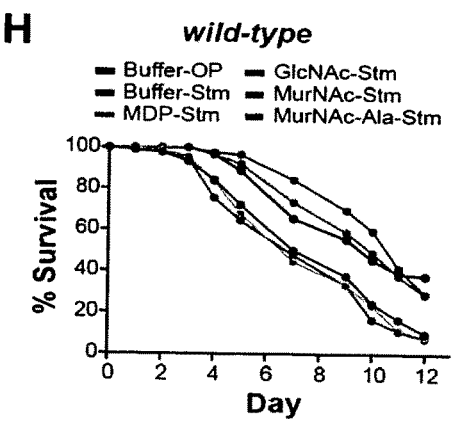
Figure 4:
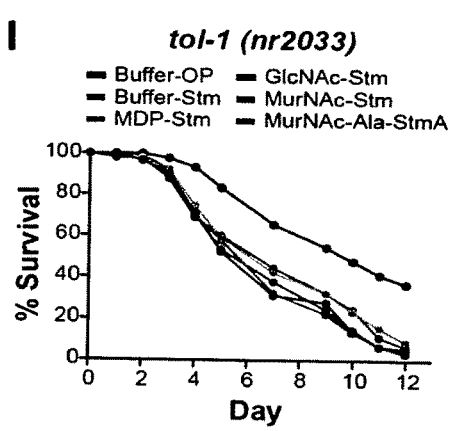

To determine the mechanism by which SagA enhances host resistance, we evaluated the N1pC/p60 hydrolase activity of SagA. SagA contains a type-1 signal sequence, an uncharacterized N-terminal coiled-coil domain, a linker region of Ser/Thr-rich repeats, and a C-terminal N1pC/p60-type hydrolase domain (M. Firczuk, M. Bochtler, Folds and activities of peptidoglycan amidases. *FEMS Microbiol Rev* 31, 676 (November, 2007)); (FIG. 4A).

Figure 12:
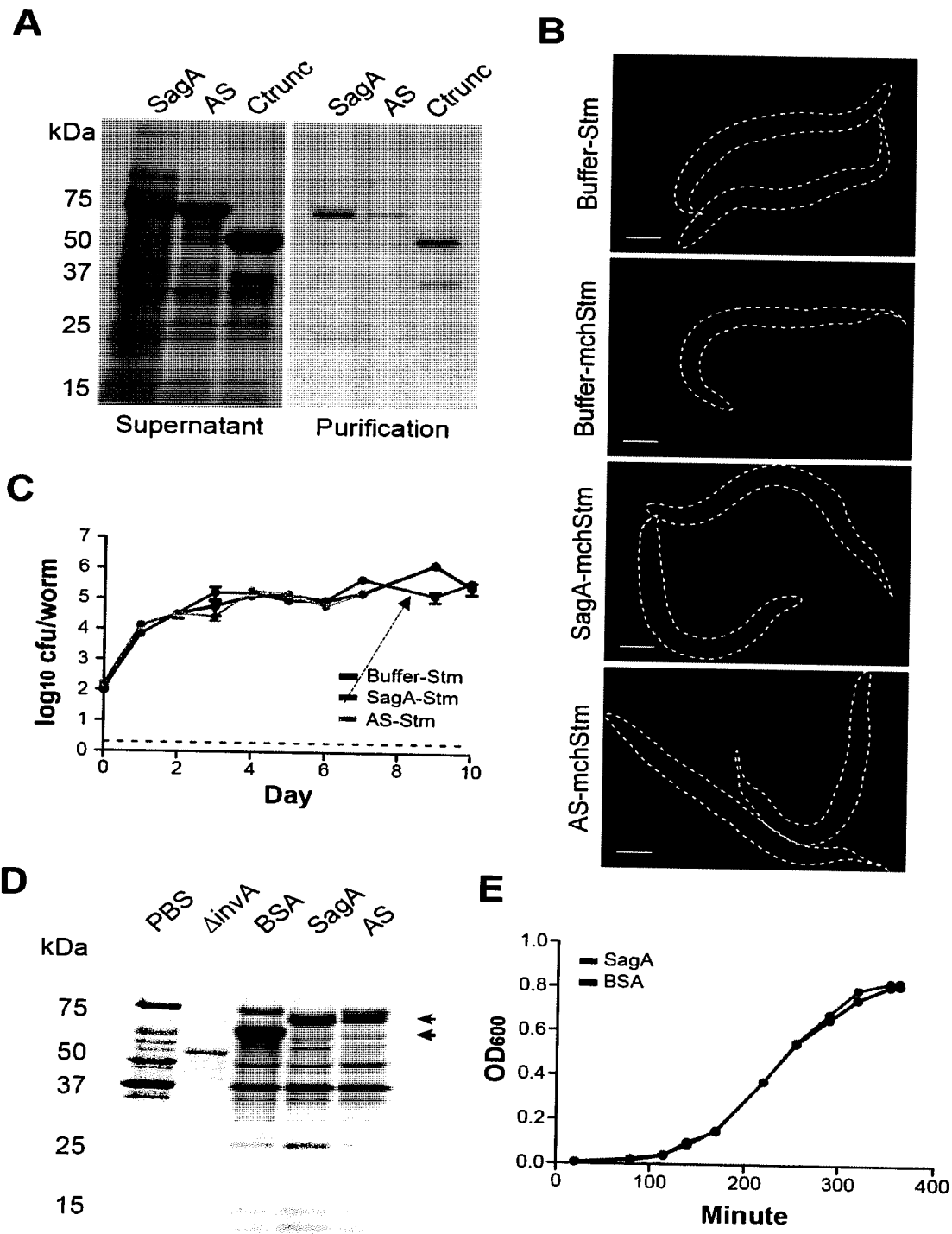
FIG. 12. SagA does not affect SPI-1 type III protein secretion in S. typhimurium. (A) Fluorescence imaging of C. elegans treated with SagA or the active site mutant, then infected with Salmonella expressing mcherry (mchStm) at day 5 post-infection. The dotted lines indicate an outline of the worm body. Scale bar=200 µm. (B) Salmonella CFUs measured in C. elegans at indicated time points from an average of 10-20 worms±standard deviation. The dotted line indicates detection limit. (C) SagA does not affect SPI-1 secretion in culture. Salmonella cultures were grown in LB+10 µg/ml BSA, SagA, or the active site mutant. PBS indicates control treatment. ΔinvA is a Salmonella mutant that does not secrete effectors in culture. (D) Growth curves of Salmonella in LB media+10 µg/ml SagA or BSA. Abbreviations: E. coli OP50 (OP); S. typhimurium (Stm).
Figure 13:
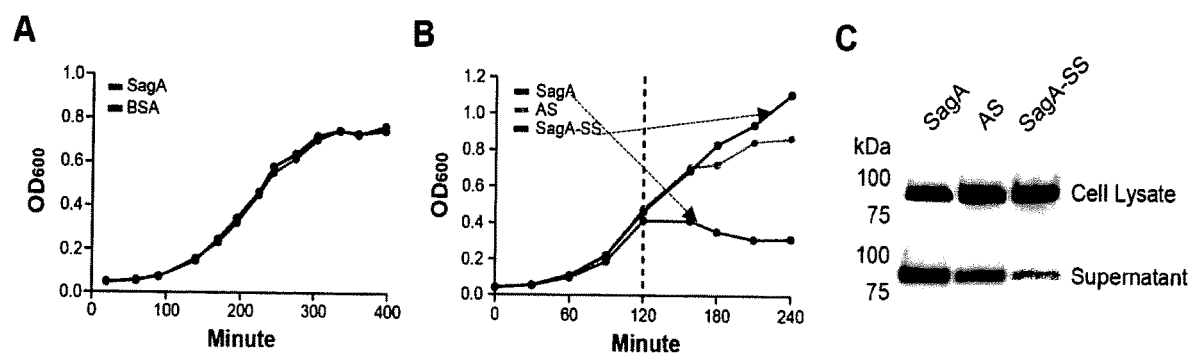
FIG. 13. Characterization of SagA enzymatic activity in E. coli. (A) Growth curves of E. coli BL21-RIL(DE3) in LB media+10 µg/ml SagA or BSA. (B) Growth curves of E. coli BL21-RIL(DE3) expressing SagA, the active site mutant (AS), or SagA lacking a signal sequence (Sag-SS) under an IPTG-inducible promoter. The dotted line indicates time of IPTG induction. (C) anti-His$_6$ Western blots of cell lysate or culture supernatant from E. coli BL21-RIL(DE3) expressing SagA, the active site mutant, or Sag-SS after IPTG induction. SagA-SS is mostly retained in the cell lysates, while SagA and the active site mutant are secreted.

Although SagA is suggested to be essential for *E. faecium* viability, no hydrolase activity has been described. To determine if the N1pC/p60-type hydrolase domain of SagA is required for protection of *C. elegans*, we generated an active site (AS) mutant as well as a C-terminal N1pC/p60-type hydrolase domain deletion (Ctrunc) mutant of SagA (FIG. 4A). Both of these protein constructs were expressed, secreted, and purified from *E. coli* BL21-RIL(DE3) (FIG. 12A). However, neither of these SagA mutants was able to inhibit *S. Typhimurium* pathogenesis, indicating that the N1pC/p60-type hydrolase domain and active site are required for SagA activity (FIG. 4B). Fluorescence imaging of mCherry-*S. Typhimurium* and CFU measurements from untreated, SagA-treated, and active site mutant-treated infected animals were comparable (FIG. 12B-C), indicating that SagA does not affect *S. Typhimurium* colonization of *C. elegans*. In culture, addition of recombinant SagA also had no effect on the growth rate of *S. Typhimurium* (FIG. 12D) or on the secretion of *S. Typhimurium* type III protein effectors (FIG. 12E), suggesting that SagA does not directly attenuate *S. Typhimurium* growth or virulence mechanisms. The addition of recombinant SagA also had no effect on the growth rate of *E. coli* in culture (FIG. 13A). However, induction of SagA expression in *E. coli* led to a decrease in culture optical density (OD) (FIG. 3C, 13B-C), indicating cell lysis. In contrast, expression of the active site mutant or SagA lacking a signal sequence did not induce *E. coli* cell lysis (FIG. 4C and FIG. 13B-C). These data suggest that while SagA is not bacteriolytic when added exogenously, SagA is a functional hydrolase that can cleave peptidoglycan when appropriately targeted to the periplasm. Collectively, these results demonstrate that the N1pC/p60 domain of SagA has hydrolase activity and is required for enhancing host resistance.

Figure 14:
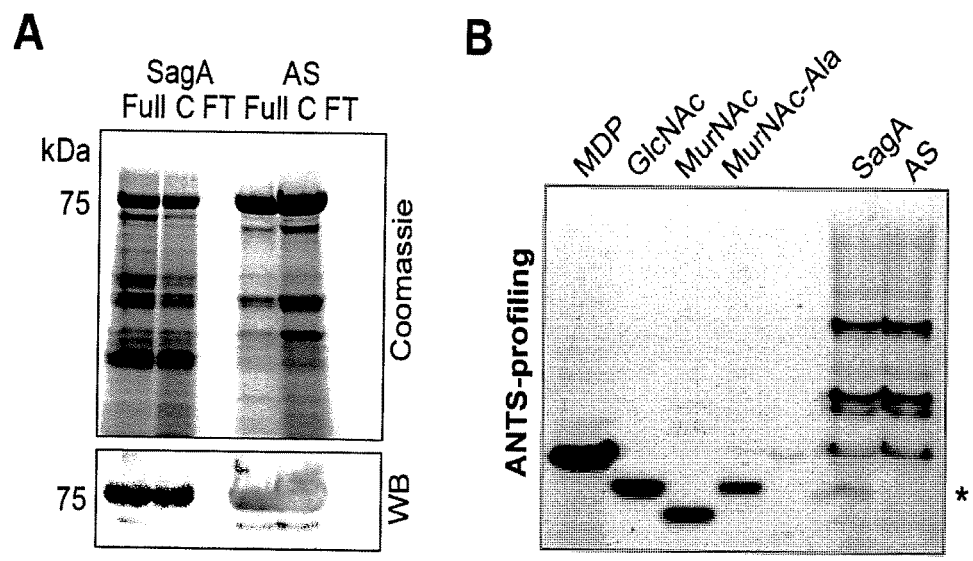
FIG. 14. Characterization of SagA peptidoglycan hydrolases activity. (A) Removal of SagA-His$_6$ from column filtrate. Coomassie staining and anti-His$_6$ WB of E. coli culture supernatants expressing SagA-His$_6$ or the active site mutant. Supernatant was filtered through a 5-kDa MWCO column. Unfiltered supernatant (Full), column concentrate (C), and column flow-through (FT) are as indicated. (B) ANTS visualization of purified E. coli peptidoglycan (PG) digested with lysozyme and either SagA or the active site mutant.

We analyzed whether SagA could hydrolyze peptidoglycan fragments derived from digested bacteria in the *C elegans* intestine, and whether these fragments may be responsible for enhancing host resistance. We found that the flow-thru from 5 kDa-MWCO column-filtered culture supernatants of *E. coli* expressing SagA, but not the active site mutant, protected *C. elegans* from *S. Typhimurium* pathogenesis (FIG. 4D). We confirmed removal of SagA from the column flow-thru by Western blot (FIG. 14A), suggesting that lower molecular weight products of SagA enzymatic activity are sufficient for *C. elegans* protection. To more directly test if SagA-generated *E. coli* peptidoglycan fragments can also protect *C. elegans* from *S. Typhimurium* pathogenesis, we digested purified *E. coli* peptidoglycan with lysozyme and either SagA or the active site mutant, then filtered the digests to exclude protein.

*C. elegans* treated with the SagA peptidoglycan digests survived similarly to SagA-treated animals, whereas active site mutant digests failed to attenuate *S. Typhimurium* pathogenesis (FIG. 4E). These results suggest that SagA-generated peptidoglycan fragments, and not SagA itself, are responsible for protecting *C. elegans* from *S. Typhimurium* pathogenesis.

To identify the peptidoglycan fragment(s) generated by SagA, we analyzed filtered bacterial culture supernatants by ANTS labeling and gel-based profiling using established techniques. From *E. coli* expressing SagA, we detected a SagA-specific ANTS-labeled product that migrated similarly to the ANTS-labeled synthetic peptidoglycan components MurNAc-L-Ala and GlcNAc, but not to MurNAc-L-Ala-D-Glu (MDP) or MurNAc (FIG. 4F). Analysis of *E. faecium* and *E. faecalis* culture supernatants revealed *E. faecalis*-sagA generates an ANTS-labeled product that co-migrates with MurNAc (FIG. 4G). In contrast, 10 kDa-MWCO filtered *E. faecium* culture supernatant did not yield detectable levels of MurNAc-L-Ala or MurNAc (FIG. 4G) and was not protective when administered to *C. elegans* (FIG. 6C). However, SagA is secreted at high levels by *E. faecium* (FIG. 2C and FIG. 8) and may hydrolyze intestinal peptidoglycan fragments in trans. Indeed, digestion of purified *E. coli* peptidoglycan with lysozyme and SagA, but not the active site mutant, yielded a unique peptidoglycan cleavage product with similar mobility to MurNAc-L-Ala (FIG. 14B), confirming that secreted SagA can cleave peptidoglycan fragments in trans through its N1pC/p60-type hydrolase activity. We next assessed the activity of MurNAc-L-Ala, GlcNAc, MDP and MurNAc in protecting *C. elegans* from *S. Typhimurium* pathogenesis. While treatment of *C. elegans* with 50 μM of MDP or GlcNAc did not inhibit *S. Typhimurium* pathogenesis, treatment with either MurNAc or MurNAc-L-Ala was sufficient to inhibit *S. Typhimurium* pathogenesis (FIG. 4H). MurNAc and MurNAc-L-Ala were not protective in to1-1(nr2033) animals (FIG. 4I), indicating that tol-1 signaling is required for mediating host protection in response to these peptidoglycan fragments. These data are consistent with peptidoglycan fragments activating innate immunity in mammals, but show MurNAc-L-Ala and MurNAc are the minimal peptidoglycan components that can enhance host resistance in *C. elegans* through a tol-1-dependent pathway. Nonetheless, a more complex mixture of peptidoglycan fragments is likely required in mammals, as MurNAc alone is insufficient to protect antibiotic-treatment mice from *S. Typhimurium* pathogenesis.

Figure 15:
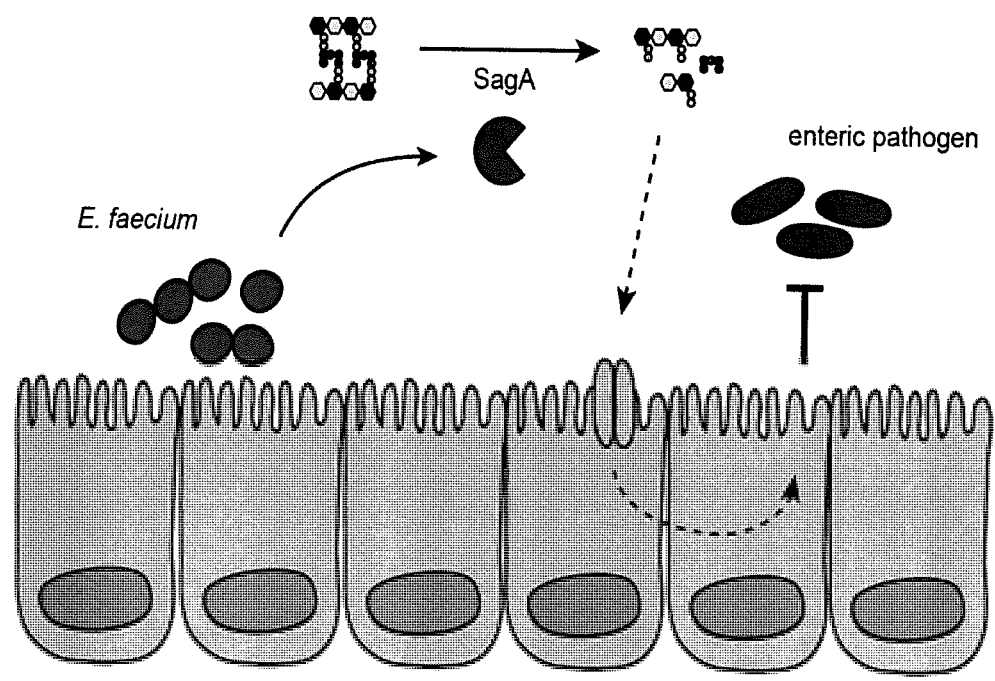
FIG. 15. Model of SagA protective activity. E. faecium (green cocci) secretes SagA (blue pac-man) in the intestinal lumen. SagA hydrolyzes E. coli peptidoglycan (PG) into smaller fragments. SagA-generated PG fragments stimulate an immune response that leads to the inhibition of intestinal pathogenesis (red bacilli). The dashed arrows indicate processes require tol-1 in C. elegans.

It will be recognized from the foregoing that the N1pC/p60 hydrolase activity of SagA generates unique peptidoglycan fragments in vivo that activate host immune signaling to enhance epithelial barrier integrity and confine pathogens to the intestinal lumen (FIG. 1E), ultimately promoting host resistance to disease (FIG. 15). The analysis of *E. faecium* in mice suggests its colonization also improves intestinal epithelial barrier integrity to limit *S. Typhimurium* pathogenesis in mammals. The protective activity of *E. faecium* in mice is mediated by SagA expression and without intending to be bound by any particular theory is believed to require the TLR signaling adaptor MyD88, the peptidoglycan pattern recognition receptor NOD2 and the C-type lectin RegIIIγ. These results together indicate that *E. faecium* and SagA may function through evolutionarily conserved pathways to enhance epithelial barrier integrity and protect animals from enteric pathogens. This Example also reveals a previously unappreciated mechanism for secreted N1pC/p60-type peptidoglycan hydrolases and supports the use of these enzymes to enhance the protective activity of existing probiotics. The following materials and methods were used to obtain the results discussed in this Example.

Materials and Methods.

Strains. *C. elegans* were maintained as described (I). *C. elegans* strains npr-1(ad609), daf-16(mu86), daf-2(e1370); daf-16(mgDf47), pmk-1(km25), dbl-1(nk3), and tol-1 (nr2033) were all provided by the *Caenorhabditis* Genetics Center. *E. coli* OP50, *E. coli* DH5α, *E. coli* BL21-RIL(DE3) (Agilent Technologies), and *Salmonella enterica* serovar *Typhimurium* strain IR715 were grown in LB (BD Difco). *Enterococcus faecium* strains NCTC 7171 (ATCC 19434), Com15, Com12, and TX0016 (DO, ATCC BAA-472), *Enterococcus faecalis* strains OG1RF (ATCC 47077) and V583 (ATCC 700802), and *Bacillus subtilis* strain 168 were grown in BHI (BD BBL). When necessary, ampicillin was used at 100 µg/mL, gentamicin was used at 125 µg/mL, and chloramphenicol was used at 25 µg/mL for *E. coli*, 10 µg/mL for *E. faecium*, and 8 µg/mL for *E. faecalis*.

Plasmids Described in This Study.

SagA hydrolase domain prediction was determined using Phyre 2 software. Coiled coil domain prediction were determined using COILS software. Signal sequence prediction was determined using SignalP v4.1 software.

| Name | Backbone | Description |
|---|---|---|
| pET21a-SagA | pET21a (Novagen) | $Amp^R$, SagA-$His_6$ |
| pET21a-AS | pET21a | $Amp^R$, AS-$His_6$; C443A, H494A, H506A |
| pET21a-ΔCterm | pET21a | $Amp^R$, ΔCterm-$His_6$; Δ390-529 |
| pET21a-SagA-SS | pET21a | $Amp^R$, SagA-SS-$His_6$; Δ2-27 |
| pAM401-SagA | pAM401 (ATCC 37429) | $Cam^R$, psagA:SagA-$His_6$ |
| pAM401-psagA:mcherry | pAM401 | $Cam^R$, psagA:mcherry |
| pTEX5501ts-OG1RF-sagA | pTEXC5501ts | $Cam^R$, $Gen^R$, *see below |
| p67MC1 | | $Amp^R$, mcherry |

Cloning strategies: All cloning was done in *E. coli* DH5α. pET21a constructs were transformed into *E. coli* BL21-RIL (DE3) for expression. pAM401 constructs were transformed into *E. faecium* for expression.

pET21a-SagA:

sagA was PCR amplified from the *E. faecium* Com15 genome using the following primers:

FW:
(SEQ ID NO: 2)
GGA*CATATG*AAAAAGAGTTTAATATCAGCAGTAATGG

RV:
(SEQ ID NO: 3)
GGA*CTCGAG*CATGCTGACAGCAAAGTCAGGTGCAAAC

Restriction sites for Nde1 and Xho1 are italicized. The PCR product was gel purified and subcloned into pGEMTeasy (Promega) for sequencing. Then, an internal Nde1 site was mutated using the Quikchange multi-site directed mutagenesis kit (Stratagene) using the following primer:

(SEQ ID NO: 4)
AAATATATCGGTACTCCtTATGTTTGGGGCGG

The site mutated is indicated in lowercase, resulting in a synonymous mutation in the SagA protein sequence. sagA was then excised from pGEMTeasy with Nde1 and Xho1 and was ligated into cut pET21a (Novagen).

pET21a-AS: pET21a-SagA was mutagenized with the following primers to generate the indicated cysteine to alanine and histidine to alanine mutations in the SagA protein sequence:

C443A:
(SEQ ID NO: 5)
CCAAGTGGATTTGACgcCTCAGGATTCACACG

H494A:
(SEQ ID NO: 6)
TCACCAGGCGGAACTTACgcCGTAGCGATTGC

H506A:
(SEQ ID NO: 7)
GGAGGACAATATATCgcTGCTCCTCAACCAGG

The mutated sites are indicated in lowercase.

pET21a-ΔCterm: pet21a-SagA was mutagenized with the following primers to insert BamH1 sites flanking the hydrolase domain:

(SEQ ID NO: 8)
AACAGATCAAAGTGT*gGATCC*TGGGAACAGTACTGG (SEQ ID NO: 9)
TGCACCTGACTTTGC*gGatcc*CATGCTCGAGCACCAC The BamH1 sites are italicized. The mutated sites are indicated in lowercase. The plasmid was then cut with BamH1 and re-ligated to form pET21a-ΔCterm, resulting in an in-frame excision of residues 390 through 529 in the SagA protein sequence.

pET21a-SagA-SS: SagA-SS was PCR amplified from pET21a-SagA BamH1 (see pAM401-SagA section below) using the following primers:

FW:
(SEQ ID NO: 10)
CATCAC*CATATG*GACGATTTTGATTCTCAGATA

RV:
(SEQ ID NO: 11)
CATCAC*GGATCC*TTTCGGGCTTTGTTA

The Nde1 and BamH1 sites are italicized. This PCR product was cut and ligated back into cut pET21a-SagA BamH1, resulting in an in-frame excision of residues 2 through 27 in the SagA protein sequence.

pAM401-psagA:mcherry: The promoter region of sagA (psagA) was PCR amplified from the *E. faecium* Com15 genome using following primers:

FW:
(SEQ ID NO: 12)
AAA*GTCGAC*ACGATGGTGGTCCAATTGAT

RV:
(SEQ ID NO: 13)
TTT*CATATG*TCATTCCTCCGACTGGCTTA

Restriction sites for Sal1 and Nde1 are italicized. The PCR product was gel purified and subcloned into pGEMTeasy for sequencing. psagA was excised with Sal1 and Nde1, and ligated into cut pAM401-padd9:mcherry (**see below) to replace paad9 with psagA.

pAM401-SagA:

pET21a-SagA was mutagenized to insert a BamH1 site after the 6x-His using the following primer to generate pET21a-SagA_BamH1:

(SEQ ID NO: 14)
TAACAAAGCCCGAAAGGAtccTGAGTTGGCTGCTGC

The BamH1 site is italicized. The mutated sites are indicated in lowercase. sagA-his6 was then excised with Nde1 and BamH1, and ligated into cut pAM401-psagA:mcherry to replace mcherry with SagA-His$_6$. pAM401-SagA was transformed into E. faecium Com15 as described below in this Example.

*Generating E. faecalis-sagA: pTEX5501ts-OG1RF-sagA:

pTEX5501ts 986 bp of sequence "upstream" (on the minus strand) of the intended SagA insertion site was PCR amplified using the following primers:

FW:
(SEQ ID NO: 15)
AAACGGCCGAGTGGGGCGTGTTATTGAAG

RV:
(SEQ ID NO: 16)
TTTGTCGACGGGTAAGCTTCTCATCGTTTTG

The Eag1 and Sal1 sites are italicized. 1013 bp of sequence "downstream" (on the minus strand) of the intended SagA insertion site was PCR amplified using the following primers:

FW:
(SEQ ID NO: 17)
AAACTGCAGTGGAGCCTTGAAGAAAGTTG

RV:
(SEQ ID NO: 18)
TTTGGTACCATTGGCTGCTTTTGTTGCTT

The Pst1 and Kpn1 sites are italicized. The upstream and downstream PCR products were subcloned into pGEMTeasy and sequenced, then were excised and ligated into cut pTEX5501ts sequentially. (Note: For the Eag1/Sal1 double digest of pTEX4401ts, Sal1 was added first, then Eag1 because the restriction sites overlap in the vector, and Eag1 can cut more efficiently at the end of a linear DNA fragment). psagA:sagA-his$_6$ was excised from pAM401-SagA with Sal1 and BamH1 and inserted into the cut vector, generating pTEX5501ts-OG1RF-sagA. OG1RF-sagA-his$_6$ was generated using an established protocol. Briefly, OG1RF was transformed with pTEX5501ts-OG1RF-sagA and single recombinants were selected after plasmid curing at 37° C. Then colonies were passaged at 37° C. and screened for gentamicin sensitivity and chloramphenicol resistance until such a clone was identified. Chromosomal insertion was verified by PCR and sequencing.

**pAM401-paad9:mcherry: paad9:mcherry was designed by us into pUC57. It encodes the synthetic promoter to aad9 flanked by Sal1 and Nde1 restriction sites, driving mcherry flanked by Nde1 and BamH1 restriction sites. paad9:mcherry was excised from pUC57 with Sal1 and BamH1 and ligated into cut pAM401, inserting into the Tet$^R$ gene.

Electroporation of Enterococcus: Protocol for preparation of electrocompetent cells and electroporation was adapted from Briefly, Enterococcus were grown for 18 hours in M9YE (M9 media, 0.1% casamino acids, 0.3% yeast extract)+2% glycine. Cultures were diluted in half with M9YE+3% glycine, and grown for an additional 3 hours. Cultures were chilled, pelleted, and washed 3 times in sucrose wash buffer (0.625 M sucrose, 1 mM MgCl$_2$, pH 4 with HCl), reducing the original culture volume by ½, ¹⁄₁₀, then ¹⁄₁₀₀ successively with each wash. Finally, cells were aliquoted, flash frozen in liquid nitrogen, and stored at −80° C. Cells were electroporated in 2 mm cuvettes, 25 µF, 400 ohm, 2.5 kV. Cells were allowed to recover for 2 hours at room temperature without shaking in Todd-Hewitt Broth (BD Bacto) then with shaking at 37° C. for an additional 2 hours before plating on selective media.

Protein purification: For E. faecium Com15 protein expression, plasmid-carrying strains were grown in BHI with appropriate antibiotics overnight. For E. coli BL21-RIL (DE3), LB cultures were inoculated with overnight cultures with appropriate antibiotics, grown for 2 hours or until OD600~0.4, induced with 1 mM IPTG, then grown for an additional 2 hours. His$_6$-tagged proteins were purified from culture supernatants using Ni-NTA agarose (Qiagen). Native purifications were performed as recommended in the manufacturer's protocol. Purified protein was dialyzed into PBS at 4° C. overnight using 5 kDa or 7 kDa MWCO Slide-a-lyzers (Pierce Protein Biology). Protein concentration was estimated by BCA assay (Pierce Protein Biology) and protein was stored at −20° C.

Protein gel methods and Western blotting: Proteins were separated by SDS-PAGE on 4-20% Criterion Tris-HCl or Criterion TGX precast gels (Bio-Rad). Protein was visualized either by Coomassie blue (Bio-Rad) staining or stain-free imaging on a ChemiDoc MP system (Bio-Rad). Glycoproteins were visualized using the Pierce Glycoprotein staining kit (Thermo Scientific) as per the manufacturer's protocol. For Western blotting, proteins were transferred to nitrocellulose membrane. HRP conjugated polyclonal anti-His$_6$ (abcam ab1187) and monoclonal anti-actin (abcam ab14128) were used for His$_6$ and actin Western blots respectively. Western blots were visualized either by developing film or imaging on a ChemiDoc MP system.

Bacterial growth curves: Growth of E. coli expressing SagA, AS, or SagA-SS: Cultures were grown as described for protein purification, except that OD600 was monitored at given time points using a Spectromax M2e spectrophotometer.

Growth of E. coli and S. Typhimurium in the presence of SagA: LB media was inoculated with overnight cultures 1:100. Protein was added at 10 µg/mL and volumes were normalized across all conditions with PBS. OD$_{600}$ was measured at given time points. Growth of OG1RF-sagA: BHI media was inoculated with overnight cultures 1:100. Chloramphenicol was added at 10 µg/mL as indicated. OD600 was measured at given time points.

Salmonella protein secretion assay: For each condition, 2 mL of LB was inoculated with overnight cultures 1:30. Protein was added to media at 10 µg/mL and volumes were normalized across all conditions with PBS. Cultures were grown for 4 hours, shaking at 37° C., the pelleted at 7000 g for 5 minutes. 1 mL of culture supernatant was precipitated with trichloro acetic acid (TCA) at a final concentration of 10% overnight at 4° C. Precipitated proteins were pelleted at 20,800 g for 30 minutes, rinsed 2 times in acetone, then air-dried. Proteins were then separated by SDS-PAGE and visualized by Coomassie staining.

C. elegans infection assays: For each condition, 3 plates of 30 worms each (total 90 worms) were scored, unless otherwise noted. Mean percent survival and standard deviation of the triplicate plates for a representative experiment are shown for extended data figures. Mean percent survival and statistical comparisons by log rank test after Bonferroni correction for multiple comparisons using OASIS software are shown in the figures. E. faecium refers to strain Com15 unless otherwise noted in the figure legends. Worms were handled using a Leica M60 microscope and imaged using a Leica IC80 HD camera.

Pulsed infection assay: Worms were synchronized using established techniques. Synchronized young adult worms were washed in S buffer (129 mL 0.05 M $K_2HPO_4$, 871 mL 0.05 M $KH_2PO_4$, 5.85 g NaCl) and transferred to bacterial lawns grown on 2% agar BHI plates for colonization for 1 day. Then, worms were washed and transferred to lawns of OP50 or IR715 grown on BHI plates for infection for another day. Finally, worms were washed and transferred to lawns of OP50 grown on NGM plates (Day 0). Worms were maintained on OP50-NGM plates and survival was scored using established techniques.

Liquid-treatment pulsed infection assay: Synchronized young adult worms were transferred to 96-well plate wells containing 32% BHI media, culture supernatant, or live cultures. For protein treatments, 10-20 μg/mL of protein in PBS was included in each well. For treatment with peptidoglycan digests, 100 μL of each digest was added to each well. For treatment with defined peptidoglycan fragments, 50 μM of each fragment in a mixture of PBS and water was included in each well. MDP, GlcNAc, and MurNAc were purchased from Sigma-Aldrich. MurNAc-L-Ala was synthesized as described below in Scheme 51. After 2 hours, worms were washed and transferred to lawns of IR715 grown on BHI plates for 1 day. Then, worms were washed and transferred to lawns of OP50 grown on NGM plates (Day 0). Worms were maintained on OP50-NGM plates and survival was scored.

Continuous infection assay: Synchronized young adult worms were washed and transferred to bacterial lawns grown on 2% agar BHI plates for colonization for 1 day. Then, worms were washed and transferred to lawns of OP50 or IR715 grown on NGM plates (Day 0). Worms were maintained on OP50 or IR715 NGM plates and survival was scored.

OG1RF pathogenesis assay: This assay was performed using known techniques. Briefly, synchronized young adult worms were washed and transferred to Com15, OG1RF, or OG1RF-sagA bacterial lawns grown on BHI plates (Day 0). Worms were maintained on Com15, OG1RF, or OG1RF-sagA BHI plates, and survival was scored.

Worm CFU measurements: Protocol for CFU measurements was adapted from previous protocol. Briefly, 5-20 worms were rinsed in drops of S buffer, and allowed to crawl free of bacteria on a sterile plate. These worms were then mechanically lysed in PBS using microtubes and pestles (Kimble-Chase). Serial dilutions of worm homogenate were plated on Salmonella-Shigella agar (BD BBL) or Enterococcosel (BD BBL) agar plates, and plates were incubated at 37° C. overnight.

Treatment of culture supernatants: Proteinase K treatment: Culture supernatant or media was digested with 0.1 mg/mL of proteinase K in the presence of 1 mM $CaCl_2$ for 2 hours at 37° C. Then, 1 mM EGTA was added, and digestions were used in the liquid-treatment pulsed infection assay.

Trichloroacetic acid precipitation: Culture supernatant or media was precipitated with TCA (final concentration of 10%) overnight at 4° C. Precipitated proteins were pelleted and rinsed 2 times in acetone, then air-dried and resuspended in BHI media before use in the liquid-treatment pulsed infection assay. 10-kDa MWCO column filtration: E. faecium culture supernatant or media was filtered through 10-kDa MWCO columns (Vivaspin GE Healthcare), and the flow-thru was used in the liquid-treatment pulsed infection assay.

5-kDa MWCO column filtration of E. coli culture supernatants: E. coli BL21-RIL(DE3) expressing SagA-His or AS-His were induced in BHI media instead of LB as described above. Portions of the culture supernatants were filtered through 5-kDa MWCO columns (Vivaspin GE Healthcare), and the unfiltered supernatants, column concentrate, and column flow-thru were used in the liquid-treatment pulsed infection assay.

Peptidoglycan Digests: 100 μg of E. coli peptidoglycan (Invivogen) was digested with 20 μg lysozyme (Sigma) and 20 μg of SagA-His or AS-His overnight in a mixture of PBS and water at 37° C. Digests were then filtered through 5-kDa MWCO columns (Vivaspin GE Healthcare), and the flow-thru was used in the liquid-treatment pulsed infection assay.

Synthesis of N-acetylmuramic acid-L-alanine:

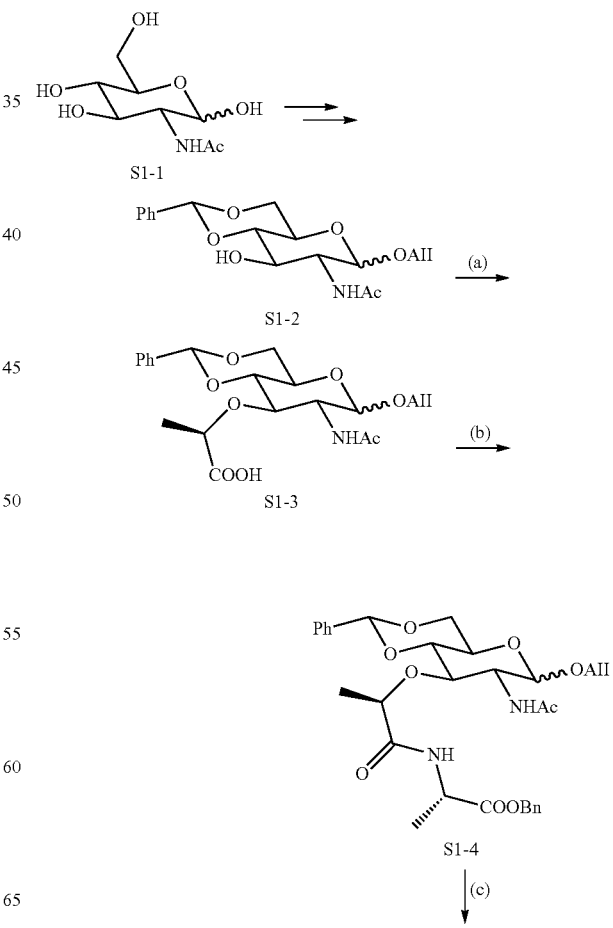

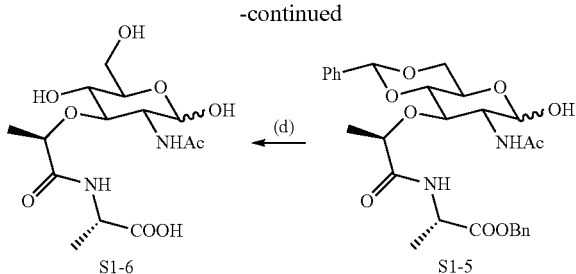

Synthesis of the N-acetylmuramic acid-L-alanine, Reagents and conditions:
(a) (S)-2-chloropropionic aicd, NaH, 45° C., 16 h.
(b) Ala-OBn, DIEA, C—HOBt, DIC, CH$_2$Cl$_2$/DMF, RT, 16 h.
(c) Pd(PPh$_3$)$_4$, AcOH, 40° C., 16 h.
(d) (i) 60% AcOH, 40-50° C., 1.5 h; (ii) Pd/C, H$_2$, MeOH, RT, 5 h.

Compound S1-2. S1-2 was synthesized from commercially available N-acetylglucosamine (S1-1) by following and adapting published protocols.

Compound S1-3. NaH (0.16 g, 6.67 mmol) was added to a suspension of compound S1-2 (0.358 g, 1.02 mmol) in 1,4-dioxane (9 mL). The mixture was stirred at 40° C. for 1 h. (S)-2-chloropropionic acid (0.27 mL, 2.95 mmol) in 1,4-dioxane (3 mL) was added to the reaction mixture dropwise. The mixture was stirred at 45° C. for 16 h. The solvent was removed under vacuum. H$_2$O (20 mL) and 1MHCl$_{(aq)}$ (20 mL) was added. The mixture was extracted with CH$_2$Cl$_2$ (3×25 mL) and the combined organic layers were dried with MgSO$_4$ and concentrated by rotary evaporation. The resulting solid was washed with cold Et$_2$O several times and dried in vacuum to yield S1-3 as a white solid (95 mg, 22%). Crude compound (S1-3) was used without further purification.

$^1$H NMR (400 MHz, CD$_3$OD): δ7.47 (d, J=4.1 Hz, 2H), 7.37 (d, J=5.0 Hz, 3H), 5.88 (m, 1H), 5.64 (s, 1H), 5.28 (d, J=17.2 Hz, 1H), 5.15 (d, J=10.4 Hz, 1H), 4.63 (d, J=7.7 Hz, 1H), 4.40 (q, J=6.9 Hz, 1H), 4.31 (d, J=4.9 Hz, 1H), 4.28 (t, J=4.6 Hz, 1H), 4.07 (m, 1H), 3.76 (m, 3H), 3.67 (t, J=4.2 Hz, 1H), 3.49 (m, 3H), 1.99 (s, 3H), 1.34 (d, J=6.9 Hz, 3H). ESI-MS [M+H$^+$]: m/z calc. for C$_{21}$H$_{28}$NO$_8^+$: 422.1809; found: 422.1807.

Compound S1-4. L-alanine benzyl ester hydrochloride (68 mg, 0.315 mmol) and N,N-diisopropylethylamine (0.118 mL, 0.677 mmol) were added to a suspension of compound S1-2 (0.95 mg, 0.225 mmol) in CH$_2$Cl$_2$. 6-Chloro-1-hydroxybenzotriazole (57 mg, 0.336 mmol) in DMF (0.7 mL) was added to the reaction mixture. N,N'-diisopropylcarbodiimide (45 uL, 0.291 mmol) was added to the reaction mixture. The mixture was stirred at room temperature for 16 h. 1M HCl$_{(aq)}$ (40 mL) was added to quench the reaction. The mixture was extracted with CH$_2$Cl$_2$ (2×25 mL) and the combined organic layers were dried with MgSO$_4$ and concentrated by rotary evaporation. The resulting solid was washed with cold MeOH several times and dried in vacuum to yield S1-4 as a white solid (93 mg, 71%). Crude compound (S1-4) was used in the next step without further purification.

$^1$H NMR (400 MHz, DMSO-d$_6$): δ7.41 (m, 10H), 5.84 (m, 1H), 5.69 (s, 1H), 5.25 (dd, J=17.4, 1.8 Hz, 1H), 5.15 (d, J=12.8 Hz, 2H), 5.09 (d, 12.6 Hz, 1H),
4.53 (d, J=8.4 Hz, 1H), 4.31 (t, 7.4 Hz, 1H), 4.23 (m, 2H), 4.04 (m, 2H), 3.80 (m, 2H), 3.65 (t, 8.7 Hz, 2H), 3.42 (m, 1H), 1.79 (s, 3H), 1.34 (d, 7.8 Hz, 3H), 1.21 (d, 6.6 Hz, 3H). $^{13}$C NMR (600 MHz, DMSO-d$_6$): δ172.56, 172.40, 170.27, 138.01, 136.37, 134.93, 129.27, 128.87, 128.61, 128.49, 128.20, 126.32, 116.76, 101.25, 100.58, 80.45, 79.71, 77.70, 69.55, 68.23, 66.41, 66.09, 55.20, 47.97, 23.77, 23.47, 19.32, 17.28. ESI-MS [M+H$^+$]: m/z calc. for C$_{31}$H$_{39}$N$_2$O$_9^+$: 583.2650; found: 583.2650.

Compound S1-5. Tetrakis(triphenylphosphine)palladium (0) (95 mg, 0.082 mmol) was added to a suspension of compound S1-4 (93 mg, 0.160 mmol) in AcOH (1.5 mL). The mixture was stirred at 40° C. for 16 h. The solution was purified by silica gel column chromatography (MeOH/EtOAc/hexanes=0.5/7/7)) to yield S1-5 as a light yellow solid (57 mg, 66%).

$^1$H NMR (600 MHz, CD$_3$OD): δ7.50 (d, J=4.2 Hz, 2H), 7.34 (m, 8H), 5.65 (s, 1H), 5.21 (d, J=3.6 Hz, 1H), 5.19 (s, 2H), 4.44 (q, J=7.2 Hz, 1H), 4.27 (q, J=6.6 Hz, 1H), 4.21 (dd, J=10.2, 4.8 Hz, 1H), 4.04 (m, 2H), 3.82 (m, 2H), 3.69 (t, J=9.6 Hz, 1H), 1.97 (s, 3H), 1.42 (d, J=7.2 Hz, 3H), 1.31 (d, J=6.6 Hz, 3H). $^{13}$C NMR (600 MHz, CD$_3$OD): δ174.50, 172.34, 172.20, 137.79, 135.81, 128.52, 128.20, 127.93, 127.86, 127.74, 125.92, 101.40, 101.25, 91.73, 82.08, 77.04, 76.16, 68.73, 66.61, 62.35, 54.21, 21.49, 18.34, 15.91. ESI-MS [M+H$^+$]: m/z calc. for C$_{28}$H$_{35}$N$_2$O$_9^+$: 543.2337; found: 543.2338.

Compound S1-6. Compound S1-5 was suspended in AcOH (0.6 mL) and H$_2$O (0.4 mL). The mixture was stirred at 50° C. for 1 h and 40° C. for 30 min. The solvent was removed under vacuum. The resulting solid was dissolved in MeOH (2 mL). 10% palladium on carbon (21 mg) was added to the solution. The mixture was stirred under 1 atm. of H$_2$ at room temperature for 5 h. After filtration, the solution was concentrated by rotary evaporation. The resulting oil was purified by silica gel column chromatography (MeOH/CHCl$_{3=3:7}$ to 4:6) to yield compound S1-6 (α-anomer). $^1$H NMR (600 MHz, CD$_3$OD): δ5.13 (d, J=3.6 Hz, 1H), 4.39 (q, J=7.2 Hz, 1H), 4.34 (q, J=6.6 Hz, 1H), 3.94 (dd, J=10.2, 3.0 Hz, 1H), 3.82 (m, 2H), 3.73 (m, 1H), 3.68 (m, 1H), 3.50 (m, 1H), 1.97 (s, 3H), 1.45 (d, J=7.6 Hz, 3H), 1.41 (d, J=7.1 Hz, 3H). $^{13}$C NMR (600 MHz, CD$_3$OD): δ174.55, 174.36, 172.07, 95.88, 91.15, 79.38, 77.14, 71.83, 70.10, 61.27, 53.96, 21.46, 18.10, 16.27. ESI-MS [M+H$^+$]: m/z calc. for C$_{14}$H$_{25}$N$_2$O$_9^+$: 365.1555; found: 365.1555.

Proteomics: In-gel digestion: 1 mL of culture supernatant was precipitated with TCA as described above, resuspended in loading buffer and separated by SDS-PAGE. Proteins were processed for in-gel digestion with sequencing grade trypsin (Promega) using known techniques except that dried samples were resuspended in 5% acetonitrile, 2% formic acid in water.

In-Solution Digestion:

1 mL of culture supernatant was precipitated with TCA as described above, and proteins were digested with 0.2 μg of trypsin in 50 mM ammonium bicarbonate buffer overnight at 37° C. Samples were dried by speed-vac, then resuspended in 5% acetonitrile, 2% formic acid in water. LC-MS was performed on digested peptides and peptide spectra were analyzed against the E. faecium Com15 proteome using Mascot v2.3 and Proteome Discoverer software.

8-aminonaphthalene 1,3,6 trisulfonic acid (ANTS) labeling assay:

E. coli supernatants were prepared by inoculating cultures 1:50 with an overnight culture of E. coli BL21-RIL(DE3) expressing SagA-His6 or AS-His6. Cultures were grown for 2 hours, then induced with 1 mM IPTG, and grown for an additional 2 hours. Enterococcus supernatants were prepared by growing cultures overnight. Cultures were pelleted, and supernatant was filtered through 10 kDa MWCO columns (Millipore Microcon). For peptidoglycan digests, 100 μg of E. coli peptidoglycan was digested with 20 μg lysozyme and 20 μg of SagA-His or AS-His overnight in a mixture of PBS and water at 37° C. Digests were filtered through 10 kDa MWCO columns. Culture supernatants, peptidoglycan digests, and defined peptidoglycan fragments were dried by speed-vac before ANTS labeling. ANTS labeling was using established techniques. 10 µl of ANTS reaction mix was added to each tube of dried material (1:1 mixture of 0.2 M ANTS (in 3:17 acetic acid:water): 1 M NaCNBH3 (in DMSO)). Reactions were incubated overnight at 37° C. 0.5-3.5 µL of the ANTS labeled mixtures were mixed 1:1 with 40% glycerol and samples were separated by native PAGE on a hand-cast 37-40% Tris-glycine acrylamide gel (19:1 polyacrylamide:bisacrylamide, with a 20% acrylamide stack) at 150 V for ~3 hours or 80 V for ~6 hours. Empty lanes adjacent to sample lanes were loaded with samples of ANTS labeled Ala-D-γ-Glu-Lys-D-Ala-D-Ala (Sigma). Remaining lanes were loaded with 20% glycerol. Gels were imaged on the ChemiDoc MP system (Bio-Rad) using the Sybr-safe UV imaging setting.

Epifluorescence:

For imaging of mcherry-*Salmonella*, worms were treated as described for the pulsed infection assays except worms were infected with *S. Typhimurium* carrying the plasmid p67MC1. For imaging of *E. faecium* psagA:mcherry, worms were fed *E. faecium* carrying the plasmid pAM401-mcherry for 1 day on BHI plates. Worms were mounted as described (18), except that worms were paralyzed in 1 mM tetramisole (Sigma) instead of sodium azide. Worms were imaged on a Nikon Eclipse TS100 and pictures were taken using a Nikon Digital Sight DS-Fi1.

Electron Microscopy:

Animals were prepared for electron microscopy using standard methods. Ultrathin serial sections (70 nm) were collected by using a Leica Ultracut UCT Ultramicrotome. Sections at two regions, 120 µm and 200 µm away from the head region, were examined for each condition. EM images were acquired using an FEI Tecnai G2 Spirit BioTwin transmission electron microscope operating at 80 kV with a Gatan 4K×4K digital camera.

TABLE 1

Proteins identified from *E. faecium* Com15 culture supernatant by mass spectrometry, after in-gel digestion. Proteins listed have at least 2 unique peptides identified. Proteins involved in peptidoglycan remodeling are italicized and bolded.

| Uniprot Accession | Gene name | Description | # Unique Peptides | # PSMs |
|---|---|---|---|---|
| C9ASF4 | *sagA* | Secreted lipase | 33 | 447 |
| C9ASF5 | | | | |
| C9AS94 | | Mannosyl-glycoprotein endo-beta-N-acetylglucosamidase | 16 | 103 |
| C9AKY4 | | Peptidoglycan-binding protein LysM | 8 | 93 |
| C9AQS4 | | Extracellular solute-binding protein | 18 | 92 |
| C9AQL4 | | Basic membrane lipoprotein | 24 | 85 |
| C9ASJ4 | | N-acetylmuramoyl-L-alanine amidase | 23 | 78 |
| C9ATH2 | | Beta-1,4-N-acetylmuramoylhydrolase | 16 | 76 |
| C9AKY1 | | Periplasmic solute binding protein | 21 | 68 |
| C9AQT6 | | Periplasmic binding protein | 16 | 63 |
| C9ANP2 | | N-acetylmuramoyl-L-alanine amidase | 10 | 57 |
| C9APB3 | | Putative uncharacterized protein | 16 | 56 |
| C9ALQ1 | eno | Enolase | 23 | 55 |
| C9APJ5 | | Penicillin-binding protein | 23 | 48 |
| C9AMB1 | | Sulfatase | 20 | 45 |
| C9ALP8 | | Glyceraldehyde-3-phosphate dehydrogenase | 10 | 43 |
| C9AQM8 | tuf | Elongation factor Tu 2 | 13 | 41 |
| C9ALW6 | | Glycosyl transferase | 20 | 41 |
| C9ARZ3 | | Extracellular solute-binding protein | 12 | 41 |
| C9AMG6 | arcA | Arginine deiminase | 17 | 39 |
| C9AML5 | | Amino acid ABC transporter | 8 | 36 |
| C9ASF9 | | ErfK/YbiS/YcfS/YnhG family protein | 16 | 34 |
| C9AS22 | | FMN-binding protein | 10 | 34 |
| C9API8 | | Pyruvate kinase | 19 | 33 |
| C9ALP9 | pgk | Phosphoglycerate kinase | 13 | 31 |
| C9AMK8 | dnaK | Chaperone protein DnaK | 23 | 31 |
| C9AMB7 | pgi | Glucose-6-phosphate isomerase | 15 | 29 |
| C9ALB5 | | Sulfatase | 16 | 29 |
| C9AMH5 | tsf | Elongation factor Ts | 11 | 27 |
| C9AQB2 | | Fructose-bisphosphate aldolase class-II | 10 | 25 |
| C9ARP7 | | Glycine betaine/L-proline ABC transporter | 9 | 25 |
| C9API8 | | D-alanyl-D-alanine carboxypeptidase | 10 | 23 |
| C9APP4 | | Transcriptional regulator | 10 | 23 |
| C9ANA8 | | Extracellular solute-binding protein | 17 | 23 |
| C9AL01 | | Extracellular solute-binding protein | 17 | 21 |
| C9ANQ7 | | Peptidyl-prolyl cis-trans isomerase | 7 | 20 |
| C9ARQ9 | groEL | 60 kDa chaperonin | 15 | 19 |
| C9ANB6 | | Extracellular solute-binding protein | 9 | 19 |
| C9ATA9 | | ATP-dependent Clp protease | 14 | 18 |
| C9AME5 | | Iron compound ABC transporter | 11 | 18 |
| C9AQM7 | fusA | Elongation factor G | 10 | 16 |
| C9AS40 | | ABC transporter substrate binding protein | 10 | 16 |
| C9ANN9 | | NADH oxidase | 10 | 15 |
| C9AMN8 | tig | Trigger factor | 11 | 14 |
| C9APM7 | | Phosphoenolpyruvate-protein phosphotransferase | 11 | 12 |
| C9AGM7 | | Ornithine carbamoyltransferase | 7 | 12 |

TABLE 1-continued

Proteins identified from *E. faecium* Com15 culture supernatant by mass spectrometry, after in-gel digestion.
Proteins listed have at least 2 unique peptides identified.
Proteins involved in peptidoglycan remodeling are italicized and bolded.

| Uniprot Accession | Gene name | Description | # Unique Peptides | # PSMs |
|---|---|---|---|---|
| C9AP95 | | Ribosomal protein S1 | 10 | 12 |
| C9ARE8 | prsA | PpiC-type peptidyl-prolyl cis-trans isomerase | 8 | 12 |
| C9ALQ0 | tpiA | Triosephosphate isomerase | 6 | 12 |
| C9ASG0 | ldh | L-lactate dehydeogenase 2 | 8 | 11 |
| C9APR1 | | Predicted protein | 5 | 11 |
| C9AQP2 | rpIE | 50S ribosomal protein L5 | 4 | 10 |
| C9ANQ4 | | Glyceraldehyde-3-phosphate dehydrogenase | 7 | 10 |
| C9APA2 | | Peeptidase M20A | 8 | 10 |
| C9ANB3 | | Putative uncharacterized protein | 5 | 10 |
| C9AR88 | | Peptidase S1 | 6 | 10 |
| C9APC1 | tuf | Elongation factor Tu 1 | 7 | 9 |
| C9API4 | | 6-phosphogluconate-dehydrogenase, decarboxylating | 8 | 9 |
| C9AQB4 | | Glutamine synthetase | 8 | 9 |
| C9AN26 | | Heat shock protein | 3 | 9 |
| C9ARH9 | | Acyltransferase | 6 | 8 |
| C9AL54 | | NLPA lipoprotein | 4 | 8 |
| C9APP1 | | Chitin-binding protein | 6 | 8 |
| C9ALX9 | | Phosphoglucomutase/phosphomannomutase | 7 | 7 |
| C9AR81 | | Peptidase M20A | 5 | 7 |
| C9ASX8 | | Putative unchacatreized protein | 4 | 7 |
| C9ATI6 | | Extracellular solute-binding protein | 5 | 7 |
| C9ART9 | | Sulfastase | 6 | 7 |
| C9AQP7 | rpsE | 30S ribosomal protein S5 | 4 | 6 |
| C9AQK7 | guaA | GMP synthase [glutamine-hydrolyzing] | 5 | 6 |
| C9AS47 | | Ferritin | 4 | 6 |
| C9ANE7 | | Putative uncharacterized protein | 2 | 6 |
| C9ATD5 | | Intracellular protease | 4 | 6 |
| C9AQP5 | rpIF | 50S ribosomal protein L6 | 5 | 6 |
| C9AQI8 | | Oligopeptide binding protein | 5 | 6 |
| C9ARL2 | rpIK | 50S ribosomal protein L11 | 4 | 5 |
| C9ASH2 | lysS | Lysine--tRNA ligase | 4 | 5 |
| C9AMH7 | frr | Ribosome-recycling factor | 5 | 5 |
| C9AMC8 | | Predicted protein | 5 | 5 |
| C9AQQ1 | adk | Adenylate kinase | 5 | 5 |
| C9ARL5 | rpIL | 50S ribosomal protein L7/L12 | 4 | 5 |
| C9AKW7 | | NAD(FAD)dependent dehydrogenase | 5 | 5 |
| C9AM30 | | Putative uncharacterized protein | 4 | 5 |
| C9ALT5 | | Sigma 54 modulation protein/ribosomal protein S30EA | 4 | 5 |
| C9AN78 | | Putative uncharacterized protein | 5 | 5 |
| C9AL85 | prsA | PpiC-type peptidyl-prolyl cis-trans isomerase | 4 | 5 |
| C9AN90 | | Cell envelope transcriptional attenuator | 4 | 5 |
| C9ASN4 | | Putative uncharacterized protein | 3 | 5 |
| C9AQM6 | rpsG | 30S ribosomal protein S7 | 2 | 4 |
| C9APQ3 | | Superoxide dismutase | 3 | 4 |
| C9AP93 | | DNA binding protein HU | 4 | 4 |
| C9AQP4 | rpsH | 30S ribosomal protein S8 | 3 | 4 |
| C9AS49 | rpsI | 30S ribosomal protein S9 | 2 | 4 |
| C9API9 | pfkA | 6-phosphofructokinase | 3 | 4 |
| C9ASN2 | | Pyridoxal-dependent decarboxylase | 3 | 4 |
| C9AQQ7 | rpIQ | 50S ribosomal protein L7 | 4 | 4 |
| C9ANY2 | | Transketolase | 4 | 4 |
| C9ARX0 | | Signal peptidase I | 3 | 4 |
| C9AQP1 | rpIX | 50S ribosomal protein L24 | 4 | 4 |
| C9AQB3 | pyrG | CTP synthase | 4 | 4 |
| C9ALR9 | atpD | ATP synthase F1 | 4 | 4 |
| C9AQM2 | gpmA | 2,3-bisphosphopglycerate-dependent phosphoglycerate mutase 2 | 2 | 4 |
| C9ARX9 | upp | Uracil phosphoribosyltransferase | 3 | 4 |
| C9APR6 | | Putative uncharacterized protein | 4 | 4 |
| C9ATB9 | | Cupin domain-containing protein | 2 | 4 |
| C9ASG5 | | Septum formation initiator | 3 | 4 |
| C9AKX7 | | Putative uncharacterized protein | 2 | 4 |
| C9ANY1 | | Dihydrolipoamide S-succinyltransferase | 3 | 3 |
| C9ALN5 | | Glyoxalase/bleomycin resistance protein/dioxygenase | 3 | 3 |
| C9ANP3 | | Transketolase | 2 | 3 |
| C9ARQ8 | groES | 10 kDa chaperonin | 3 | 3 |
| C9AQF3 | guaB | Inosine-5'-monophosphate dehydrogenase | 2 | 3 |
| C9ARL3 | rpIA | 50S ribosomal protein L1 | 3 | 3 |
| C9AQN1 | rpID | 50S ribosomal protein L4 | 2 | 3 |
| C9ALV5 | | UTP-glucose-1-phosphate uridyltransferase | 2 | 3 |
| C9ARL4 | rpIJ | 50S ribosomal protein L10 | 3 | 3 |
| C9AMD1 | | Putative uncharacterized protein | 2 | 3 |

TABLE 1-continued

Proteins identified from E. faecium Com15 culture supernatant by mass spectrometry, after in-gel digestion. Proteins listed have at least 2 unique peptides identified. Proteins involved in peptidoglycan remodeling are italicized and bolded.

| Uniprot Accession | Gene name | Description | # Unique Peptides | # PSMs |
|---|---|---|---|---|
| C9APR5 | freA | Transcription elongation factor greA | 2 | 3 |
| C9AS03 | metG | Methionyl-tRNA synthetase | 2 | 3 |
| C9AP54 | ppaC | Probable manganese-dependent inorganic pyrophosphatase | 2 | 3 |
| C9ARH5 | | Aldo-keto reductase | 2 | 3 |
| C9AR84 | | Glutamyl aminopeptidase | 3 | 3 |
| C9ALL0 | | Putative uncharacterized protein | 3 | 3 |
| C9AQN6 | rpsC | 30S ribosomal protein S3 | 3 | 3 |
| C9ALV7 | | Putative uncharacterized protein | 3 | 3 |
| C9ANI8 | | HD domain-containing protein | 3 | 3 |
| C9AN38 | prsA | Foldase protein prsA 2 | 2 | 3 |
| C9AP35 | | Putative uncharacterized protein | 3 | 3 |
| C9AQM9 | rpsJ | Ribosomal protein S10 | 2 | 2 |
| C9AMH4 | rpsB | 30S ribosomal protein S2 | 2 | 2 |
| C9AMN9 | clpX | ATP-dependent Clp protease ATP-binding subunit ClpX | 2 | 2 |
| C9ASA9 | gltX | Glutamate--tRNA ligase | 2 | 2 |
| C9AQZ1 | pnp | Polyribonucleotide nucleotidyltransferase | 2 | 2 |
| C9AQP6 | rplR | 50S ribosomal protein L18 | 2 | 2 |
| C9AL22 | | M13 family peptidase | 2 | 2 |
| C9ARB8 | | Predicted protein | 2 | 2 |
| C9ARX7 | glyA | Pyridoxal-phosphate-dependent serine hydroxymethyltransferase | 2 | 2 |
| C9AQ30 | ftsZ | Cell division protein ftsZ | 2 | 2 |
| C9AP56 | | Formate acetyltransferase | 2 | 2 |
| C9APC4 | | 2,5-didehydrogluconate reductase | 2 | 2 |
| C9ALP6 | | 3-oxoacyl-[acyl-carrier-protein] synthase 2 | 2 | 2 |
| C9AQA9 | rpmE2 | 50S ribosomal protein L31 type B | 2 | 2 |
| C9AM29 | | D-alanyl-D-alanine carboxypeptidase | 2 | 2 |
| C9ASN3 | tyrS | Tyrosine--tRNA ligase | 2 | 2 |
| C9ANP1 | | Cysteine synthase | 2 | 2 |
| C9AQ59 | rpmA | 50S ribosomal protein L27 | 2 | 2 |
| C9AQN5 | rplV | 50S ribosomal protein L22 | 2 | 2 |
| C9AQ61 | rplU | 50S ribosomal protein L21 | 2 | 2 |
| C9ALP9 | acpP | Acyl carrier protein 1 | 2 | 2 |
| C9AMM5 | | Putative uncharacterized protein | 2 | 2 |
| C9ARS4 | nadE | NH(3)-dependent NAD(+) synthetase | 2 | 2 |
| C9ALC7 | | Putative uncharacterized protein | 2 | 2 |
| C9AP38 | | ABC transporter | 2 | 2 |
| C9ASJ8 | | Putative uncharacterized protein | 2 | 2 |
| C9ALI4 | | Putative uncharacterized protein | 2 | 2 |
| C9AN28 | | Predicted protein | 2 | 2 |
| C9ALC4 | | Lipoprotein YaeC | 2 | 2 |
| C9ASP9 | | Cell wall surface adhesion protein | 2 | 2 |
| C9APR0 | | Putative uncharacterized protein | 2 | 2 |

PSM = peptide spectrum match.

TABLE 2

Proteins identified by mass spectrometry from the top and bottom bands as indicated in FIG. 3A.

| Uniprot Accession | Gene Name | Description | MW (kDa) | Unique Peptides | # PSMs Top Band | # PSMs Bottom band |
|---|---|---|---|---|---|---|
| C9ASF4, C9ASF5 | sagA | Secreted lipase | 53.6 | 17 | 104 | 13 |
| C9ALL0 | | Putative uncharacterized protein | 84.5 | 11 | 19 | |
| C9APJ5 | | Penicillin-binding protein | 78.3 | 10 | 18 | |
| C9AQM7 | fusA | Elongation factor G | 76.7 | 9 | 17 | |
| C9ASJ4 | | N-acetylmuramoyl-L-alanine amidase | 77.3 | 8 | 12 | |
| C9AQZ1 | pnp | Polyribonucleotide nucleotidyltransferase | 76.9 | 3 | 4 | |
| C9ANP3 | | Transketolase | 72.4 | 2 | 3 | |
| C9ANY1 | | Dihydrolipoamide S-succinyltransferase | 57.0 | 2 | 2 | |
| C9ANA8 | | Extracellular solute-binding protein | 45.7 | 12 | | 25 |
| C9AS94 | | Mannosyl-glycoprotein endo-beta-N-acetylglucosamidase | 46.6 | 9 | | 20 |
| C9ALQ1 | eno | Enolase | 46.5 | 10 | | 18 |

TABLE 2-continued

Proteins identified by mass spectrometry from the top and bottom bands as indicated in FIG. 3A.

| Uniprot Accession | Gene Name | Description | MW (kDa) | Unique Peptides | # PSMs Top Band | # PSMs Bottom band |
|---|---|---|---|---|---|---|
| C9APP4 | | Transcriptional regulator | 42.5 | 9 | | 13 |
| C9AQB4 | | Glutamine synthetase | 50.6 | 7 | | 11 |
| C9AQM8 | tuf | Elongation factor Tu 2 | 43.2 | 6 | | 11 |
| C9ATH2 | | Beta-1,4-N-acetylmuramoylhydrolase | 71.0 | 4 | | 9 |
| C9AMB7 | pgi | Glucose-6-phosphate isomerase | 49.7 | 6 | | 9 |
| C9API4 | | 6-phosphogluconate dehydeogenase, decarboxylating | 52.7 | 4 | | 7 |
| C9ALB5 | | Sulfatase | 79.1 | 3 | | 6 |
| C9AP95 | | Ribosomal protein S1 | 45.7 | 3 | | 5 |
| C9AMG6 | arcA | Arginine deiminase | 46.1 | 4 | | 5 |
| C9ART9 | | Sulfatase | 70.9 | 3 | | 5 |
| C9ALR9 | atpD | ATP synthatase F1 | 51.0 | 2 | | 4 |
| C9AMB1 | | Sulfatase | 80.4 | 3 | | 4 |
| C9ANE7 | | Putative uncharacterized protein | 36.7 | 2 | | 3 |
| C9AQL4 | | Basic membrane lipoprotein | 37.8 | 2 | | 2 |

TABLE 3

Proteins in *E. faecalis* OG1RF and *E. faecalis-sagA* culture supernatants identified by mass spectrometry, after in-solution digestion. Proteins listed have at least 2 unique peptides. Proteins involved in cell wall remodeling are italicized and enlarged. F2MNY6 and SagA-His6 are bold.

| Uniprot Accession | Gene Name | Description | *E. faecalis* # Unique peptides | # PSMs | *E. faecalis-sagA* # Unique Peptides | # PSMs |
|---|---|---|---|---|---|---|
| F2MNY6 | | Secreted antigen | 5 | 48 | 4 | 36 |
| F2MPG2 | pgk | Phosphoglycerate kinase | 10 | 24 | 10 | 13 |
| F2MPG0 | eno | Enolase | 9 | 22 | 8 | 15 |
| F2MR31 | | Uncharacterized protein | 8 | 16 | 14 | 47 |
| F2MQS5 | ptsI | Phosphoenolpyruvate-protein phosphotransferase | 7 | 16 | 7 | 15 |
| F2MPK1 | | Peptide ABC superfamily ABC transporter, binding protein | 7 | 15 | 12 | 23 |
| F2MNH6 | gelE | Gelatinase | 7 | 15 | 9 | 22 |
| F2MQ41 | npr | NADH peroxidase | 4 | 15 | 4 | 4 |
| F2MNQ3 | htrA | Serine protease HtrA | 4 | 13 | 3 | 4 |
| F2MQL1 | rpoC | DNA-directed RNA polymerase subunit beta' | 7 | 12 | 5 | 7 |
| F2MM76 | | ABC superfamily ABC transporter, binding protein | 6 | 11 | 10 | 23 |
| F2MNH5 | sprE | SprE protein | 4 | 11 | 5 | 20 |
| F2MQ69 | ackA | Acetate kinase | 5 | 11 | 5 | 14 |
| F2MR21 | dnaK | Chaperone protein DnaK | 9 | 11 | 8 | 11 |
| F2MTS3 | groEL | 60 kDa chaperonin | 7 | 11 | 7 | 10 |
| F2MMD6 | pepQ | Xaa-Pro dipeptidase | 4 | 11 | 4 | 9 |
| F2MSU5 | pgi | Glucose-6-phosphate isomerase | 4 | 11 | 4 | 9 |
| F2MT66 | oppA | Oligopeptide ABC superfamily ABC transporter, binding protein | 7 | 11 | 6 | 8 |
| F2MRX7 | pdhA | Pyruvate dehydrogenase complex E1 component alpha subunit | 3 | 11 | 2 | 5 |
| F2MM98 | tuf | Elogation factor Tu | 7 | 10 | 5 | 6 |
| F2MPU3 | | Transcriptional regulator | 3 | 9 | 6 | 10 |
| F2MQA4 | | ABC superfamily ABC transporter, binding protein | 2 | 9 | 4 | 10 |
| F2MST4 | trxA | Thioredoxin | 2 | 9 | 2 | 10 |
| F2MQC6 | glnA | Glutamine synthetase | 5 | 9 | 4 | 7 |
| F2MN33 | ldh | L-lactate dehydrogenase | 4 | 9 | 3 | 6 |
| F2MR74 | | ABC superfamily ABC transporter, binding protein | 3 | 8 | 9 | 15 |
| *F2MRQ5* | *lyzl6* | *Cell wall lysis protein* | *5* | *8* | *5* | *8* |
| F2MPV9 | tyrS | Tyrosine--tRNA ligase | 5 | 8 | 2 | 7 |
| F2MQH3 | ubiD2 | UbiD family decarboxylase | 6 | 8 | 4 | 6 |
| F2MQK7 | dps | DNA starvation/stationary phase protection protein Dps | 5 | 8 | 4 | 4 |
| F2MML0 | gnd | 6-phosphogluconate dehydeogenase, decarboxylating | 6 | 8 | 2 | 3 |
| F2MSU4 | gdhA | Glutamate dehydeogenase | 4 | 7 | 6 | 10 |
| *F2MQH5* | | *WxL domain surface protein* | *3* | *7* | *3* | *6* |
| F2MQ03 | fdaB | Fructose-bisphosphate aldolase | 3 | 7 | 3 | 5 |

TABLE 3-continued

Proteins in *E. faecalis* OG1RF and *E. faecalis-sagA* culture supernatants identified by mass spectrometry, after in-solution digestion. Proteins listed have at least 2 unique peptides. Proteins involved

| | | | | | | |
|---|---|---|---|---|---|---|
| F2MRX1 | | Sugar ABC superfamily ABC transporter, sugar-binding protein | 5 | 7 | 3 | 5 |
| F2MMC3 | adk | Adenylate kinase | 3 | 7 | 2 | 4 |
| F2MQX6 | | Sulfatase domain protein | 5 | 6 | 8 | 15 |
| F2MRL8 | glnP | Amino acid ABC superfamily ABC transporter-binding/permease protein | 3 | 6 | 4 | 8 |
| F2MRY0 | lpd | Dihydrolipoyl dehydrogenase | 4 | 6 | 3 | 7 |
| F2MN60 | fabF | 3-oxoacryl-1-[acryl-carrier-protein] synthase 2 | 3 | 6 | 3 | 5 |
| F2MMK6 | pfkA | 6-phosphofructokinase | 4 | 6 | 3 | 4 |
| F2MQT2 | fruK2 | Tagatose-6-phosphate kinase | 2 | 6 | 2 | 4 |
| F2MTK3 | ndh | NADH dehydrogenase | 3 | 6 | 2 | 4 |
| F2MMR7 | ccpA | Catabolite control protein A | 4 | 6 | 3 | 3 |
| F2MTG7 | hup | DNA-binding protein HU | 3 | 6 | 2 | 2 |
| F2MM84 | deoB | Phosphopentomutase | 3 | 5 | 4 | 6 |
| F2MRY7 | | Hydoxymethylglutaryl-CoA synthase | 2 | 5 | 2 | 5 |
| F2MTV6 | pflB | Formate acetyltransferase | 4 | 5 | 3 | 4 |
| F2MM91 | adh3 | Putative alcohol dehydeogenase (NADP(+)) | 2 | 4 | 3 | 7 |
| F2MTA8 | pta | Phosphate acetyltransferase | 3 | 4 | 3 | 4 |
| F2MRX8 | pdhB | Pyruvate dehydrogenase complex E1 component beta subunit | 3 | 4 | 2 | 2 |
| F2MS34 | frr | Ribosome-recycling factor | 4 | 4 | 2 | 2 |
| F2MS37 | rpsB | 30S ribosomal protein S2 | 3 | 4 | 2 | 2 |
| F2MTE1 | | Uncharacterized protein | 2 | 3 | 4 | 10 |
| F2MRB6 | | Pheromone cAD1 lipoprotein | 2 | 3 | 3 | 3 |
| F2MT59 | aad | Aldehyde-alcohol dehydrogenase | 2 | 3 | 10 | 18 |
| F2MRB5 | | Thiamine biosynthesis lipoprotein | 2 | 3 | 3 | 5 |
| F2MTQ5 | atpA2 | ATP synthase subunit alpha | 2 | 3 | 2 | 3 |
| F2MU99 | ahpC | Peroxiredoxin | 2 | 3 | 2 | 3 |
| F2MM92 | gpmA | 2,3-bisphosphoglycerate-dependent phosphoglycerate mutase | 2 | 3 | 2 | 2 |
| *F2MNI5* | | *WxL domain surface protein* | *0* | *0* | 5 | 69 |
| *F2MNH1* | | *Phosphatidylglycerol--membrane-oligosaccharide glycerophosphotransferase* | *0* | *0* | 9 | 28 |
| *F2MMF2* | *pbpC* | *Penicillin-binding protein C* | *0* | *0* | *9* | *19* |
| *F2MNV6* | | *Chitin-binding protein/carbohydrate-binding protein* | *0* | *0* | *6* | *17* |
| *F2MUF4* | *penA* | *Penicillin-binding protein 2B* | *0* | *0* | *11* | *15* |
| *F2MRA7* | | *Cell-envelope associated acid phosphatase* | *0* | *0* | 5 | 8 |
| *F2MTN5* | *pmi* | *Mannose-6-phosphate isomerase* | *0* | *0* | *4* | *8* |
| F2MSL7 | opuCC | Glycine/betaine/carnitine/choline ABC superfamily ABC transporter, binding protein | 0 | 0 | 3 | 7 |
| F2MU67 | | Transcriptional regulator | 0 | 0 | 6 | 6 |
| F2MS22 | proS | Proline--tRNA ligase | 0 | 0 | 2 | 5 |
| *F2MMR4* | *pbp1B* | *Penicillin-binding protein 1B* | *0* | *0* | *3* | *4* |
| F2MMV9 | | ABC superfamily ABC transporter, substrate-binding protein | 0 | 0 | 3 | 4 |
| xxxxxx | | SagA-His6 | 0 | 0 | 3 | 4 |
| F2MTQ3 | atpD2 | ATP synthase subunit beta | 0 | 0 | 2 | 4 |
| F2MMX1 | pabC | Aminodeoxychorismate lyase | 0 | 0 | 3 | 3 |
| F2MNF9 | | Uncharacterized protein | 0 | 0 | 3 | 3 |
| F2MQM9 | pepV | Dipeptidase PepV | 0 | 0 | 3 | 3 |
| F2MTH6 | | Uncharacterized protein | 0 | 0 | 3 | 3 |
| F2MP85 | dkgB | 2,5-diketo-D-gluconate reductase | 0 | 0 | 2 | 3 |
| F2MQ25 | | Uncharacterized protein | 0 | 0 | 2 | 3 |
| F2MRN8 | | Acyltransferase | 0 | 0 | 2 | 3 |
| F2MTE4 | gap | Glyceraldehyde-3-phosphate dehydrogenase | 0 | 0 | 2 | 3 |
| F2MU19 | | S41A family carboxy-terminal peptidase | 0 | 0 | 2 | 3 |
| F2MM97 | fusA | Elongation factor G | 0 | 0 | 2 | 2 |
| F2MNV5 | chiC | Chitinase C1 | 0 | 0 | 2 | 2 |
| F2MPG1 | tpiA | Triosephosphate isomerase | 0 | 0 | 2 | 2 |
| F2MSG8 | arcA | Arginine deiminase | 0 | 0 | 2 | 2 |
| F2MT41 | glyA | Serine hydroxymethyltransferase | 0 | 0 | 2 | 2 |
| F2MPW0 | | Decarboxylase | 10 | 28 | 0 | 0 |
| F2MR04 | | Uncharacterized protein | 9 | 17 | 0 | 0 |
| F2MMN0 | pstS | Phosphate ABC superfamily ABC transporter, binding protein | 6 | 13 | 0 | 0 |
| F2MT47 | | Fumarate reductase | 6 | 9 | 0 | 0 |
| F2MMK7 | pyk | Pyruvate kinase | 5 | 7 | 0 | 0 |
| F2MQL2 | rpoB | DNA-directed RNA polymerase subunit beta | 4 | 7 | 0 | 0 |
| F2MTJ8 | tkt | Transketolase | 3 | 7 | 0 | 0 |
| F2MMA5 | rplB | 50S ribosomal protein L2 | 3 | 6 | 0 | 0 |
| F2MP87 | gloA5 | Lactoylglutathione lyase | 3 | 6 | 0 | 0 |
| F2MQH1 | ubiD | UbiD family decarboxylase | 2 | 6 | 0 | 0 |
| F2MU24 | coaC | Phosphopantothenoylcysteine decarboxylase | 2 | 6 | 0 | 0 |

TABLE 3-continued

Proteins in *E. faecalis* OG1RF and *E. faecalis-sagA* culture supernatants identified by mass spectrometry, after in-solution digestion. Proteins listed have at least 2 unique peptides. Proteins involved

| | | | | | | |
|---|---|---|---|---|---|---|
| F2MRI2 | rplI | 50S ribosomal protein L9 | 4 | 5 | 0 | 0 |
| F2MRM7 | ClpP | ATP-dependent Clp protease proeolytic subunit | 4 | 5 | 0 | 0 |
| F2MRQ6 | leuS | Leucine--tRNA ligase | 3 | 5 | 0 | 0 |
| F2MMX0 | greA | Transcription elongation factor GreA | 2 | 5 | 0 | 0 |
| F2MNZ2 | pcp | Pyrrolidone-carboxylate peptidase | 2 | 5 | 0 | 0 |
| F2MU79 | rplK | 50S ribosomal protein L11 | 2 | 5 | 0 | 0 |
| F2MMN1 | aspC2 | Aminotransferase | 3 | 4 | 0 | 0 |
| F2MQK0 | | Choline binding protein | 3 | 4 | 0 | 0 |
| F2MQK6 | rplM | 50S ribosomal protein L13 | 2 | 4 | 0 | 0 |
| F2MQV8 | | Gfo/Idh/MocA family oxidoreductase | 2 | 4 | 0 | 0 |
| F2MT73 | infC | Translation initiation factor IF-3 | 2 | 4 | 0 | 0 |
| F2MMA3 | rplD | 50S ribosomal protein L4 | 3 | 3 | 0 | 0 |
| F2MQQ0 | prsA | Foldase protein PrsA | 3 | 3 | 0 | 0 |
| F2MR57 | pepS | Aminopeptidase PepS | 2 | 3 | 0 | 0 |
| F2MSC3 | purR | Purine operon repressor | 2 | 3 | 0 | 0 |
| F2MM66 | guaA | GMP synthase [glutamine-hydrolyzing] | 2 | 2 | 0 | 0 |
| F2MM95 | rpsL | 30S ribosomal protein S12 | 2 | 2 | 0 | 0 |
| F2MMA1 | rpsJ | 30S ribosomal protein S10 | 2 | 2 | 0 | 0 |
| F2MMA2 | rplC | 50S ribosomal protein L3 | 2 | 2 | 0 | 0 |
| F2MMA6 | rpsS | 30S ribosomal protein S19 | 2 | 2 | 0 | 0 |
| F2MMA8 | rpsC | 30S ribosomal protein S3 | 2 | 2 | 0 | 0 |
| F2MMB9 | rpsE | 30S ribosomal protein S5 | 2 | 2 | 0 | 0 |
| F2MMD3 | rpmA | 50S ribosomal protein L27 | 2 | 2 | 0 | 0 |
| F2MNV0 | pepC | Aminopeptidase C | 2 | 2 | 0 | 0 |
| F2MPA1 | rplS | 50S ribosomal protein L19 | 2 | 2 | 0 | 0 |
| F2MQT1 | fruA | PTS family fructose porter, IIABC component | 2 | 2 | 0 | 0 |
| F2MRX9 | accF | Pyruvate dehydrogenase complex E2, dihydrolipoamide acetyltransferase | 2 | 2 | 0 | 0 |
| F2MTV4 | ppaC | Probable manganese-dependent inorganic pyrophosphatase | 2 | 2 | 0 | 0 |
| F2MU40 | pepF | Oligoendopeptidase F | 2 | 2 | 0 | 0 |
| F2MUA4 | celM | M42 family glutamyl aminopeptidase | 2 | 2 | 0 | 0 |

PSM = peptide spectrum match.

TABLE 4

Proteins identified from *E. faecium* Com15 culture supernatant by mass spectrometry, after in-gel digestion. Proteins listed have at least 2 unique peptides identified. Proteins involved in peptidoglycan remodeling are italicized and bolded.

| Uniprot Accession | Gene Name | Description | # Unique Peptides | # PSMs |
|---|---|---|---|---|
| C9ALQ1 | eno | Enolase | 20 | 57 |
| *C9ASF4/C9ASF5* | *sagA* | *Secreted lipase* | *21* | *54* |
| C9AKY1 | | Periplasmic solute binding protein | 19 | 43 |
| A9AQS4 | | Extracellular solute-binding protein | 20 | 41 |
| C9AMB1 | | Sulfatase | 14 | 39 |
| C9AQT6 | | Periplasmic binding protein | 12 | 37 |
| A9ARQ9 | groEL | 60 kDa chaperonin | 17 | 36 |
| *C9APJ5* | | *Penicillin-binding protein* | *16* | *31* |
| C9API8 | | Pyruvate kinase | 15 | 31 |
| C9AQM7 | fusA | Elongation factor G | 11 | 30 |
| *C9ATH2* | | *Beta-1,4-N-acetylmuramoylhydrolase* | *13* | *29* |
| C9AQM8 | tuf | Elongation factor Tu | 13 | 27 |
| C9ATA9 | | ATP-dependent Clp protease | 15 | 26 |
| *C9AS94* | | *Mannosyl-glycoprotein endo-beta-N-acetylglucosamidase* | *11* | *26* |
| C9AMK8 | dnaK | Chaperone protein | 18 | 25 |
| C9AMB7 | pgi | Glucose-6-phosphate isomerase | 11 | 25 |
| C9ALP9 | pgk | Phosphoglycerate kinase | 11 | 24 |
| C9ALP8 | | Glyceraldehyde-3-phosphate dehydrogenase | 11 | 23 |
| C9AMG7 | | Ornithine carbamoyltransferase | 10 | 22 |
| C9AMH5 | tsf | Elongation factor TS | 12 | 19 |
| C9APB3 | | Putative uncharacterized protein | 9 | 18 |
| C9AQB2 | | Fructose-bisphosphate adolase class-II | 8 | 18 |
| C9AMN8 | tig | Trigger factor | 10 | 17 |
| C9APW8 | | Putative uncharacterized protein | 9 | 17 |
| C9ASN3 | tyrS | Tyrosine--tRNA ligase | 7 | 17 |
| *C9AP18* | | *D-alanyl-D-alanine carboxypeptidase* | *7* | *16* |
| *C9ASJ4* | | *N-acetylmuramoyl-L-alanine amidase* | *9* | *15* |
| C9AML5 | | Amino acid ABC transporter | 6 | 15 |
| C9ALB5 | | Sulfatase | 8 | 14 |

TABLE 4-continued

Proteins identified from *E. faecium* Com15 culture supernatant by mass spectrometry, after in-gel digestion.
Proteins listed have at least 2 unique peptides identified.
Proteins involved in peptidoglycan remodeling are italicized and bolded.

| Uniprot Accession | Gene Name | Description | # Unique Peptides | # PSMs |
|---|---|---|---|---|
| C9ASF9 | | ErfK/YbiS/YcfS/YnhG family protein | 7 | 14 |
| *C9AKY4* | | *Peptidoglycan-binding protein LysM* | *6* | *14* |
| C9ANA8 | | Extracellular solute-binding protein | 8 | 13 |
| C9ARE8 | prsA | Foldase protein PrsA | 6 | 13 |
| C9APM7 | | Phosphoenolpyruvate-protein phosphottransferase | 9 | 12 |
| C9AQN3 | rplB | 50S ribosomal protein L2 | 5 | 12 |
| C9AS40 | | ABC transporter substrate binding protein | 7 | 11 |
| C9ANB6 | | Extracellular solute-binding protein | 6 | 11 |
| C9AL01 | | Extracellular solute-binding protein | 5 | 11 |
| C9ARP7 | | Glycine betaine/L-proline ABC transporter | 4 | 11 |
| C9AQZ1 | pnp | Polyribonucleotide nucleotidyltransferase | 4 | 11 |
| C9AQB4 | | Glutamine synthetase | 6 | 10 |
| C9APW3 | | Putative uncharacterized protein | 5 | 10 |
| C9APC1 | tuf | Elongation factor Tu | 5 | 10 |
| C9APP1 | | Chitin-binding protein | 4 | 10 |
| C9ANY2 | | Transketolase | 4 | 10 |
| C9ATC6 | | Uncharcatreized protein | 3 | 10 |
| *C9ANP2* | | *N-acetylmiramoyl-L-alanine amidase* | *5* | *9* |
| *C9ARY2* | | *Cell wall surface adhesion protein* | *6* | *8* |
| C9ATC3 | | Uncharacterized protein | 6 | 8 |
| C9ALV5 | | UTP-glucose-1-phosphate uridyltransferase | 4 | 8 |
| C9AQ24 | ileS | Isoleucine--tRNA ligase | 3 | 8 |
| C9ALL0 | | Putative uncharacterized protein | 6 | 7 |
| C9ASG0 | ldh | L-lactate dehydrogenase | 5 | 7 |
| C9ANG6 | arcA | Arginine deiminase | 5 | 7 |
| C9AQK7 | guaA | GMP synthase [glutamine-hydrolyzing] | 5 | 7 |
| C9ARS4 | nadE | NH(3)-dependent NAD(+) synthtase | 5 | 7 |
| C9APR1 | | Predicted protein | 4 | 7 |
| C9ARL2 | rplK | 50S ribosomal protein L11 | 4 | 7 |
| C9AS47 | | Ferritin | 4 | 7 |
| C9ALR9 | atpD | ATP synthetase subunit beta | 4 | 7 |
| C9APW2 | | Predicted protein | 3 | 7 |
| C9APL9 | acpP | Acyl carrier protein | 3 | 7 |
| C9ATD5 | | Intracellular protease | 3 | 7 |
| C9AS03 | metG | Methionine--tRNA ligase | 2 | 7 |
| C9ANN9 | | NADH oxidase | 2 | 7 |
| C9AL85 | prsA | Foldase protein PrsA | 6 | 6 |
| C9AQL4 | | Basic membrane lipoprotein | 5 | 6 |
| C9AS42 | rpoC | DNA-directed RNA polymerase subunit beta' | 5 | 6 |
| C9AS49 | rpsI | 30S ribosomal protein S9 | 4 | 6 |
| C9APA2 | | Peptidase M20A | 4 | 6 |
| C9ANY3 | | Pyruvate dehydrogenase | 3 | 6 |
| C9AQP6 | rplR | 50S ribosomal protein L18 | 3 | 6 |
| C9AKW7 | | NAD(FAD)-dependent dehydrogenase | 3 | 6 |
| C9AR84 | | Glutamyl aminopeptidase | 3 | 6 |
| C9ALQ0 | tpiA | Triosephosphate isomerase | 3 | 6 |
| C9ALX9 | | Phosphoglucomutase/phosphomannomutase | 3 | 6 |
| C9ATF4 | | Citrate lyase alpha subunit | 3 | 6 |
| C9AQP9 | rplO | 50S ribosomal protein L15 | 2 | 6 |
| C9AN96 | | Alkyl hydroperoxide reductase | 2 | 6 |
| C9APR5 | greA | Transcription elongation factor GreA | 2 | 6 |
| C9ALV9 | | Catabolite control protein A | 4 | 5 |
| C9ASA9 | gltX | Glutamate--tRNA ligase | 4 | 5 |
| C9ANQ4 | | Glyceraldehyde-3-phosphate dehydrogenase | 3 | 5 |
| C9API9 | pfkA | 6-phosphofructokinase | 3 | 5 |
| C9ASH2 | lysS | Lysine--tRNA ligase | 3 | 5 |
| C9AQ07 | | Predicted protein | 3 | 5 |
| C9ANY1 | | Dehydrolipoamide S-succinyltransferase | 2 | 5 |
| C9ASN4 | | Putative uncharacterized protein | 2 | 5 |
| C9ARP9 | | DegV family protein | 2 | 5 |
| C9ARL5 | rplL | 50S ribosomal protein L7/L12 | 4 | 4 |
| C9ARQ8 | groES | 10 kDa chaperonin | 4 | 4 |
| C9AS41 | rpoB | DNA-directed RNA polymerase subunit beta | 4 | 4 |
| C9AQF3 | guaB | Inosine-5'-monophosphate dehydrogenase | 4 | 4 |
| C9AT02 | | Uncharacterized protein | 3 | 4 |
| C9AP93 | | DNA binding protein HU | 3 | 4 |
| C9AMH4 | rpsB | 30S ribosomal protein S2 | 3 | 4 |
| C9ANQ7 | | Peptidyl-prolyl cis-trans isomerase | 3 | 4 |
| C9ART9 | | Sulfatase | 3 | 4 |
| C9AQ23 | zwf | Glucose-6-phosphate 1-dehydrogenase | 3 | 4 |
| C9AQM2 | gpmA | 2,3-bisphosphoglycerate-dependent phosphoglycerate nutase | 2 | 4 |

TABLE 4-continued

Proteins identified from *E. faecium* Com15 culture supernatant by mass spectrometry, after in-gel digestion.
Proteins listed have at least 2 unique peptides identified.
Proteins involved in peptidoglycan remodeling are italicized and bolded.

| Uniprot Accession | Gene Name | Description | # Unique Peptides | # PSMs |
| --- | --- | --- | --- | --- |
| C9AL78 | | Cell wall surface anchor family protein | 2 | 4 |
| C9AQN6 | rpsC | 30S ribosomal protein S3 | 2 | 4 |
| C9APL6 | | 3-oxoacryl-[acyl-carrier-protein] synthase 2 | 2 | 4 |
| C9APQ3 | | Superoxide dismutase | 2 | 4 |
| C9AQP1 | rplX | 50S ribosomal protein L24 | 2 | 4 |
| C9AR81 | | Peptidase M20A | 2 | 4 |
| C9AR88 | | Peptidase S1 | 2 | 4 |
| *C9AM29* | | *D-alanyl-D-alanine carboxypeptidase* | *2* | *4* |
| C9AP08 | xpt | Xanthine phosphoribosyltransferase | 2 | 4 |
| C9AKX7 | | Putative uncharacterized protein | 3 | 3 |
| C9AP14 | | 6-phosphogluconate dehydrogenase, decarboxylating | 3 | 3 |
| C9ALU9 | | Putative uncharacterized protein | 3 | 3 |
| C9AP54 | ppaC | Probable manganese-dependent inorganic pyrophosphatase | 3 | 3 |
| C9AQR6 | | Dak phosphatase | 3 | 3 |
| *C9APV0* | | *N-acetylmuramoyl-L-alanine amidase* | *2* | *3* |
| C9ARH9 | | Acyltransferase | 2 | 3 |
| C9ANY0 | | Dihydrolipoyl dehydrogenase | 2 | 3 |
| C9ANP3 | | Transketolase | 2 | 3 |
| C9AS48 | rplM | 50S ribosomal protein L13 | 2 | 3 |
| C9APV4 | | Putative uncharacterized protein | 2 | 3 |
| C9AP95 | | Ribosomal protein S1 | 2 | 3 |
| C9AM30 | | Putative uncharacterized protein | 2 | 3 |
| C9AQ25 | | DivIVA protein | 2 | 3 |
| C9ANX7 | | GTP-binding protein TypA | 2 | 3 |
| C9APW1 | | Predicted protein | 2 | 3 |
| *C9AS27* | | *Cell surface protein (Fragment)* | *2* | *3* |
| C9AQ61 | rplU | 50S ribosomal protein L21 | 2 | 2 |
| C9AQZ7 | rplY | 50S ribosomal protein L25 | 2 | 2 |
| C9AQQ1 | adk | Adenylate kinase | 2 | 2 |
| C9ALR7 | atpA | ATP synthase subunit alpha | 2 | 2 |
| C9ALT5 | | Sigma 54 modulation protein/ribosomal protein S30EA | 2 | 2 |
| C9AQN4 | rpsS | 30S ribosomal protein S19 | 2 | 2 |
| C9ARJ0 | | Peptidase M3B | 2 | 2 |
| C9AMQ2 | gatB | Aspartyl/glutamyl-tRNA(Asn/Gln) amidotransferase subunit B | 2 | 2 |

PSM = peptide spectrum match.

Example 2

This Example expands on Example 1, and provides an analysis of how colonization of mice with a human commensal *Enterococcus faecium* strain affects susceptibility to *Salmonella* infection. The data demonstrate that *E. faecium* improves host intestinal epithelial barrier function and limits *Salmonella* pathogenesis. This protection requires host antimicrobial peptide (AMP) production and innate immune receptor expression in epithelial cells. Ectopic expression of SagA by non-protective bacteria is sufficient to induce AMP expression and confer enhanced activity against *Salmonella* pathogenesis. This Example demonstrates that a specific factor produced by *E. faecium* triggers a protective program in the mammalian intestinal epithelium, revealing both host and bacterial mechanisms for commensal bacteria-mediated pathogen resistance.

Figure 16:
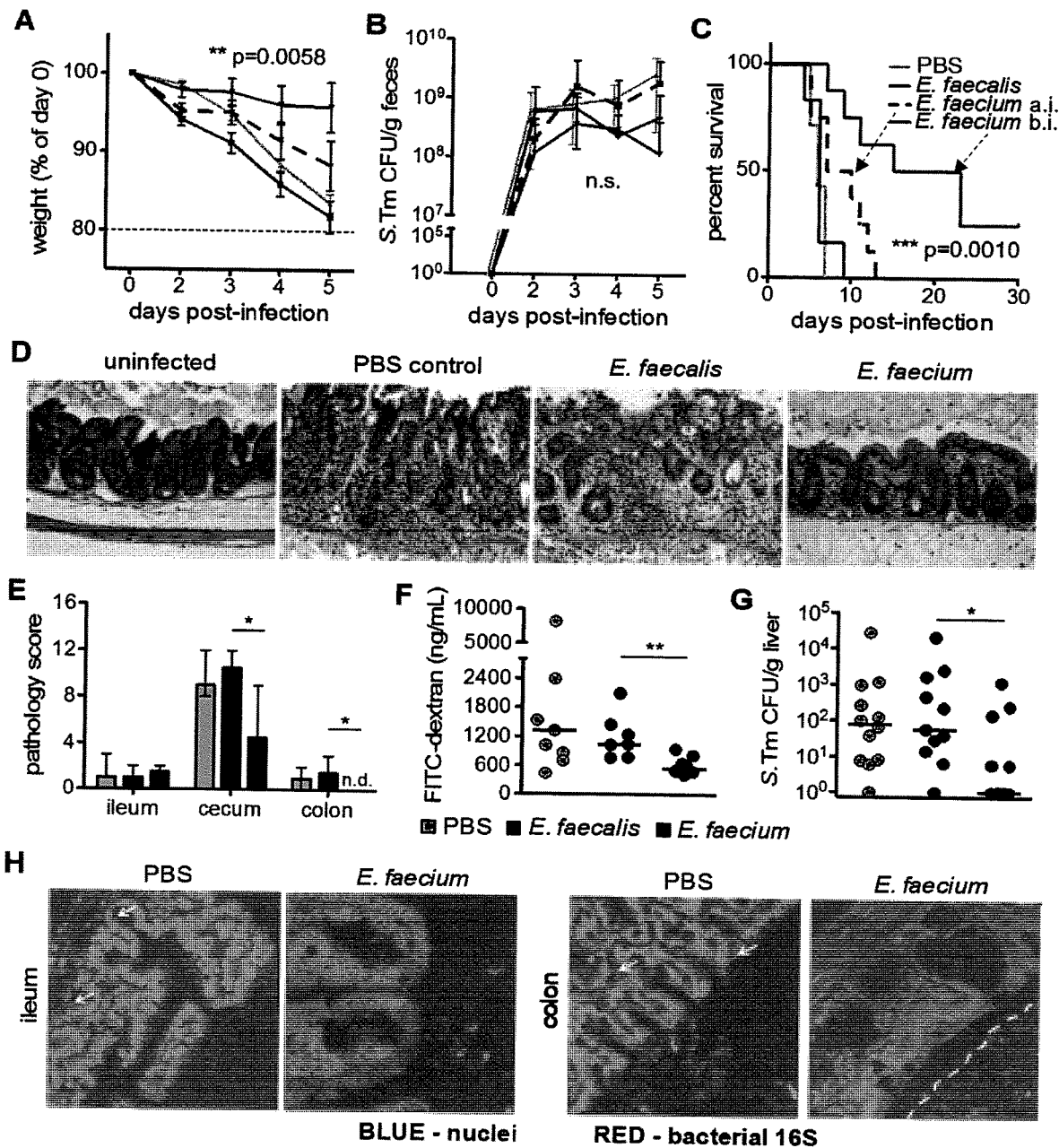
FIG. 16. E. faecium enhances pathogen resistance and intestinal epithelial barrier integrity. (A-C) C57BL/6 mice were orally gavaged with streptomycin and given $10^8$ colony-forming units (CFU) E. faecalis or E. faecium 4 h before (b.i.) or 24 h after (a.i.) oral infection with $10^6$ CFU *S. Typhimurium*. (A) Weight loss, (B) *S. Typhimurium* (*S. Tm*) bacterial burden in feces, and (C) survival are shown. Pooled data from 3 independent experiments, n=6-8 mice/group. (D) Cecum tissue stained with H&E, harvested at 48 h post-infection (p.i.) from mice given streptomycin and left uninfected or treated before infection as in (A-C). Representative images, 40× objective, from 1 of 3 independent experiments, n=2-3 mice/group. (E) Ileum, cecum, and colon tissues were harvested and prepared as in (D) and scored for 4 pathology parameters. Pooled combined pathology scores from 3 independent experiments, n=6-7 mice/group. (F) Intestinal permeability measured by FITC-dextran concentration in the serum 48 h p.i. from mice treated before infection as in (A-C). Pooled data from 3 independent experiments, n=7-9 mice/group. (G) *S. Tm* bacterial burden 48 h p.i. in the livers of mice treated before infection as in (A-C). Pooled data from 4 independent experiments, n=11-12 mice/group. (H) FISH staining for all bacteria (red, universal 16S probe) and epithelial nuclei (blue, Hoechst) from intestinal tissues 48 h p.i. from mice treated before infection as in A-C). Representative images, 40× objective, from 1 of 3 independent experiments, n=4-6 mice/group. White arrows indicate bacteria in contact with or invading through the epithelium, and white dashed line designates zone of segregation from bacteria. (A and B) mean±SEM, 2-way ANOVA, p-value shown comparing *E. faecalis* to *E. faecium* b.i., n.s.=not significant. (C) Log-rank analysis, p-value shown comparing *E. faecalis* to *E. faecium* b.i. (E) median±range, Mann-Whitney comparing *E. faecalis* to *E. faecium* (Wilcoxon for colon, n.d.=none detected, score of zero). (F and G) bar=median, Mann-Whitney comparing *E. faecalis* to *E. faecium*. *p<0.05, p≤0.01, *p≤0.001 for all analyses.
Figure 20:
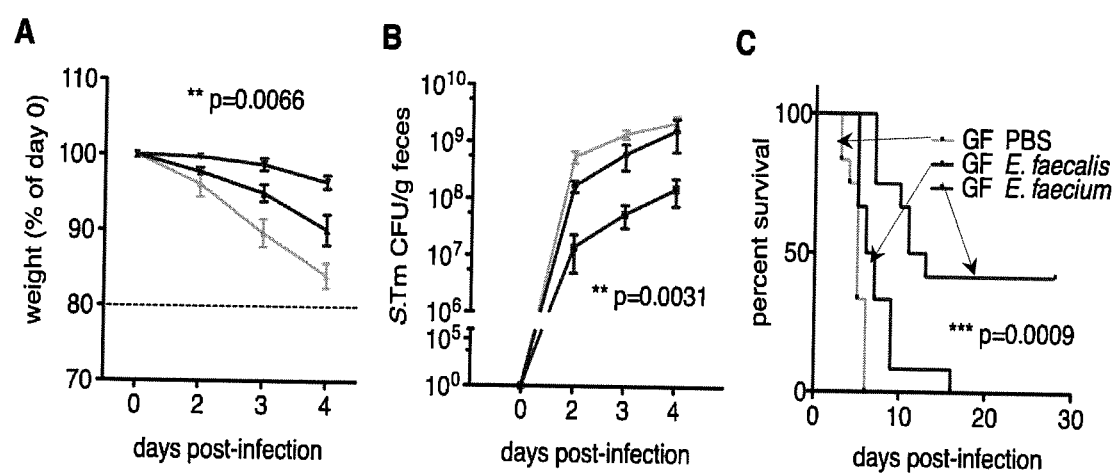
FIG. 20. *E. faecium* is protective in mono-colonized gnotobiotic mice. Germ-free (GF) C57BL/6 mice were orally gavaged with $10^8$ CFU *E. faecalis* or *E. faecium* 7 d before oral infection with $10^2$ CFU S. Tm. (A) Weight loss, (B) S. Tm bacterial burden in feces, and (C) survival are shown. Pooled data from 4 independent experiments, n=12 mice/group. (A and B) mean±SEM, 2-way ANOVA, p-value shown comparing E. faecalis to E. faecium. (C) Log-rank analysis, p-value shown comparing E. faecalis to E. faecium. p≤0.01 and *p≤0.001 for all analyses.
Figure 21:
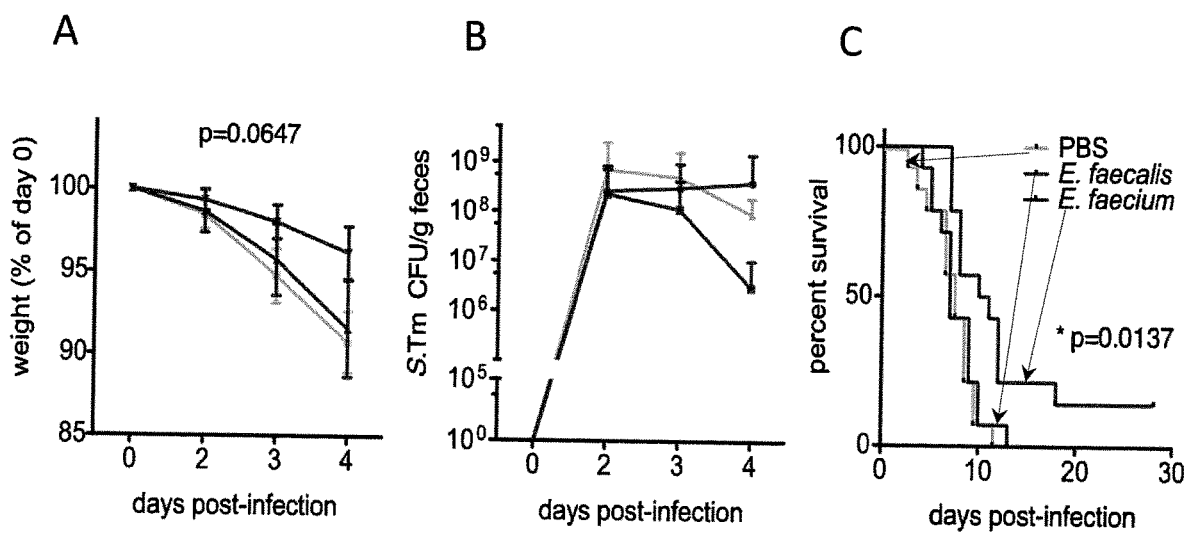
FIG. 21. E. faecium is protective in broad-spectrum antibiotic-treated mice. C57BL/6 mice were orally gavaged with a broad-spectrum antibiotic cocktail of ampicillin, metronidazole, neomycin, and vancomycin (AMNV) daily for 7 d prior to gavage with $10^8$ CFU E. faecalis or E. faecium or PBS, followed by infection with $10^6$ S. Tm. (A) Weight loss, (B) S. Tm bacterial burden in feces, and (C) survival are shown. Pooled data from 4 independent experiments, n=14 mice/group. (A and B) mean±SEM, 2-way ANOVA, p-value shown comparing E. faecalis to E. faecium. (C) Log-rank analysis, p-value shown comparing E. faecalis to E. faecium. *p<0.05.

To analyze protective capacity of *E. faecium* (human isolate, strain Com15), we compared it to *E. faecalis* (strain OG1RF), in a non-typhoidal *Salmonella enterica* serotype Typhimurium infection model. Mice treated with a single dose of streptomycin are rendered highly susceptible to *S.* Typhimurium infection. As expected, streptomycin-treated control and *E. faecalis*-colonized mice showed severe *S.* Typhimurium-induced pathogenesis, as evidenced by rapid weight loss and mortality within 10 days of infection (FIG. 16A and C). In contrast, streptomycin-treated mice pre-colonized with *E. faecium* displayed significantly reduced early weight loss and prolonged survival, without changes in pathogen burden over the course of infection (FIG. 16A-C). Of note, administration of *E. faecium* 24 hours after *S.* Typhimurium infection also conferred some protective effects, albeit greatly reduced compared to *E. faecium* administered as little as 4 hours before infection (FIG. 16, A and C), indicating that *E. faecium* colonization rapidly induces a protective response. Protection was not dependent on secondary effects on the remaining microbiota, as *E. faecium* was also protective in mono-colonized, *S.* Typhimurium-infected gnotobiotic mice (FIG. 20A-C) and in mice pre-treated with a broad-spectrum antibiotic cocktail (FIG. 21A-C) from which no bacterial 16S rRNA could be amplified (data not shown). Furthermore, *E. faecium* did not affect *S.* Typhimurium proliferation (FIG. 16B) or secretion of type III protein effectors involved in *S.* Typhimurium invasion of host cells as described in Example 1. These results indicate that *E. faecium* does not act by bactericidal mechanisms, inhibiting *S.* Typhimurium virulence, or indirectly modulating the microbiota.

Figure 22:
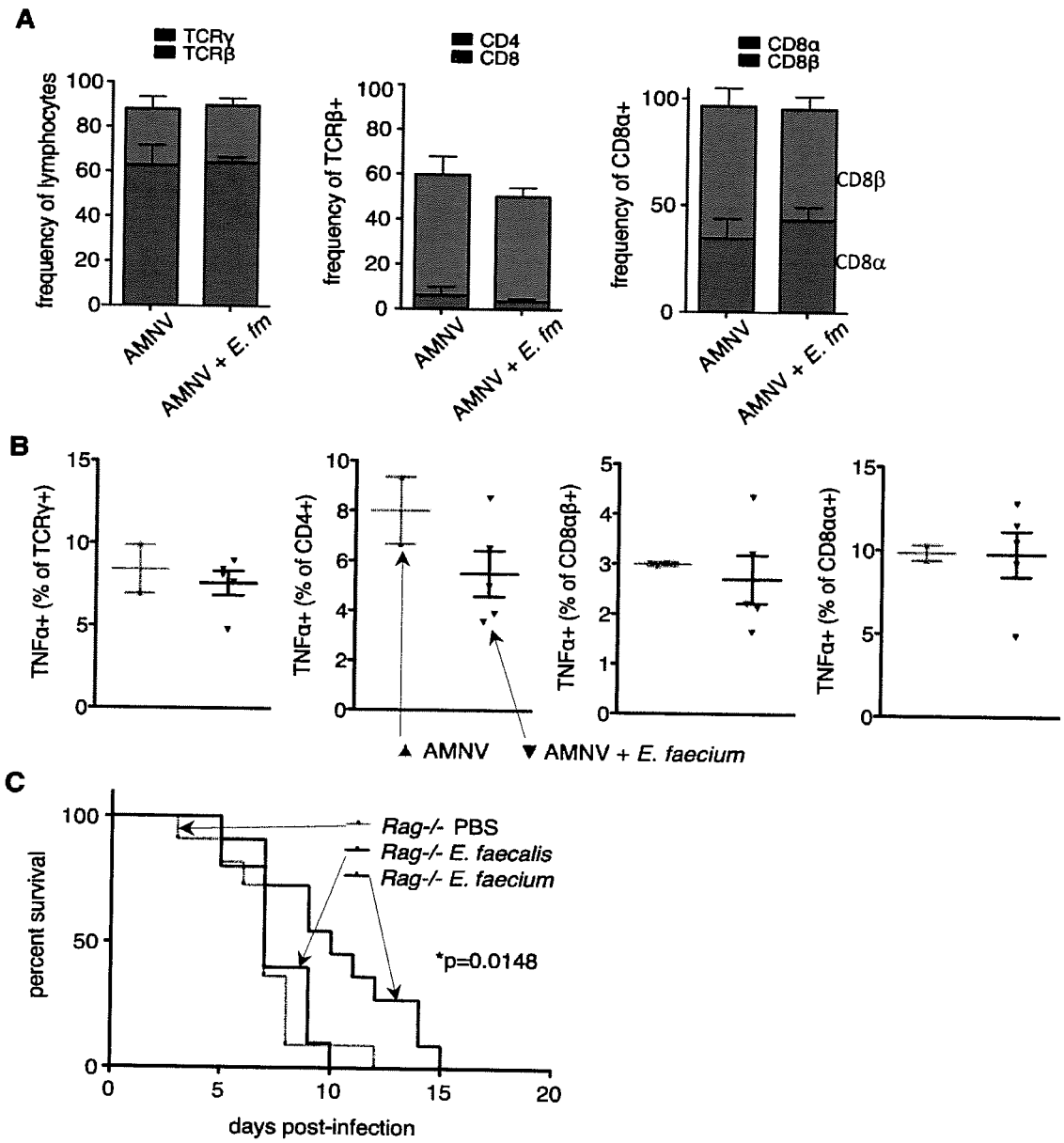
FIG. 22. E. faecium-mediated protection does not require an adaptive immune response. (A and B) C57BL/6 mice were gavaged with a broad-spectrum antibiotic cocktail of ampicillin, metronidazole, neomycin, and vancomycin (AMNV) daily for 7 d prior to gavage with $10^8$ CFU E. faecium. 5 d post-colonization, intraepithelial lymphocytes were isolated and analyzed by flow cytometry for (A) relative frequency of shown subpopulations and (B) cytokine profile. Pooled data from 2 independent experiments, n=2-5 mice/group. (C) Rag1-/-/- mice were gavaged with AMNV daily for 7 d prior to gavage with $10^8$ CFU E. faecalis or E. faecium or PBS, followed by infection with $10^6$ S. Tm. Pooled data from 4 independent experiments, n=13-14 mice/group. (C) Log-rank analysis, p-value shown comparing E. faecalis to E. faecium. *p≤0.05.

To investigate host mechanisms involved in *E. faecium*-mediated protection against *S.* Typhimurium pathogenesis in vivo, we analyzed intestinal lymphocytes after *E. faecium* colonization. *E. faecium* colonization did not induce significant changes in the relative frequency or cytokine profile of intestinal intraepithelial lymphocyte subsets (FIGS. 22, A and B). In addition, prolonged host survival in response to E. faecium colonization was preserved in RagI$^{-/-}$ mice, which lack B and T cells (FIG. 22C). Together with the speed of E. faecium's effects (FIGS. 16, A and C), and without intending to be constrained by any particular concept, these data suggest that an adaptive immune response is dispensable for E. faecium-mediated protection. S. Typhimurium produces several effector proteins that disrupt the intestinal epithelium and facilitate bacterial invasion to systemic tissues, such as the liver. We therefore analyzed intestinal tissues at an early time (48 hours) post-infection. Control and E. faecalis-colonized mice exhibited severe edema, neutrophil infiltration, and destruction of intestinal epithelial integrity upon S. Typhimurium infection, while these effects, particularly epithelial damage, were markedly reduced in E. faecium pre-treated mice (FIGS. 16D and E). E. faecium colonization also attenuated S. Typhimurium-induced intestinal paracellular permeability (FIG. 16F), which corresponded to decreased incidence of early invasion of S. Typhimurium into the liver (FIG. 16G). In addition, fluorescence in situ hybridization (FISH) showed improved bacterial segregation from the intestinal epithelium in E. faecium-colonized mice compared to controls (FIG. 16H), with bacterial contact and invasion into the lamina propria much more apparent in untreated mice. This decreased bacterial contact with the epithelium could be sufficient to limit S. Typhimurium disruption of epithelial tight junctions and invasion of peripheral organs. Taken together, these data indicate that E. faecium does not utilize adaptive immune mechanisms, but rather stimulates protective effects in the intestinal epithelium that are associated with prolonged survival and decreased S. Typhimurium invasion in vivo.

Figure 17:
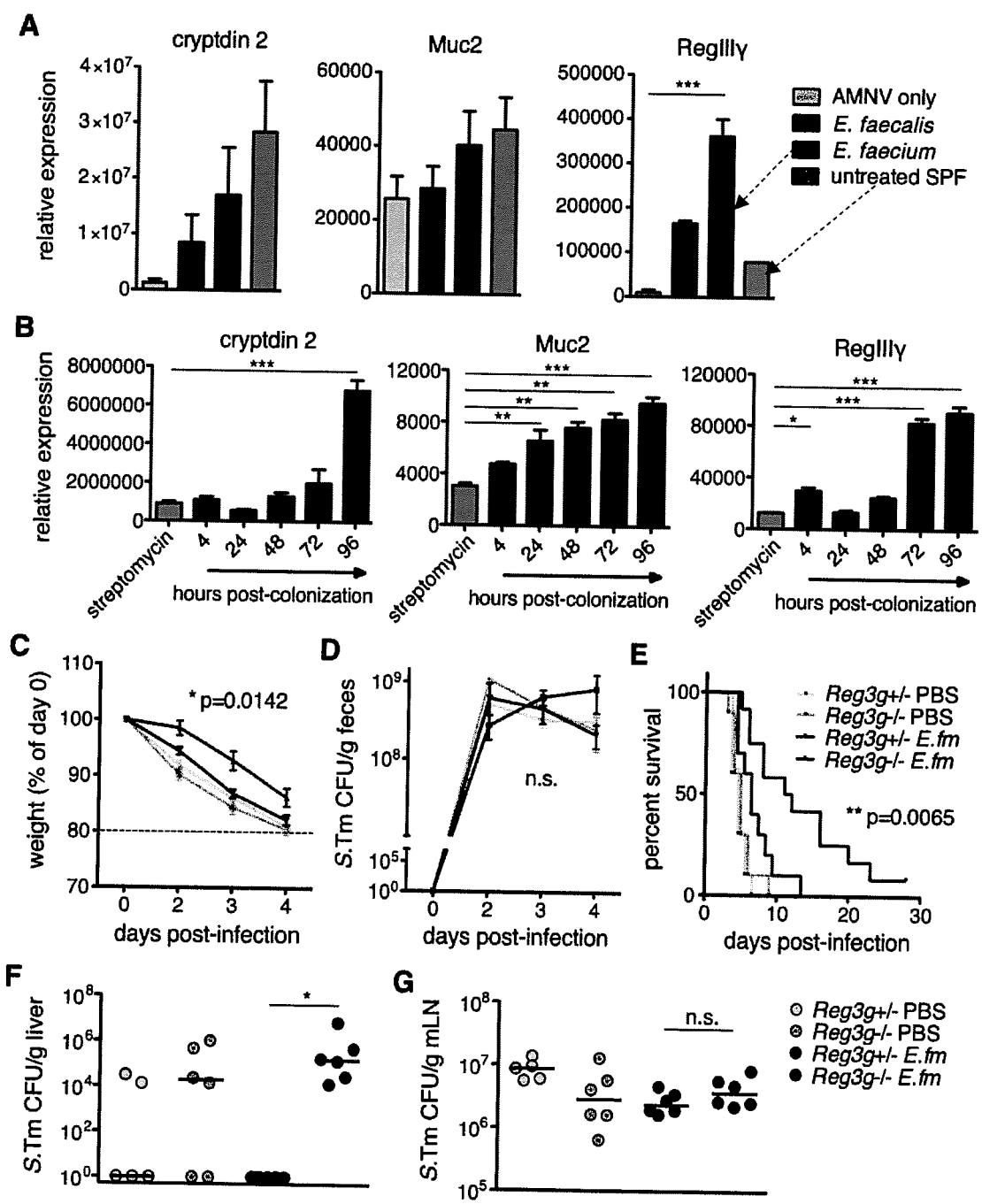
FIG. 17. *E. faecium*-induced expression of Reg3g is required for protection against *S. Typhimurium*. (A) C57BL/6 mice were orally gavaged with a broad-spectrum antibiotic cocktail of ampicillin, metronidazole, neomycin, and vancomycin (AMNV) daily for 7 d prior to gavage with $10^8$ CFU *E. faecalis* or *E. faecium*. 4 d post-colonization, intestinal epithelial cells (IECs) were isolated and analyzed by RQ-PCR for expression of shown genes vs unmanipulated specific pathogen-free (SPF) mice. Representative data from 1 of 3 independent experiments, n=2-3 mice/group. (B) Mice were given a single gavage of streptomycin followed by gavage with $10^8$ CFU *E. faecium* 24 h later. At indicated time-points post-colonization, IECs were isolated and analyzed by RQ-PCR. Representative data from 1 of 2 independent experiments, n=2 mice/group. (C-E) Reg3g–/– mice or +/– littermate controls were given AMNV for 7 d and colonized with *E. faecium* (*E. fm*) prior to oral infection with $10^6$ *S. Tm*. (C) Weight loss, (D) *S. Tm* bacterial burden in feces, and (E) survival are shown. Pooled data from 4 independent experiments, n=10-12 mice/group. (F) *S. Tm* bacterial burden 72 h p.i. in the livers or (G) mesenteric lymph nodes (mLN) of Reg3g–/– or +/– littermate controls treated before infection as in (C-E). Pooled data from 2 independent experiments, n=5-6 mice/group. (A and B) mean±SEM, 1-way ANOVA with Dunnett's post-test comparing all to antibiotic-only controls. (C and D) mean±SEM, 2-way ANOVA, p-value shown comparing Reg3g–/– *E. fm* to Reg3g+/– *E. fm*, n.s.=not significant. (E) Log-rank analysis, p-value shown comparing Reg3g–/– *E. fm* in to Reg3g+/– *E. fm*. (F and G) bar=median, Wilcoxon (F) and Mann-Whitney (G) comparing Reg3g–/– *E. fm* to Reg3g+/– *E. fm*. *p≤0.05, p≤0.01, *p<0.001 for all analyses.
Figure 23:
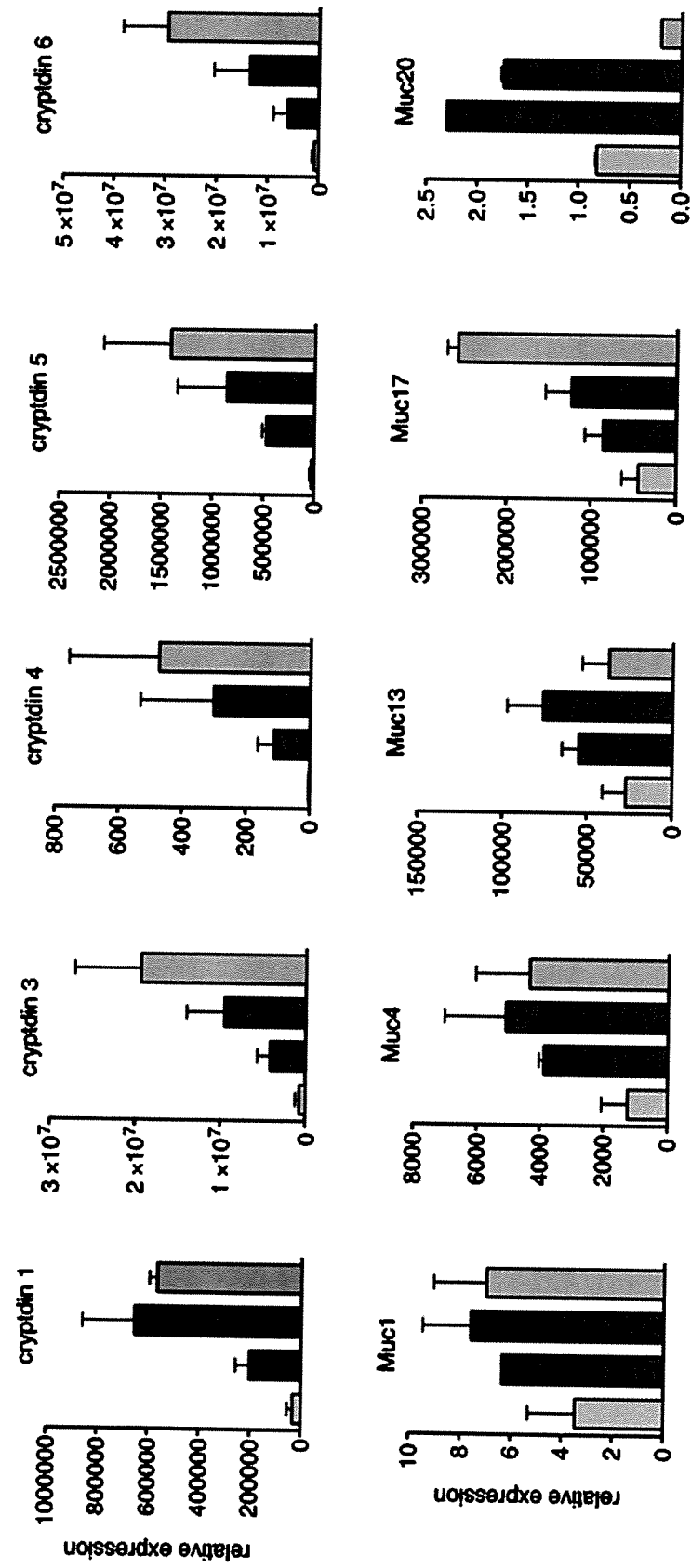
FIG. 23. E. faecium elicits upregulation of antimicrobial peptides (AMPs). C57BL/6 mice were orally gavaged with a broad-spectrum antibiotic cocktail of ampicillin, metronidazole, neomycin, and vancomycin (AMNV) daily for 7 d prior to gavage with $10^8$ CFU E. faecalis or E. faecium. 4d post-colonization, intestinal epithelial cells (IECs) were isolated and analyzed by RQ-PCR for expression of shown genes vs unmanipulated specific pathogen-free (SPF) mice. Representative data from 1 of 3 independent experiments, n=2-3 mice/group.

Given the preservation of intestinal barrier integrity upon E. faecium colonization, we next examined E. faecium-induced changes in intestinal epithelial cell (IEC) gene expression. In the presence of microbial colonization, IECs produce numerous proteins that function to restrict bacterial contact with the epithelium and prevent bacterial overgrowth, including antimicrobial peptides (AMPs), such as α-defensins (cryptdins in mice) and the C-type lectins RegIIIβ and RegIIIγ, and mucous components like mucins. Expression of many AMP and mucin genes is markedly reduced in response to antibiotic treatment; however, we observed that E. faecium colonization after broad-spectrum antibiotic treatment restored expression to pre-antibiotic levels and increased expression of the C-type lectin Reg3g (RegIIγ) (FIG. 17A and FIG. 23). The induction of Reg3g above steady-state levels suggests that E. faecium-derived signals are especially capable of prompting expression of certain AMPs. This increase was also present in streptomycin-treated, E. faecium-colonized mice (FIG. 17B), and consistent with the protection observed against S. Typhimurium infection (FIGS. 16, A and C), significant AMP expression was induced as early as 4 hours post-colonization.

The expression of Reg3g has been shown to play an important role in excluding bacteria from the epithelial surface, although neither RegIIIβ nor RegIIIγ are bactericidal to S. Typhimurium. To determine the relevance of the observed increase in expression of Reg3g to E. faecium-mediated protection, we colonized antibiotic-treated Reg3g-deficient(Reg3g$^{-/-}$) mice and infected them with S. Typhimurium. Absence of Reg3g significantly abrogated E. faecium-mediated protection against S. Typhimurium pathogenesis compared to Reg3g$^{+/-}$ controls (FIG. 17C-E), while un-colonized Reg3g$^{-/-}$ and heterozygous littermate controls were equally susceptible to S. Typhimurium-induced weight loss and mortality. Collectively, these findings signify that E. faecium stimulates IEC expression of relevant AMPs like Reg3g, which is required for faecium-mediated protection against S. Typhimurium pathogenesis.

S. Typhimurium dissemination to peripheral organs like the liver can occur by invasion across IECs, disruption of tight junctions, or by unimpeded transport through microfold (M) cells. However, bacteria that are sampled through M cells are likely to be taken up by mononuclear phagocytes in the underlying Peyer's patches (PPs) and transported to the mesenteric lymph nodes (mLN). In Reg3g$^{+/-}$ mice, colonization with E. faecium prevented early S. Typhimurium invasion into the liver, whereas Reg3g-deficient mice suffered liver invasion comparable to untreated mice (FIG. 17F). However, translocation of bacteria to the mLN was not affected by colonization or genotype (FIG. 17G). This implies that E. faecium does not affect phagocyte migration or active transport of Salmonella, but rather acts on the level of IEC integrity.

Figure 18:
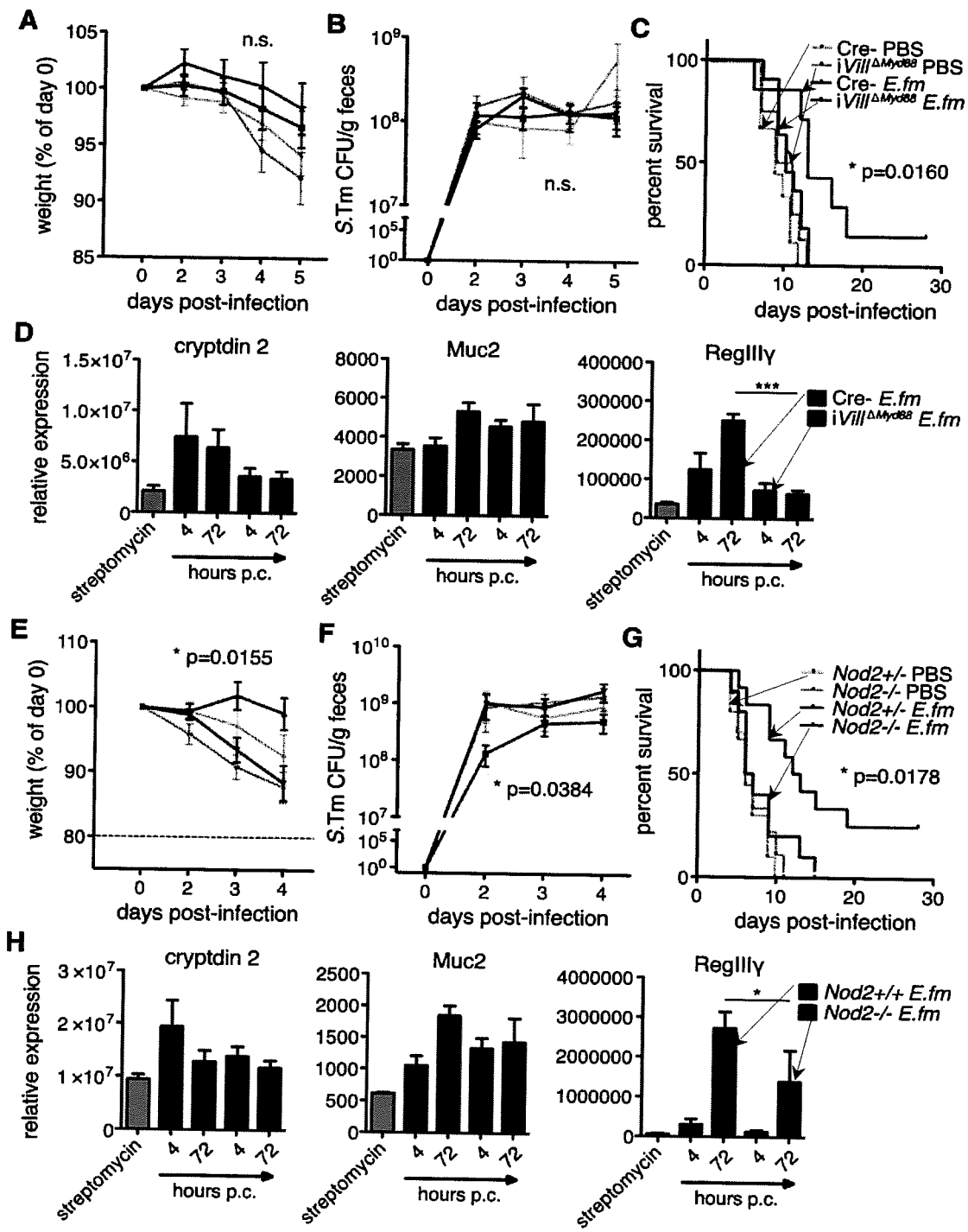
FIG. 18. MyD88 and NOD2 are required for AMP induction and *E. faecium*-mediated protection. (A-C) iVillΔMyd88 or Cre⁻(MyD88$^{f/f}$) littermate control mice were injected with tamoxifen 7 days prior to oral gavage with streptomycin. After 24 h, mice were gavaged with $10^8$ CFU *E. fm* followed 4 h later by oral infection with $10^6$ CFU *S. Tm*. (A) Weight loss, (B) *S. Tm* bacterial burden in feces, and (C) survival are shown. Pooled data from 3 independent experiments, n=7-11 mice/group. (D) Mice were treated and colonized as in (A-C). At 4 and 72 h post-colonization (p.c.), IECs were isolated and analyzed by RQ-PCR for expression of shown genes. Pooled data from 2 independent experiments, n=2-4 mice/group. (E-G) Nod2–/– mice or +/– littermate controls were gavaged with streptomycin 24 h prior to gavage with $10^8$ CFU *E. fm* followed 4 h later by oral infection with $10^6$ CFU *S. Tm*. (E) Weight loss, (F) *S. Tm* bacterial burden in feces, and (G) survival are shown. Pooled data from 4 independent experiments, n=9-12 mice/group. (H) Mice were treated and colonized as in (E-G). At 4 and 72 h post-colonization (p.c.), IECs were isolated and analyzed by RQ-PCR for expression of shown genes. Pooled data from 2 independent experiments, n=2-4 mice/group. (A, B, E, and F) mean±SEM, 2-way ANOVA, p-value shown comparing *E. fm*-colonized deficient to sufficient controls, n.s.=not significant. (C and G) Log-rank analysis, p-value shown comparing *E. fm*-colonized deficient to sufficient controls. (D and H) mean±SEM, 1-way ANOVA with Dunnett's post-test comparing all to streptomycin-only controls. *p≤0.05 and ***p≤0.001 for all analyses.
Figure 24:
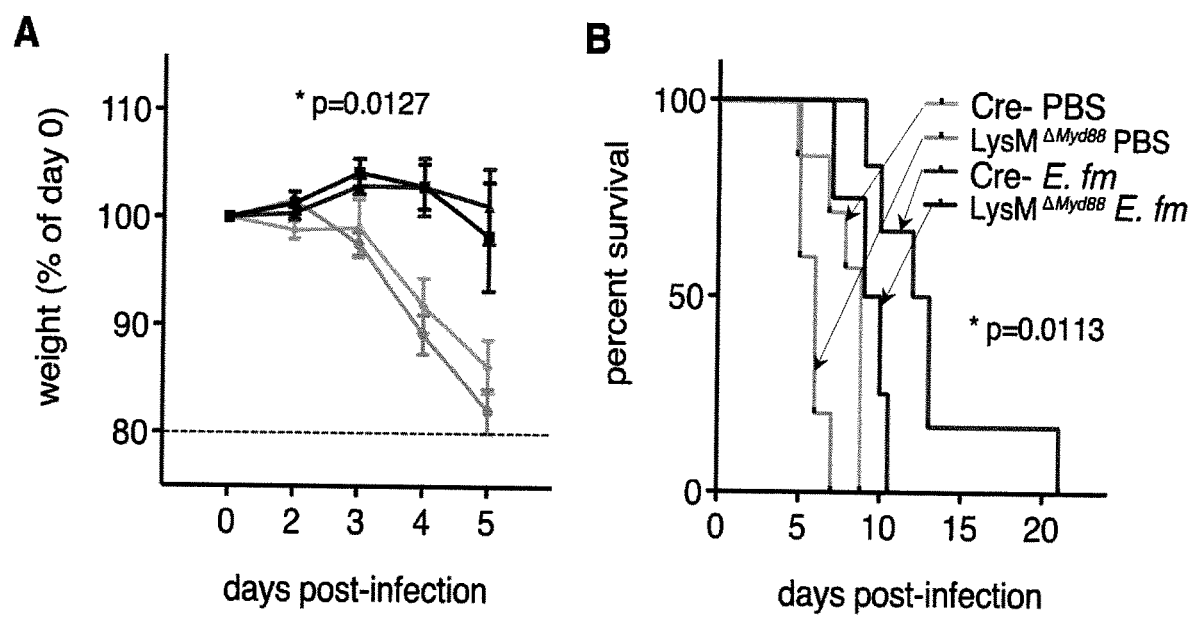
FIG. 24. E. faecium is protection is maintained in the absence of MyD88 signaling myeloid cells. LysMΔMyd88 or Cre⁻ (MyD88$^{f/f}$) littermate control mice were gavaged with streptomycin 24 h prior to gavage with $10^8$ CFU E. fm followed 4 h later by oral infection with $10^6$ CFU S. Tm. (A) Weight loss, and (B) survival are shown. Pooled data from 2 independent experiments, n=4-7 mice/group. (A) mean±SEM, 2-way ANOVA, p-value shown comparing E. faecium LysMΔMyd88 to E. faecium Cre⁻ controls. (B) Log-rank analysis, p-value shown comparing E. faecium LysMΔMyd88 to E. faecium Cre⁻ controls. *p≤0.05 for all analyses.

Expression of AMPs in the intestinal epithelium is upregulated in response to signaling through a number of pattern recognition receptors (PRRs). Specifically, toll-like receptors (TLRs) and their signaling adapter, MyD88, have are known to be required for IEC expression of Muc2, Reg3b, and Reg3g. We therefore examined the requirement for MyD88 signaling in E. faecium-mediated protection by generating a tamoxifen-inducible, IEC-specific conditional MyD88 knockout mouse (Villin$^{CreERT2}$xMyd88$^{f/f}$ (iVillΔMyd88)). We administered tamoxifen to iVillΔMyd88 and Cre$^-$ littermate controls one week prior to streptomycin treatment and followed this with E. faecium colonization and subsequent S. Typhimurium infection. We observed no significant difference in early weight loss or pathogen burden between iVillΔMyd88 and Cre$^-$ mice (FIGS. 18, A and B); however, E. faecium-mediated prolonged host survival was abrogated in the absence of epithelial MyD88 expression (FIG. 18C). Furthermore, E. faecium-induced expression of some AMPs, particularly Defa2 (cryptdin 2) and Reg3g, was impaired in iVillΔMyd88 IECs (FIG. 18D). While macrophages are known to play a major role in S. Typhimurium pathogenesis and clearance, conditional deletion of MyD88 in myeloid cells, in particular macrophages, by interbreeding Myd88$^{f/f}$ with Lyz2$^{Cre}$ mice (LysMΔMyd88) still allowed for a significant survival benefit of E. faecium colonization prior to S. Typhimurium infection (FIGS. 24A and B). This benefit was evident despite a distinct increase in susceptibility to S. Typhimurium in mice harboring MyD88-deficient myeloid cells. These data indicate that E. faecium-mediated protection requires MyD88 signaling in IECs for improved survival and proper upregulation of RegIIIγ, and they further suggest that E. faecium enhances host epithelial barrier function rather than affecting immune cell responses to S. Typhimurium.

To investigate the contribution of NOD2 to E. faecium-induced protection and AMP expression, we compared the efficacy of E. faecium colonization in streptomycin-treated Nod2-deficient mice (Nod2$^{-/-}$) and heterozygous littermate controls. E. faecium-mediated protection was absent in Nod2$^{-/-}$ animals in terms of early weight loss, pathogen burden, and survival (FIG. 18E-G). While induction of Defa2 and Muc2 expression was mostly maintained, Reg3g upregulation was significantly impaired in Nod2$^{-/-}$ mice (FIG. 18H). Together, these data signify that the signaling adapters and receptors known to contribute to Reg3g and AMP expression, namely MyD88 and NOD2, are required for *E. faecium*-mediated protection, and corresponding induction of AMP expression by *E. faecium* is abrogated in the absence of these pathways.

Figure 19:
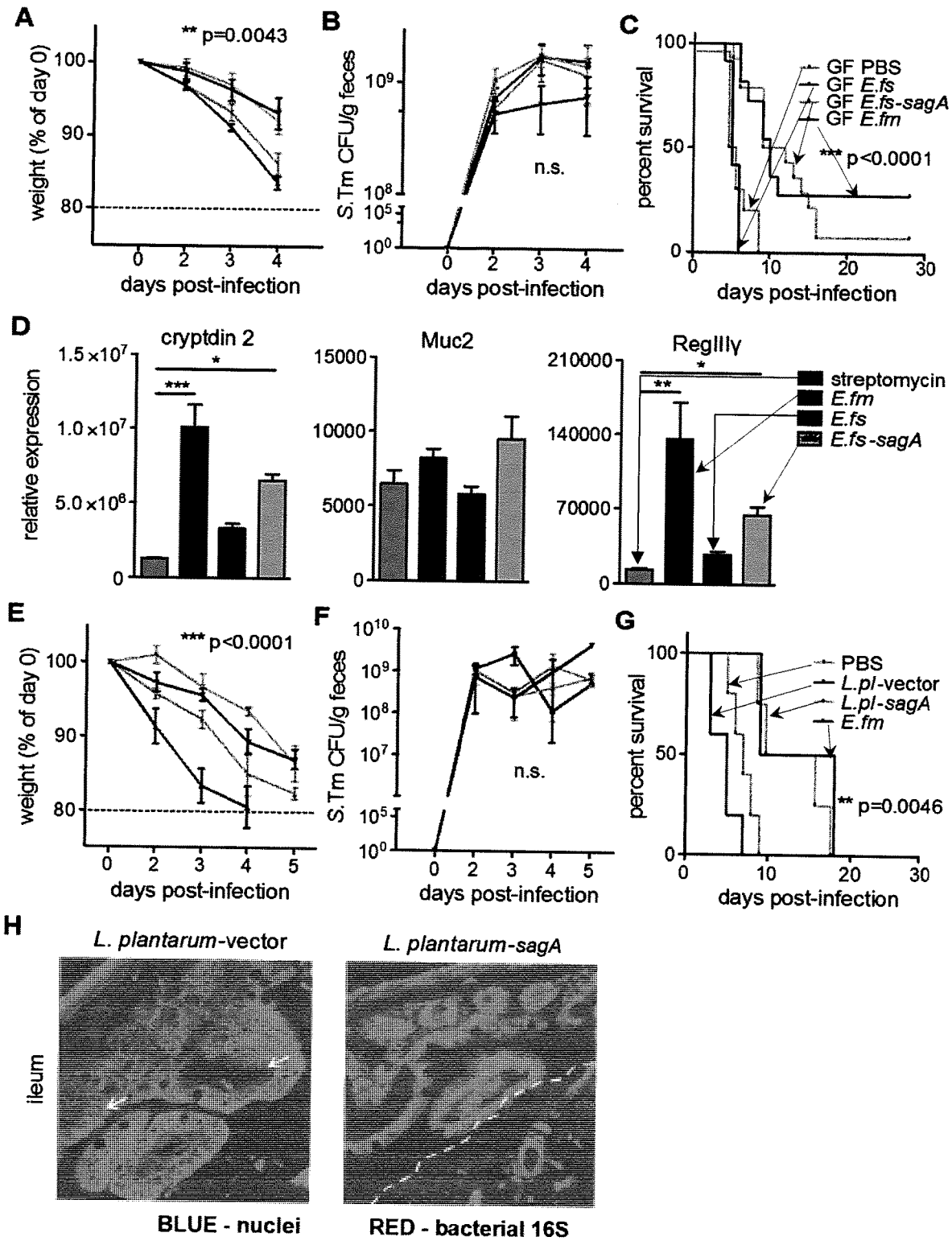
FIG. 19. The *E. faecium* protein SagA is sufficient to enhance pathogen resistance against *S. Typhimurium* and improve host intestinal barrier function. (A-C) Germ-free (GF) C57BL/6 mice were orally gavaged with $10^8$ CFU *E. faecalis* (*E. fs*), *E. faecalis* expressing sagA (*E. fs*-sagA) or *E. faecium* (*E. fm*) 7 d before oral infection with $10^2$ CFU *S. Tm*. (A) Weight loss, (B) *S. Tm* bacterial burden in feces, and (C) survival are shown. Pooled data from 4 independent experiments, n=10-14 mice/group. (D) Mice were given a single gavage of streptomycin followed 24 h later by gavage with $10^8$ CFU *E. fm*, *E. fs*, or *E. fs*-sagA. At 72 h post-colonization, IECs were isolated and analyzed by RQ-PCR. Pooled data from 2 independent experiments, n=2-4 mice/group. (E-G) Mice were given AMNV for 14 d and colonized with $10^8$ CFU *L. plantarum* harboring an empty plasmid vector (*L. pl*-vector) or a sagA plasmid (*L. pl*-sagA) or $10^8$ CFU *E. fm* prior to oral infection with $10^6$ *S. Tm*. (E) Weight loss, (F) *S. Tm* bacterial burden in feces, and (G) survival are shown. Pooled data from 2 independent experiments, n=2-5 mice/group. (H) FISH staining for all bacteria (red, universal 16S probe) and epithelial nuclei (blue, Hoechst) from intestinal tissues 48 h p.i. from mice treated before infection as in (E-G). Representative images, 45× objective, from 1 of 2 independent experiments, n=2 mice/group. White arrows indicate bacteria in contact with or invading through the epithelium, and white dashed line designates zone of segregation from bacteria. (A, B, E, and F) mean±SEM, 2-way ANOVA, p-value shown comparing sagA-expressing *E. fs* or *L. pl* to WT or vector controls, respectively, n.s.=not significant. (C and G) Log-rank analysis, p-value shown comparing sagA-expressing *E. fs* or *L. pl* to WT or vector controls, respectively. (D) mean±SEM, 1-way ANOVA with Dunnett's post-test comparing all to streptomycin-only controls. *p≤0.05, p≤0.01, *p<0.001 for all analyses.

In Example 1 in *C. elegans*, we identified that *E. faecium*-derived secreted antigen A (SagA) is a secreted N1pC/p60 peptidoglycan hydrolase that is sufficient for protection against *S. Typhimurium* in worms. Deletion of sagA has been shown to render *E. faecium* non-viable, and it is encoded in the genomes of all sequenced *E. faecium* strains; however, sagA is absent in *E. faecalis* and other known commensal species (K. L. Palmer et al., High-quality draft genome sequences of 28 *Enterococcus* sp. isolates. *J Bacteriol* 192, 2469 (May, 2010)). To determine if SagA also mediates protection against *S. Typhimurium* pathogenesis in mammals, we introduced its expression into our non-protective *Enterococcus* control, *E. faecalis*, and used it to mono-colonize gnotobiotic mice prior to *S. Typhimurium* infection. Similar to *E. faecium*, *E. faecalis*-sagA significantly improved early weight loss and survival compared to wild-type *E. faecalis*, without affecting pathogen burden (FIG. 19A-C). Moreover, both *E. faecium* and *E. faecalis*-sagA, but not wild-type *E. faecalis*, significantly induced expression of Defa2 and Reg3g in streptomycin-treated mice (FIG. 19D), indicating that expression of sagA is sufficient to increase AMP expression and attenuate *S. Typhimurium* pathogenesis.

Figure 25:
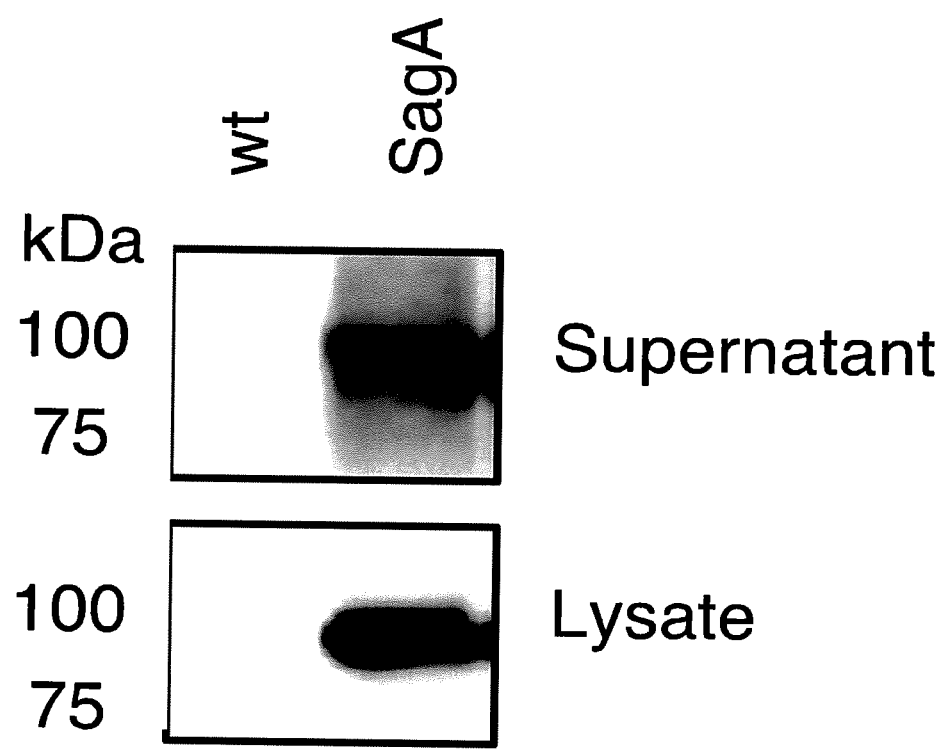
FIG. 25. Lactobacillus plantarum-sagA produces and secretes SagA. L. plantarum expressing a plasmid vector encoding his-tagged sagA were grown to stationary phase, and proteins from the supernatant and lysed cell pellet were analyzed by Western Blot for the presence of the His-tag.
Figure 26:
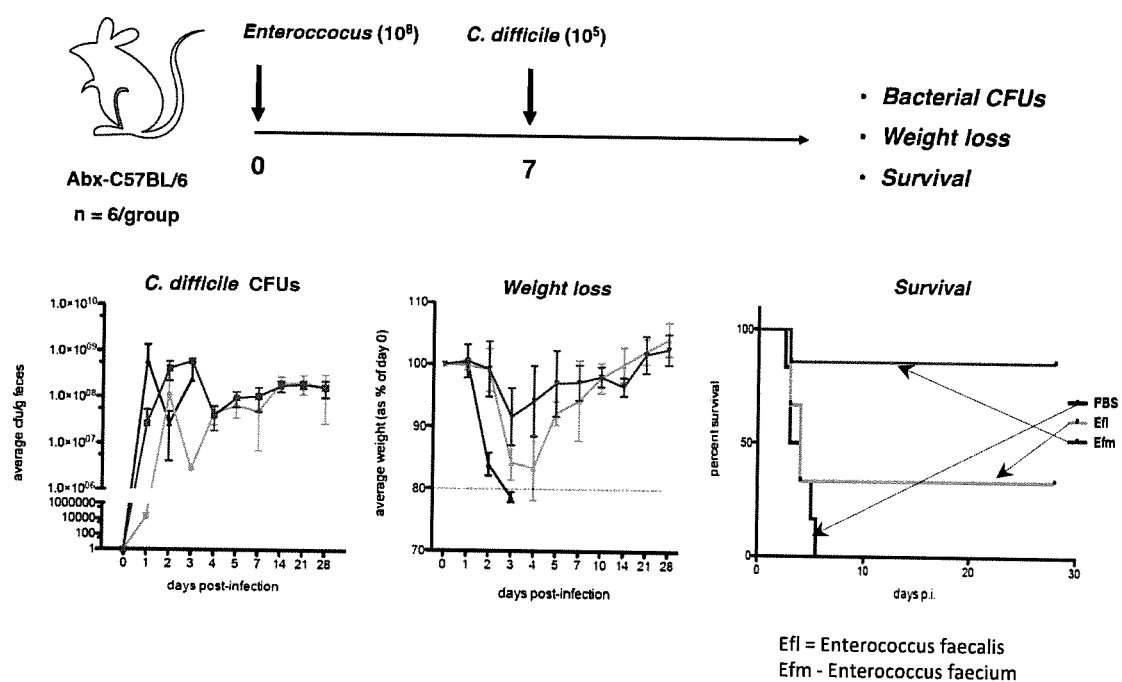
FIG. 26. Graphical summary of data demonstrating inhibition of Clostridium difficile pathogenesis in mice given SagA-expressing E. faecium.

Although *Enterococcus* strains have been used as probiotics in livestock, their pathogenic capacity makes them potentially problematic for use in humans. We thus introduced sagA into a known non-pathogenic probiotic, *Lactobacillus plantarum* (L. M. Dicks, M. Botes, Probiotic lactic acid bacteria in the gastro-intestinal tract: health benefits, safety and mode of action. *Benef Microbes* 1, 11 (March, 2010)), and confirmed that it was expressed and secreted (FIG. 25). Consistent with demonstration of protection using *E. faecalis*-sagA and *E. faecium*, sagA-expressing *L. plantarum* significantly prevented weight loss and improved survival compared to control *L. plantarum* (FIG. 19E-G). Bacterial segregation from the intestinal epithelium was also maintained in *L. plantarum*-sagA-colonized mice relative to the prominent epithelial contact and invasion present in *L. plantarum*-vector controls (FIG. 19H). These results show that SagA protective activity is transferrable to other probiotic bacteria and can enhance epithelial barrier integrity to limit *S. Typhimurium* pathogenesis.

The intestinal microbiota may have several beneficial modes of action that can potentially prevent or limit pathogenic infection, including niche competition with pathogenic bacteria, activation of immune cells and augmentation of epithelial barrier function. The present results indicate that commensal *E. faecium* does not hinder the growth of enteric pathogens in the gut, but instead utilizes a unique secreted peptidoglycan hydrolase, SagA, to increase epithelial expression of AMPs through MyD88 and NOD2 signaling pathways and enhance barrier integrity. These observations are consistent with our studies of *E. faecium* in *C. elegans* in Example 1, which also showed improved epithelial barrier integrity and SagA-mediated host resistance to *S. Typhimurium* pathogenesis. Thus, the results demonstrate a novel and conserved mechanism of pathogen resistance facilitated by bacterial peptidoglycan hydrolases and host pattern recognition receptors.

The following is a description of materials and methods used to obtain the data presented in this Example 2.

Animals.

C57BL/6J (000664), Lyz2$^{CRE}$ (004781), MyD88$^{f/f}$ (008888), Nod2$^{-/-}$ (005763), Rag I$^{-/-}$ (002216) and Reg3g$^{-/-}$ (017480) mice were purchased from Jackson Laboratories and maintained in our facilities. Villin$^{CreERT2}$ mice were developed by Silvie Robine and provided by David Artis. Several of these lines were interbred in our facilities to obtain the final strains described in this disclosure. Genotyping was performed according to the protocols established for the respective strains by Jackson Laboratories. Mice were maintained at the Rockefeller University animal facilities under specific pathogen-free (SPF) or germ-free (GF) conditions. Germ-free mice were obtained from Sarkis Mazmanian and bred and maintained in germ-free isolators in our facilities. Germ-free status was confirmed by plating feces as well as by qPCR analysis (16S rRNA). Mice were used at 8-10 weeks of age for most experiments. Animal care and experimentation were consistent with the NIH guidelines and were approved by the Institutional Animal Care and Use Committee at the Rockefeller University.

Bacteria.

*E. faecium* (strain Com15) was provided by Michael Gilmore, and *E. faecalis* (strain OG1RF) and *L. plantarum* (strain WCFS1) were provided by Balfour Sartor. *E. faecium* and *E. faecalis* were cultured in BHI broth (BD 237500), *S. Typhimurium* (strain 14028) was cultured in Luria Broth (LB) and *L. plantarum* was cultured in de Man, Rogosa and Sharpe (MRS) broth. *E. faecium*, *Efaecalis*, and *L. plantarum* were grown overnight at 37° C. at 230 rpm shaking to stationary phase growth prior to colonization. *S. Typhimurium* was grown overnight followed by a 3.5 h subculture at 37° C. at 230 rpm to log phase growth prior to infection.

Colonization and Infection of Mice.

Specific pathogen-free (SPF) mice were gavaged with either a single dose of 20 mg streptomycin or a daily dose of AMNV antibiotic cocktail (4 mg ampicillin, 2 mg metronidazole, 4 mg neomycin, and 2 mg vancomycin) for 7-14 days as indicated in the figure legends. Bacterial cultures were washed and resuspended in sterile PBS at $10^9$/mL for *E. faecium*, *E. faecalis*, and *L. plantarum* or at $10^7$/mL (SPF) or $10^3$/mL (GF) for *S. Typhimurium*. Mice were colonized by gavage with 100 uL of the indicated bacterial suspension 4 hours before infection (for streptomycin-treated mice) or 2-7 days before infection (for AMNV and GF gnotobiotic mono-colonized mice). Colonization was followed by infection with *S. Typhimurium* by oral gavage at the doses indicated above and in the figure legends. Weight loss was monitored from just before infection, and mice were euthanized when they reached 80% baseline weight or when they appeared hunched or moribund, whichever occurred first. Death was not used as an end-point. Colony-forming units (CFU) in the feces were determined by plating 5 serial dilutions of feces suspended in sterile PBS on selective agars: *Salmonella Shigella* Agar (BD 211597) for *S. Typhimurium*, Enterococcosel Agar (BD 212205) for *E. faecium* and *E. faecalis*, and MRS Agar with 8 ug/mL chloramphenicol for *L. plantarum*-vector and -SagA. Resulting quantities were normalized to feces weight.

Pathological Scoring.

Representative portions of ileum, cecum and colon were fixed in Methacarn (methanol-Carnoy) solution and embedded in paraffin according to standard protocols (see 16S FISH below). 5-μm sections were mounted on glass slides and stained withhematoxylin and eosin (H&E) for blinded histologic evaluation. Quantitative measures of inflammation were then recorded according to known methods. Briefly, each tissue section was microscopically assessed for the extent of submucosal edema, preservation of epithelial integrity and goblet cell retention (each category scored from 0-3), as well as for polymorphonuclear cell infiltration into the lamina propria (scored from 0-4). The sum of these scores represents the combined pathological score reported for each tissue. Scores ≥9 are indicative of severe inflammation, while scores of 5-8 are consistent with moderate inflammation. Scores ≤4 are associated with minimal to mild inflammation and frequently appear histologically normal.

Intestinal Permeability and Peripheral Organ Invasion.

At 48 h post-infection, mice were gavaged with FITC-dextran 4 kDa (600 μg/kg body weight) dissolved in sterile PBS. Serum was harvested by cardiac puncture after 4 h, and FITC fluorescence (excitation 488 nm and emission 518 nm) was measured in triplicate on a FLUOstar Omega microplate reader (BMG Labtech) to assess intestinal permeability. Concentration of FITC in serum was determined using a standard curve and expressed as ng/mL serum. To measure invasion, whole livers or mesenteric lymph nodes (mLN) were homogenized in PBS with 0.1% Triton X-100 to release intracellular bacteria. 3 serial dilutions were plated on *Salmonella Shigella* Agar, and resulting quantities were normalized to organ weight prior to homogenization.

16S FISH.

16S rRNA FISH was performed with a universal probe (EUB388, Cy3-GCTGCCTCCCGTAGGAGT-Cy3) on sections fixed with Methacarn solution according to known techniques. In brief, intestinal tissues (about 1 cm) including intestinal contents were fixed in Methacarn solution (60% methanol, 30% chloroform, 10% glacial acetic acid) for 6 hours at 4° C. After 3 washes with 70% ethanol tissues were embedded in paraffin. 5-μm sections were cut, mounted on glass slides, and de-paraffinized with xylene and subsequently dehydrated. Probe was diluted (5 ng/μL) in hybridization buffer (0.9 M NaCl, 20 mM Tris-HCl (pH 7.2), 0.1% SDS) and hybridization was carried out at 50° C. for 3 hours. After hybridization, tissues were washed with wash buffer (0.9 M NaCl, 20 mM Tris-HCl (pH 7.2)) and nuclei were stained with Hoechst stain. Tissues were imaged on an Inverted LSM 780 laser scanning confocal microscope (Zeiss).

Intestinal Cell Isolation.

Small intestine and large intestine were excised and freed of mesentery and fat. Feces were removed and Peyer's Patches were excised from the small intestine. Both small and large intestine were opened longitudinally and washed in HBSS, followed by HBSS+1 mM DTT (Sigma-Aldrich). Tissue was cut into 1 cm pieces and incubated with 25 mL of HBSS+2% FBS+5 mM EDTA for 15 minutes at 37° C. at 230 rpm. Supernatant containing intraepithelial lymphocytes was decanted and spun down (for RNA isolation from epithelial cells, see below). Tissue was washed with 10 mL of HBSS+2% FBS for 15 minutes at 37° C. at 230 rpm. The gut tissues were then finely chopped and digested in HBSS+ 2% FBS+1× Sodium Pyruvate+25 mM HEPES+50 μg/mL DNaseI+0.05 mg/mL Collagenase VIII for 40 min. at 37° C. at 90 rpm. Cells were separated by discontinuous Percoll gradient (70%/35%) centrifugation. Hematopoietic cells were isolated from the interphase and stained for analysis by flow cytometry.

Antibodies and Flow Cytometry Analysis.

Fluorescent-dye-conjugated antibodies were purchased from BD-Pharmingen (anti-CD4, 550954; anti-CD45R, 557683) or eBioscience (anti-CD8α 56-0081; anti-TCR-β47-5961; anti-IFN-γ, 25-7311; anti-TCRγδ, 46-5711; anti-CD8β, 46-0083; anti-TNF-α, 17-7321). Flow cytometry data were acquired on an LSR-II flow cytometer (Becton Dickinson) and analyzed using FlowJo software (Tree Star). For analysis of cytokine-secreting cells, cells were incubated in the presence of 100 ng/ml PMA (Sigma), 500 ng/ml ionomycin (Sigma) and 10 μg/ml brefeldin A (BFA) (Sigma) for the 3 h prior to staining. Cell populations were first stained with antibodies against cell surface markers, followed by permeabilization in Fix/Perm buffer and intracellular staining in Perm/Wash buffer (BD Pharmingen).

Quantitative PCR.

Epithelial cells were resuspended in Trizol (Invitrogen), RNA was isolated according to the manufacturer's protocol, and cDNA was generated using iScript (BioRad). qPCR was performed using Power SYBR Green Master Mix (Agilent) in an ABI 7900HT system. Primers used were:

|  | Forward | SEQ ID NO | Reverse | SEQ ID NO |
| --- | --- | --- | --- | --- |
| cryptdin 1 | CTAGTCCTACTCTTTGCCCT | 19 | TTGCAGCCTCTTGATCTACA | 20 |
| cryptdin 2 | CTATTGTAGAACAAGAGGCT | 21 | TCTCCATGTTCAGCGACAGC | 22 |
| cryptdin 3 | GCGTTCTCTTCTTTTGCAGC | 23 | AAACTGAGGAGCAGCCAGG | 24 |
| cryptdin 4 | GTCCAGGCTGATCCTATCCA | 25 | GGGGCAGCAGTACAAAAATC | 26 |
| cryptdin 5 | GTCCAGGCTGATCCTATCCA | 27 | GATTTCTGCAGGTCCCAAAA | 28 |
| cryptdin 6 | GTCCCATTCATGCGTTCTCT | 29 | AGGACCAGGCTGTGTCTGTC | 30 |
| Muc1 | TGCTCCTACAAGTTGGCAGA | 31 | TACCAAGCGTAGCCCCTATG | 32 |
| Muc2 | ACAAAAACCCCAGCAACAAG | 33 | GAGCAAGGGACTCTGGTCTG | 34 |
| Muc4 | GGACATGGGTGTCTGTGTTG | 35 | CTCACTGGAGAGTTCCCTGG | 36 |
| Muc13 | CTTTGTACTGTGGTGGGAGGA | 37 | TCAAGCAAGAGCAGCTACCA | 38 |
| Muc17 | ATTCAGAGGCCCCAGGTAGT | 39 | TGGCTAAACACGCTTCTCCT | 40 |
| Muc20 | CAGGAAGGACATGTGGACAA | 41 | TTCCTCCTTGTACGGCTGAC | 42 |
| Reg3g | TCCACCTCTGTTGGGTTCAT | 43 | AAGCTTCCTTCCTGTCCTCC | 44 |

Generation of *E. faecalis*-sagA and *L. plantarum*-sagA.

*L. plantarum*-sagA:

pAM401-SagA was generated as in Example 1 and transformed into *L. plantarum* WCFS1 by electroporation. Protocol for preparation of electrocompetent cells and electroporation was adapted from known approaches. Briefly, *Lactobacillus* were grown for 18 hours in M9YE (M9 media, 0.1% casamino acids, 0.3% yeast extract)+2% glycine. Cultures were diluted in half with M9YE+3% glycine, and grown for an additional 3 hours. Cultures were chilled, pelleted, and washed 3 times in sucrose wash buffer (0.625 M sucrose, 1 mM MgC12, pH 4 with HCl), reducing the original culture volume by ½, ⅒, then ¹⁄₁₀₀ successively with each wash. Finally, cells were aliquoted, flash frozen in liquid nitrogen, and stored at −80° C. Cells were electroporated in 2 mm cuvettes, 25 μF, 400 ohm, 2.5 kV. Cells were allowed to recover for 2 hours at room temperature without shaking in MRS broth (BD Bacto), then with shaking at 37° C. for another 2 hours before plating on selective media.

*E. faecalis*-sagA:

*E. faecalis*-sagA was generated as described in Example 1.

Statistics. Statistical analysis was performed in GraphPad Prism software. Data were analyzed by applying the tests indicated in each figure legend. A P value of less than 0.05 was considered significant.

While the invention has been described through specific embodiments, routine modifications will be apparent to those skilled in the art and such modifications are intended to be within the scope of the present invention.

We claim:

1. Modified bacteria that express heterologous secreted antigen A (SagA), wherein the modified bacteria are not *E. coli* and the heterologous secreted SagA comprises SEQ ID NO: 1 or a sequence that has at least 90% identity to SEQ ID NO: 1 and retains NlPc/p60-type hydrolase activity.

2. The modified bacteria of claim 1, wherein the modified bacteria are gram positive bacteria.

3. The modified bacteria of claim 2, wherein the gram positive bacteria are *Lactobacillus* bacteria.

4. The modified bacteria of claim 3, wherein the *Lactobacillus* bacteria are *L. plantarum, L. casei* or *L. acidophilus*.

5. A food product for human or non-human animal consumption comprising live modified bacteria of claim 1.

6. The food product of claim 5 wherein the food product is a dairy product.

7. The food product of claim 6, wherein the dairy product is a yogurt.

8. A probiotic formulation comprising the modified bacteria of claim 1.

9. A method comprising introducing into an individual modified bacteria of claim 1, wherein the modified bacteria express and secrete heterologous secreted antigen A (SagA).

10. The method of claim 9, wherein the modified bacteria are introduced as a component of a food product, a probiotic formulation, or a pharmaceutical formulation.

11. The method of claim 9, wherein the individual is at risk for contracting an enteric bacterial infection, or the individual is suspected of having or has been diagnosed with an enteric bacterial infection.

12. The method of claim 10, wherein the individual is at risk for contracting an enteric bacterial infection, or the individual is suspected of having or has been diagnosed with an enteric bacterial infection.

13. The modified bacteria of claim 1, wherein the heterologous secreted SagA comprises SEQ ID NO: 1.

14. The modified bacteria of claim 1, wherein the heterologous secreted SagA comprises a sequence that has at least 90% identity to SEQ ID NO: 1 and retains N1pC/p60-type hydrolase activity.

* * * * *

UNITED STATES PATENT AND TRADEMARK OFFICE
CERTIFICATE OF CORRECTION

| | |
|---|---|
| PATENT NO. | : 10,723,771 B2 |
| APPLICATION NO. | : 15/568726 |
| DATED | : July 28, 2020 |
| INVENTOR(S) | : Hang et al. |

It is certified that error appears in the above-identified patent and that said Letters Patent is hereby corrected as shown below:

In the Specification

Column 3,
Line 34, "tol-4" should read --*tol-1*--.

Column 7,
Line 34, "*$p<0.05$," should read --*$p\leq0.05$,--.

Column 9,
Line 18, "*$p<0.05$." should read --*$p\leq0.05$.--.
Line 28, "Rag1-/-/- mice" should read --*Rag1*-/- mice--.

Column 25,
Line 12, "aicd," should read --acid,--.

Column 26,
Line 31, "(MeOH/CHCl$_{3=3:7}$ to 4:6)" should read --(MeOH/CHCl$_3$ = 3.7 to 4:6)--.

Column 29,
Line 48, Row C9AQQ7, "L7" should read --L17--.

Column 31,
Line 9, Row C9APR5, "freA" should read --greA--.
Line 63, Row C9ANY1, "57.0" should read --57.9--.

Column 33,
Line 13, Row C9API4, "dehydeogenase," should read --dehydrogenase,--.
Line 17, Row C9ALR9, "synthatase F1" should read --synthase F1--.
Line 28, Table 3 header, "are bold." should read --are bold. PSM = peptide spectrum match.--.

Signed and Sealed this
Twenty-ninth Day of December, 2020

Andrei Iancu
*Director of the United States Patent and Trademark Office*

Column 35,
Line 11, Row F2MN60, "3-oxoacryl-1-[acryl-carrier-protein] synthase 2" should read --3-oxoacyl-[acyl-carrier-protein] synthase 2--.
Line 16, Row F2MRY7, "Hydoxymethylglutaryl-CoA synthase" should read --Hydroxymethylglutaryl-CoA synthase--.
Line 18, Row F2MM91, "dehydeogenase" should read --dehydrogenase--.
Line 23, Row F2MT59, "3" should read --2--.
Line 24, Row F2MRB5, "3" should read --2--.
Line 25, Row F2MTQ5, "3" should read --2--.
Line 26, Row F2MU99, "3" should read --2--.
Line 27, Row F2MM92, "3" should read --2--.

Column 37,
Line 26, Row F2MRX9, "accF" should read --aceF--.
Line 38, Table 4 header, "and bolded." should read --and bolded. PSM = peptide spectrum match.--.
Line 59, Row C9AMH5, "TS" should read --Ts--.
Line 61, Row C9AQB2, "adolase" should read --aldolase--.

Column 39,
Line 12, Row C9APM7, "phosphottransferase" should read --phosphotransferase--.
Line 25, Row C9ALV5, "uridyltransferase" should read --uridylyltransferase--.
Line 28, "C9ANG6 arcA Arginine deimiase" should read --C9AMG6 arcA Arginine deiminase--.
Line 30, Row C9ARS4, "synthtase" should read --synthetase--.
Line 67, Row C9AQM2, "nutase" should read --mutase--.

Column 43,
Line 49, "(RegIIγ)" should read --(RegIIIγ)--.

Column 46,
Line 62, "withhematoxylin" should read --with hematoxylin--.

Column 48,
Lines 23-24, "anti-TCR-β47-5961;" should read --anti-TCR-β, 47-5961;--.